US009879231B2

(12) United States Patent
Moss et al.

(10) Patent No.: US 9,879,231 B2
(45) Date of Patent: Jan. 30, 2018

(54) RECOMBINANT MODIFIED VACCINIA ANKARA (MVA) VACCINIA VIRUS CONTAINING RESTRUCTURED INSERTION SITES

(71) Applicant: The United States of America, as represented by the Secretary, Dept. of Health and Human Services, Washington, DC (US)

(72) Inventors: Bernard Moss, Bethesda, MD (US); Linda S. Wyatt, Rockville, MD (US); Patricia L. Earl, Chevy Chase, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/837,382

(22) Filed: Aug. 27, 2015

(65) Prior Publication Data
US 2016/0040135 A1    Feb. 11, 2016

Related U.S. Application Data

(62) Division of application No. 13/502,205, filed as application No. PCT/US2010/052929 on Oct. 15, 2010, now Pat. No. 9,133,480.

(60) Provisional application No. 61/252,326, filed on Oct. 16, 2009.

(51) Int. Cl.
| *C12N 7/00* | (2006.01) |
| *C07K 14/005* | (2006.01) |
| *C12N 15/86* | (2006.01) |
| *C12N 15/863* | (2006.01) |
| *A61K 39/285* | (2006.01) |
| *A61K 39/00* | (2006.01) |

(52) U.S. Cl.
CPC .............. *C12N 7/00* (2013.01); *C07K 14/005* (2013.01); *C12N 15/86* (2013.01); *C12N 15/8636* (2013.01); *A61K 39/285* (2013.01); *A61K 2039/5256* (2013.01); *C12N 2710/24121* (2013.01); *C12N 2710/24133* (2013.01); *C12N 2710/24143* (2013.01); *C12N 2710/24152* (2013.01); *C12N 2740/16122* (2013.01); *C12N 2740/16222* (2013.01)

(58) Field of Classification Search
None
See application file for complete search history.

(56) References Cited

U.S. PATENT DOCUMENTS 9,133,480 B2   9/2015   Moss et al.

FOREIGN PATENT DOCUMENTS

| EP | 2 199 400 | 6/2010 |
| WO | WO 2004/087201 A2 | 10/2004 |
| WO | WO 2008/142479 A2 | 11/2008 |

OTHER PUBLICATIONS

Wyatt et al.: "Elucidating and Minimizing the Loss by Recombinant Vaccinia Virus of Human Immunodeficiency Virus Gene Expression Resulting from Spontaneous Mutations and Positive Selection," Journal of Virology, Jul. 2009, vol. 83, No. 14, p. 7176-7184.
Official Action for European patent Application No. 10771611.0, dated Dec. 3, 2015 7 pages.
Wyatt L et al: "P19-52 LB. Assessing and restructuring foreign gene insertion sites for enhanced stability of modified Vaccinia virus ankara recombinants expressing HIV genes", Retrovirology, Biomed Central Ltd., London, GB, vol. 6, No. Suppl 3, Oct. 22, 2009 (Oct. 22, 2009) p. P416, XP021064146.
Database EMBL [Online], "Sequence 4 from Patent W02008142479." XP002614877, retrieved from EBI accession No. EMBL:GN340507 Database accession No. GN340507 compound; sequence 4, Apr. 27, 2009 (Apr. 27, 2009).
Vaccinia virus strain Ankara, complete genomic sequence, [Apr. 14, 2003] (online); [retrieved on Dec. 3, 2014]; GenBank Accession No. U94848; <URL; http://www.ncbi.nlm.nih.gov/nuccore/2772662?sat=I3&satkey=6641785>.
Timm A et al: "Genetic stability of recombinant MVA-BN", Vaccine, Elsevier Ltd, GB, vol. 24, No. 21, May 22, 2006 (May 22, 2006), pp. 4618-4621, XP025151391.
Colinas, RJ, et al., "A DNA ligase gene in the Copenhagen strain of vaccinia virus is nonessential for viral replication and recombination," Virology, Nov. 1990;179(1):267-75.
Earl et al: "Recombinant modified vaccinia virus Ankara provides durable protection against disease caused by an immunodeficiency virus as well as long-term immunity to an orthopoxvirus in a non-human primate", Virology, Academic Press,Orlando, US, vol. 366, No. 1, Aug. 29, 2007 (Aug. 29, 2007), pp. 84-97, XP022232345.
Meyer H et al: "Mapping of Deletions in the Genome of the Highly Attenuated Vaccinia Virus MVA and Their Infuence on Virulence", Journal of General Virology, Society for General Microbiology, Spencers Wood, GB, vol. 72, Jan. 1, 1991 (Jan. 1, 1991), pp. 1031-1038, XP000952390.
Wyatt et al: "Enhanced cell surface expression, immunogenicity and genetic stability resulting from a spontaneous truncation of HIV Env expressed by a recombinant MVA", Virology, Academic Press,Orlando, US, vol. 372, No. 2, Feb. 23, 2008 (Feb. 23, 2008), pp. 260-272, XP022496344.
International Search Report for PCT No. PCT/US10/52929, dated Jan. 11, 2011.

(Continued)

*Primary Examiner* — Nicole Kinsey White
(74) *Attorney, Agent, or Firm* — Sheridan Ross PC

(57) ABSTRACT

The present invention relates to recombinant modified vaccinia Ankara (MVA) virus containing restructured sites useful for the integration of heterologous nucleic acid sequences into an intergenic region (IGR) of the virus genome, where the IGR is located between two adjacent, essential open reading frames (ORFs) of the vaccinia virus genome, wherein the adjacent essential ORFs are non-adjacent in a parental MVA virus used to construct the recombinant MVA virus, and to related nucleic acid constructs useful for inserting heterologous DNA into the genome of a vaccinia virus, and further to the use of the disclosed viruses as a medicine or vaccine.

20 Claims, 47 Drawing Sheets

(56) References Cited

OTHER PUBLICATIONS

Written Opinion prepared by the European Patent Office dated Jan. 11, 2011, for International Application No. PCT/US2010/052929.
Official Action for Australia Patent Application No. 2010306559, dated Dec. 30, 2014 3 pages.
Notice of Acceptance for Australia Patent Application No. 2010306559, dated Jul. 2, 2015 2 pages.
Japanese Office Action, dated Dec. 16, 2014 in JP Patent Application No. 2012-534414 6 pages.
Notice of Allowance with English Translation for Japan Patent Application No. 2012-534414, dated Jul. 1, 2015 2 pages.
Official Action for U.S. Appl. No. 13/502,205, dated Jun. 23, 2014 10 pages Restriction Requirement.
Official Action for U.S. Appl. No. 13/502,205, dated Oct. 29, 2014 pages.
Notice of Allowance for U.S. Appl. No. 13/502,205, dated May 8, 2015 9 pages.

| Chemokine coreceptor used | PBMC replication | Macrophage replication | T-cell-line replication | REplicative phenotype | Syncytium-inducing phenotype |
|---|---|---|---|---|---|
| X4 | + | – | + | Rapid/high | ++ |
| R5 | + | + | – | Slow/low | – |
| R5/X4 | + | + | + | Rapid/high | + |

Fig. 3

```
EcoRI (1)
  1  GAATTCCCTG GGACATACGT ATATTCTAT GATCTGTCTT ATATGAAGTC TATACAGCGA ATAGATTCAG
     CTTAAGGGAC CCTGTATGCA TATAAAGATA CTAGACAGAA TATACTTCAG ATATGTCGCT TATCTAAGTC

71  AATTTCTACA TAATTATATA TTGTACGCTA ATAAGTTTAA TCTAACACTC CCCGAAGATT TGTTTATAAT
     TTAAAGATGT ATTAATATAT AACATGCGAT TATTCAAATT AGATTGTGAG GGGCTTCTAA ACAAATATTA

141  CCCTACAAAT TTGGATATTC TATGGCGTAC AAAGGAATAT ATAGACTCGT TCGATATTAG TACAGAAACA
     GGGATGTTTA AACCTATAAG ATACCGCATG TTTCCTTATA TATCTGAGCA AGCTATAATC ATGTCTTTGT

211  TGGAATAAAT TATTATCCAA TTATTATATG AAGATGATAG AGTATGCTAA ACTTTATGTA CTAAGTCCTA
     ACCTTATTTA ATAATAGGTT AATAATATAC TTCTACTATC TCATACGATT TGAAATACAT GATTCAGGAT

281  TTCTCGCTGA GGAGTTGGAT AATTTTGAGA GGACGGGAGA ATTAACTAGT ATTGTACAAG AAGCCATTTT
     AAGAGCGACT CCTCAACCTA TTAAAACTCT CCTGCCCTCT TAATTGATCA TAACATGTTC TTCGGTAAAA

351  ATCTCTAAAT TTACGAATTA AGATTTTAAA TTTTAAACAT AAAGATGATG ATACGTATAT ACACTTTGT
     TAGAGATTTA AATGCTTAAT TCTAAAATTT AAAATTTGTA TTTCTACTAC TATGCATATA TGTGAAAACA

421  AAAATATTAT TCGGTGTCTA TAACGGAACA AACGCTACTA TATATTATCA TAGACCTCTA ACGGGATATA
     TTTTATAATA AGCCACAGAT ATTGCCTTGT TTGCGATGAT ATATAATAGT ATCTGGAGAT TGCCCTATAT

AscI (539)
491  TGAATATGAT TTCAGATACT ATATTTGTTC CTGTAGATAA TAACTAAGGC GCGCCTTTCA TTTTGTTTTT
     ACTTATACTA AAGTCTATGA TATAAACAAG GACATCTATT ATTGATTCCG CGCGGAAAGT AAAACAAAAA
```

Fig. 8-1

```
561  TTCTATGCTA TAAATGGTGA GCAAGGGCGA GGAGCTGTTC ACCGGGGTGG TGCCCATCCT GGTCGAGCTG
     AAGATACGAT ATTTACCACT CGTTCCCGCT CCTCGACAAG TGGCCCCACC ACGGGTAGGA CCAGCTCGAC

631  GACGGCGACG TAAACGGCCA CAAGTTCAGC GTGTCCGGCG AGGGCGAGGG CGATGCCACC TACGGCAAGC
     CTGCCGCTGC ATTTGCCGGT GTTCAAGTCG CACAGGCCGC TCCCGCTCCC GCTACGGTGG ATGCCGTTCG

701  TGACCCTGAA GTTCATCTGC ACCACCGGCA AGCTGCCCGT GCCCTGGCCC ACCCTCGTGA CCACCCTGAC
     ACTGGGACTT CAAGTAGACG TGGTGGCCGT TCGACGGGCA CGGGACCGGG TGGGAGCACT GGTGGGACTG

771  CTACGGCGTG CAGTGCTTCA GCCGCTACCC CGACCACATG AAGCAGCACG ACTTCTTCAA GTCCGCCATG
     GATGCCGCAC GTCACGAAGT CGGCGATGGG GCTGGTGTAC TTCGTCGTGC TGAAGAAGTT CAGGCGGTAC

841  CCCGAAGGCT ACGTCCAGGA GCGCACCATC TTCTTCAAGG ACGACGGCAA CTACAAGACC CGCGCCGAGG
     GGGCTTCCGA TGCAGGTCCT CGCGTGGTAG AAGAAGTTCC TGCTGCCGTT GATGTTCTGG GCGCGGCTCC

911  TGAAGTTCGA GGGCGACACC CTGGTGAACC GCATCGAGCT GAAGGGCATC GACTTCAAGG AGGACGGCAA
     ACTTCAAGCT CCCGCTGTGG GACCACTTGG CGTAGCTCGA CTTCCCGTAG CTGAAGTTCC TCCTGCCGTT

981  CATCCTGGGG CACAAGCTGG AGTACAACTA CAACAGCCAC AACGTCTATA TCATGGCCGA CAAGCAGAAG
     GTAGGACCCC GTGTTCGACC TCATGTTGAT GTTGTCGGTG TTGCAGATAT AGTACCGGCT GTTCGTCTTC

1051 AACGGCATCA AGGTGAACTT CAAGATCCGC CACAACATCG AGGACGGCAG CGTGCAGCTC GCCGACCACT
     TTGCCGTAGT TCCACTTGAA GTTCTAGGCG GTGTTGTAGC TCCTGCCGTC GCACGTCGAG CGGCTGGTGA
```

Fig. 8-2

1121 ACCAGCAGAA CACCCCCATC GGGGACGGCC CCGTGCTGCT GCCCGACAAC CACTACCTGA GCACCCAGTC
     TGGTCGTCTT GTGGGGGTAG CCCGCTGCCGG GGCACGACGA CGGGCTGTTG GTGATGGACT CGTGGGTCAG

1191 CGCCCTGAGC AAAGACCCCA ACGAGAAGCG CGATCACATG GTCCTGCTGG AGTTCGTGAC CGCCGCCGGG
     GCGGGACTCG TTTCTGGGGT TGCTCTTCGC GCTAGTGTAC CAGGACGACC TCAAGCACTG GCGGCGGCCC

1261 ATCACTCTCG GCATGCACGA GCTGTACAAG TAAGAGCTCG AGGACGGGAG AATTAACTAG TATTGTACAA
     TAGTGAGAGC CGTACGTGCT CGACATGTTC ATTCTCGAGC TCCTGCCCTC TTAATTGATC ATAACATGTT
                                    SacI (1298)

1331 GAAGCCATTT TATCTCTAAA TTTACGAATT AAGATTTTAA ATTTTAAACA TAAAGATGAT GATACGTATA
     CTTCGGTAAA ATAGAGATTT AAATGCTTAA TTCTAAAATT TAAAATTTGT ATTTCTACTA CTATGCATAT

1401 TACACTTTTG TAAAATATTA TTCGGTGTCT ATAACGGAAC TATATTTGTT CCTGTAGATA ATAACTAACT ATAGACCTCT
     ATGTGAAAAC ATTTTATAAT AAGCCACAGA TATTGCCTTG ATATAAACAA GGACATCTAT TATTGATTGA TATCTGGAGA
                                                                                XhoI (1529)

1471 AACGGGATAT ATGAATATGA TTTCAGATAC TATATTTGTT CCTGTAGATA ATAACTAACT CGAGCCGCT
     TTGCCCTATA TACTTATACT AAAGTCTATG ATATAAACAA GGACATCTAT TATTGATTGA GCTCGGCGA

1541 GGTACCCAAC CTAAAAATTG AAAATAAATA CAAAGGTTCT TGAGGGTTGT GTTAAATTGA AAGCGAGAAA
     CCATGGGTTG GATTTTTAAC TTTTATTTAT GTTTCCAAGA ACTCCCAACA CAATTTAACT TTCGCTCTTT
     SmaI (1627)      SalI (1652)

1611 TAATCATAAA TAAGCCCGGG GATCCTCTAG AGTCGACCTG CAGTCAAACT CTAATGACCA CATCTTTTTT
     ATTAGTATTT ATTCGGGCCC CTAGGAGATC TCAGCTGGAC GTCAGTTTGA GATTACTGGT GTAGAAAAAA

Fig. 8-3

1681 TAGAGATGAA AAATTTTCCA CATCTCCTTT TGTAGACACG ACTAAACATT TTGCAGAAAA AAGTTTATTA
     ATCTCTACTT TTTAAAAGGT GTAGAGGAAA ACATCTGTGC TGATTTGTAA AACGTCTTTT TTCAAATAAT

1751 GTGTTTAGAT AATCGTATAC TTCATCAGTG TAGATAGTAA ATGTGAACAG ATAAAAGGTA TTCTTGCTCA
     CACAAATCTA TTAGCATATG AAGTAGTCAC ATCTATCATT TACACTTGTC TATTTTCCAT AAGAACGAGT

1821 ATAGATTGGT AAATTCCATA GAATATATTA ATCCTTTCTT CTTGAGATCC CACATCATTT CAACCAGAGA
     TATCTAACCA TTTAAGGTAT CTTATATAAT TAGGAAAGAA GAACTCTAGG GTGTAGTAAA GTTGGTCTCT

1891 CGTTTTATCC AATGATTTAC CTCGTACTAT ACCACATACA AAACTAGATT TTGCAGTGAC GTCGTATCTG
     GCAAAATAGG TTACTAAATG GAGCATGATA TGGTGTATGT TTTGATCTAA AACGTCACTG CAGCATAGAC

1961 GTATTCCTAC CAAACAAAAT TTTACTTTTA GTTCTTTTAG AAAAATTCTAA GGTAGAATCT CTATTGCCA
     CATAAGGATG GTTTGTTTTA AAATGAAAAT CAAGAAAATC TTTTAAGATT CCATCTTAGA GATAAACGGT

2031 ATATGTCATC TATGGAATTA CCACTAGCAA AAAAATGATAG TTCCATAATT GCCTGTATAT CATCAGCTGA AAAACTATGT
     TATACAGTAG ATACCTTAAT TGCTTAGTCT AAGGTATTAA CGGACATATA GTAGTCGACT TTTTGATACA

2101 TGATCTACTA TACTTTAAGA ACGAATCAGA TTCCATAATT GCCTGTATAT CATCAGCTGA AAAACTATGT
     ACTAGATGAT ATGAAATTTT TGCTTAGTCT AAGGTATTAA CGGACATATA GTAGTCGACT TTTTGATACA

2171 TTTACACGTA TTCCTTCGGC ATTTCTTTTT AATGATATAT CTTGTTTAGA CAATGATAAA GTTATCATGT
     AAATGTGCAT AAGGAAGCCG TAAAGAAAAA TTACTATATA GAACAAATCT GTTACTATTT CAATAGTACA

Fig. 8-4

```
2241 CCATGAGAGA CGGCTCTCCG TATCGTATAA ATATTTCATT AGATGTTAGA CGCTTCATTA GGGTATACT
     GGTACTCTCT GCCGAGAGGC ATAGCATATT TATAAAGTAA TCTACAATCT GCGAAGTAAT CCCATATGA
                                                 HindIII (2356)
2311 TCTATAAGGT TTCTTAATCA GTCCATCATT GGTTGCCTCA AGAACAAGCT TGTCTCCCTA TAGTGAGTCG
     AGATATTCCA AAGAATTAGT CAGGTAGTAA CCAACGCAGT TCTTGTTCGA ACAGAGGGAT ATCACTCAGC 2381 TATTAGAGCT TGGCGTAATC ATGGTCATAG CTGTTTCCTG TGTGAAATTG TTATCCGCTC ACAATTCCAC
     ATAATCTCGA ACCGCATTAG TACCAGTATC GACAAAGGAC ACACTTTAAC AATAGGCGAG TGTTAAGGTG 2451 ACAACATACG AGCCGGAAGC ATAAAGTGTA AAGCCTGGGG TGCCTAATGA GTGAGCTAAC TCACATTAAT
     TGTTGTATGC TCGGCCTTCG TATTTCACAT TTCGGACCCC ACGGATTACT CACTCGATTG AGTGTAATTA 2521 TGCGTTGCGC TCACTGCCCG CTTTCCAGTC GGGAAACCTG TCGTGCCAGC TGCATTAATG AATCGGCCAA
     ACGCAACGCG AGTGACGGGC GAAAGGTCAG CCCTTTGGAC AGCACGGTCG ACGTAATTAC TTAGCCGGTT 2591 CGCGCGGGGA GAGGCGGTTT GCGTATTGGG CGCTCTTCCG CTTCCTCGCT CACTGACTCG CTGCGCTCGG
     GCGCGCCCCT CTCCGCCAAA CGCATAACCC GCGAGAAGGC GAAGGAGCGA GTGACTGAGC GACGCGAGCC 2661 TCGTTCGGCT GCGGCGAGCG GTATCAGCTC ACTCAAAGGC GGTAATACGG TTATCCACAG AATCAGGGGA
     AGCAAGCCGA CGCCGCTCGC CATAGTCGAG TGAGTTTCCG CCATTATGCC AATAGGTGTC TTAGTCCCCT 2731 TAACGCAGGA AAGAACATGT GAGCAAAAGG CCAGCAACAA GCCAGGAACC GTAAAAAGGC CGCGTTGCTG
     ATTGCGTCCT TTCTTGTACA CTCGTTTTCC GGTCGTTGTT CGGTCCTTGG CATTTTTCCG GCGCAACGAC
```

Fig. 8-5

```
2801  GCGTTTTTCG ATAGGCTCCG CCCCCCTGAC GAGCATCACA AAAATCGACG CTCAAGTCAG AGGTGGCGAA
      CGCAAAAAGC TATCCGAGGC GGGGGACTG CTCGTAGTGT TTTTAGCTGC GAGTTCAGTC TCCACCGCTT

2871  ACCCGACAGG ACTATAAAGA TACCAGGCGT TTCCCCCTGG AAGCTCCCTC GTGCGCTCTC CTGTTCCGAC
      TGGGCTGTCC TGATATTTCT ATGGTCCGCA AAGGGGGACC TTCGAGGGAG CACGCGAGAG GACAAGGCTG

2941  CCTGCCGCTT ACCCGGATACC TGTCCGCCTT TCTCCCTTCG GGAAGCGTGG CGCTTTCTCA TAGCTCACGC
      GGACGGCGAA TGGGCTATGG ACAGGCGGAA AGAGGGAAGC CCTTCGCACC GCGAAAGAGT ATCGAGTGCG

3011  TGTAGGTATC TCAGTTCGGT GTAGGTCGTT CGCTCCAAGC CGGAGGTTCG GCACGAACCC CCCGTTCAGC
      ACATCCATAG AGTCAAGCCA CATCCAGCAA GCGAGGTTCG ACCCGACACA CGTGCTTGGG GGGCAAGTCG

3081  CCGACCGCTG CGCCTTATCC GGTAACTATC GTCTTGAGTC CAACCCGGTA AGACACGACT TATCGCCACT
      GGCTGGCGAC GCGGAATAGG CCATTGATAG CAGAACTCAG GTTGGGCCAT TCTGTGCTGA ATAGCGGTGA

3151  GGCAGCAGCC ACTGGTAACA GGATTAGCAG AGCGAGGTAT GTAGGCGGTG CTACAGAGTT CTTGAAGTGG
      CCGTCGTCGG TGACCATTGT CCTAATCGTC TCGCTCCATA CATCCGCCAC GATGTCTCAA GAACTTCACC

3221  TGGCCTAACT ACGGCTACAC TAGAAGGACA GTATTTGGTA TCTGCGCTCT GCTGAAGCCA GTTACCTTCG
      ACCGGATTGA TGCCGATGTG ATCTTCCTGT CATAAACCAT AGACGCGAGA CGACTTCGGT CAATGGAAGC

3291  GAAAAAGAGT TGGTAGCTCT TGATCCGGCA AACAAACCAC CGCTGGTAGC GGTGGTTTTT TTGTTTGCAA
      CTTTTTCTCA ACCATCGAGA ACTAGGCCGT TTGTTTGGTG GCGACCATCG CCACCAAAAA AACAAACGTT
```

Fig. 8-6

3361 GCAGCAGATT ACGGGCAGAA AAAAAGGATC TCAAGAAGAT CCTTTGATCT TTTCTACGGG GTCTGACGCT
     CGTCGTCTAA TGCGCGTCTT TTTTTCCTAG AGTTCTTCTA GGAAACTAGA AAAGATGCCC CAGACTGCGA

3431 CAGTGGAACG AAAACTCACG TTAAGGGATT TTGGTCATGA GATTATCAAA AAGGATCTTC ACCTAGATCC
     GTCACCTTGC TTTTGAGTGC AATTCCCTAA AACCAGTACT CTAATAGTTT TTCCTAGAAG TGGATCTAGG

3501 TTTTAAATTA AAAATGAAGT TTTAAATCAA TCTAAAGTAT ATATGAGTAA ACTTGGTCTG ACAGTTACCA
     AAAATTTAAT TTTTACTTCA AAATTTAGTT AGATTTCATA TATACTCATT TGAACCAGAC TGTCAATGGT

3571 ATGCTTAATC AGTGAGGCAC CTATCTCAGC GATCTGTCTA TTTCGTTCAT CCATAGTTGC CTGACTCCCC
     TACGAATTAG TCACTCCGTG GATAGAGTCG CTAGACAGAT AAAGCAAGTA GGTATCAACG GACTGAGGGG

3641 GTCGTGTAGA TAACTACGAT ACGGGAGGGC TTACCATCTG GCCCCAGTGC TGCAATGATA CCGCGAGACC
     CAGCACATCT ATTGATGCTA TGCCCTCCCG AATGGTAGAC CGGGGTCACG ACGTTACTAT GGCGCTCTGG

3711 CACGCTCACC GGCTCCAGAT TTATCAGCAA TAAACCAGCC AGCCGGAAGG GCCGAGCGCA GAAGTGGTCC
     GTGCGAGTGG CCGAGGTCTA AATAGTCGTT ATTTGGTCGG TCGGCCTTCC CGGCTCGCGT CTTCACCAGG

3781 TGCAACTTTA TCCGCCTCCA TCCAGTCTAT TAATTGTTGC CGGGAAGCTA GAGTAAGTAG TTCGCCAGTT
     ACGTTGAAAT AGGCGGAGGT AGGTCAGATA ATTAACAACG GCCCTTCGAT CTCATTCATC AAGCGGTCAA

3851 AATAGTTTGC GCAACGTTGT TGGCATTGCT ACAGGCATCG TGGTGTCACG CTCGTCGTTT GGTATGGCTT
     TTATCAAACG CGTTGCAACA ACCGTAACGA TGTCCGTAGC ACCACAGTGC GAGCAGCAAA CCATACCGAA

Fig. 8-7

```
3921 CATTCAGCTC CGGTTCCCAA CGATCAAGGC GAGTTACATG ATCCCCCATG TTGTGCAAAA AAGCGGTTAG
     GTAAGTCGAG GCCAAGGGTT GCTAGTTCCG CTCAATGTAC TAGGGGTAC AACACGTTTT TTCGCCAATC

3991 CTCCTTCGGT CCTCCGATCG TTGTCAGAAG TAAGTTGGCC GCAGTGTTAT CACTCATGGT TATGGCAGCA
     GAGGAAGCCA GGAGGCTAGC AACAGTCTTC ATTCAACCGG CGTCACAATA GTGAGTACCA ATACCGTCGT

4061 CTGCATAATT CTCTTACTGT CATGCCATCC GTAAGATGCT TTTCTGTGAC TGGTGAGTAC TCAACCAAGT
     GACGTATTAA GAGAATGACA GTACGGTAGG CATTCTACGA AAAGACACTG ACCACTCATG AGTTGGTTCA

4131 CATTCTGAGA ATAGTGTATG CGGCGACCGA GTTGCTCTTG CCCGGCGTCA ATACGGGATA ATACCGCGCC
     GTAAGACTCT TATCACATAC GCCGCTGGCT CAACGAGAAC GGGCCGCAGT TATGCCCTAT TATGGCGCGG

4201 ACATAGCAGA ACTTTAAAAG TGCTCATCAT TGGAAAACGT TCTTCGGGGC GAAAACTCTC AAGGATCTTA
     TGTATCGTCT TGAAATTTTC ACGAGTAGTA ACCTTTTGCA AGAAGCCCCG CTTTTGAGAG TTCCTAGAAT

4271 CCGCTGTTGA GATCCAGTTC GATGTAACCC ACTCGTGCAC CCAACTGATC TTCAGCATCT TTTACTTTCA
     GGCGACAACT CTAGGTCAAG CTACATTGGG TGAGCACGTG GGTTGACTAG AAGTCGTAGA AAATGAAAGT

4341 CCAGCCGTTTC TGGGTGAGCA AAAACAGGAA GGCAAAAATGC CGCAAAAAAG GGAATAAGGG CGACACGGAA
     GGTCGGCAAAG ACCCACTCGT TTTTGTCCTT CCGTTTTACG GCGTTTTTTC CCTTATTCCC GCTGTGCCTT

4411 ATGTTGAATA CTCATACTCT TCCTTTTTCA ATATTATTGA AGCATTTATC AGGGTTATTG TCTCATGAGC
     TACAACTTAT GAGTATGAGA AGGAAAAAGT TATAATAACT TCGTAAATAG TCCCAATAAC AGAGTACTCG
```

Fig. 8-8

```
4481  GGATACATAT TTGAATGTAT TTAGAAAAAT AAACAAATAG GGGTTCCGCG CACATTTCCC CGAAAAGTGC
      CCTATGTATA AACTTACATA AATCTTTTTA TTTGTTTATC CCCAAGGCGC GTGTAAAGGG GCTTTTCACG

4551  CACCTGACGT CTAAGAAACC ATTATTATCA TGACATTAAC CTATAAAAAT AGGCGTATCA CGAGGCCCTT
      GTGGACTGCA GATTCTTTGG TAATAATAGT ACTGTAATTG GATATTTTTA TCCGCATAGT GCTCCGGGAA

4621  TCGTCTCGCG CGTTTCGGTG ATGACGGTGA AAACCCTCTG CACATGCAGC TCCCGGAGAC GGTCACAGCT
      AGCAGAGCGC GCAAAGCCAC TACTGCCACT TTTGGGAGACT GTGTACGTCG AGGGCCTCTG CCAGTGTCGA

4691  TGTCTGTAAG CGGATGCCGG GAGCAGACAA GCCCGTCAGG GCGCGTCAGC GGGTGTTGGC GGGTGTCGGG
      ACAGACATTC GCCTACGGCC CTCGTCTGTT CGGGCAGTCC CGCGCAGTCG CCCACAACCG CCCACAGCCC

4761  GCTGGCTTAA CTATGCGGCA TCAGAGCAGA TTGTACTGAG AGTGCACCAT ATGCGGTGTG AAATACCGCA
      CGACCGAATT GATACGCCGT AGTCTCGTCT AACATGACTC TCACGTGGTA TACGCCACAC TTTATGGCGT

4831  CAGATGCGTA AGGAGAAAAT ACCGCATCAG GCGCCATTCG CCATTCAGGC TGCGCAACTG TTGGGAAGGG
      GTCTACGCAT TCCTCTTTTA TGGCGTAGTC CGCGGTAAGC GGTAAGTCCG ACGCGTTGAC AACCCTTCCC

4901  CGATCGGTGC GGGCCTCTTC GCTATTACGC CAGCTGGCGA AAGGGGGATG TGCTGCAAGG CGATTAAGTT
      GCTAGCCACG CCCGGAGAAG CGATAATGCG GTCGACCGCT TTCCCCCTAC ACGACGTTCC GCTAATTCAA

4971  GGGTAACGCC AGGGTTTTCC CAGTCACGAC GTTGTAAAAC GACGGCCAGT GAATTGGATT TAGGTGACAC
      CCCATTGCGG TCCCAAAAGG GTCAGTGCTG CAACATTTTG CTGCCGGTCA CTTAACCTAA ATCCACTGTG

5041  TATA
      ATAT
```

Fig. 8-9

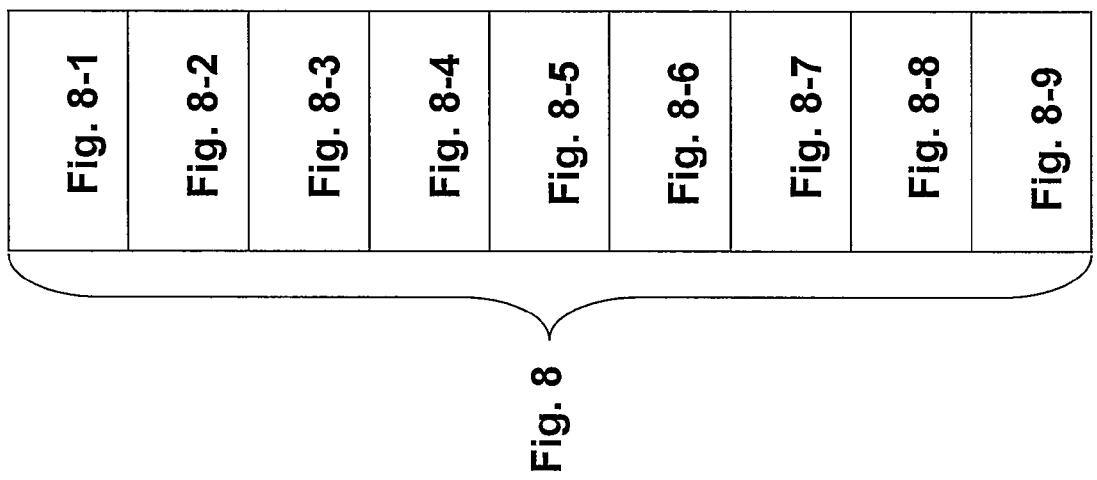

```
ATGAGAGTGAGGGAGACAGTGAGGAATTATCAGCACTTGTGGAGATGGGGCATCATGCTCC
TTGGGATGTTAATGATATGTAGTGCTGCAGACCAGCTGTGGGTCACAGTGTATTATGGGGT
ACCTGTGTGGAAAGAAGCAACCACTACTCTATTTTGTGCATCAGATGCTAAAGCACATAAA
GCAGAGGCACATAATATCTGGGCTACACATGCCTGTGTACCAACAGACCCCAATCCACGAG
AAATAATACTAGGAAATGTCACAGAAAACTTTAACATGTGGAAGAATAACATGGTAGAGCA
GATGCATGAGGATATAATCAGTTTATGGGATCAAAGTCTAAAACCATGTGTAAAATTAACC
CCACTCTGTGTTACTTTAAACTGCACTACATATTGGAATGGAACTTTACAGGGGAATGAAA
CTAAAGGGAAGAATAGAAGTGACATAATGACATGCTCTTTCAATATAACCACAGAAATAAG
AGGTAGAAAGAAGCAAGAAACTGCACTTTTCTATAAACTTGATGTGGTACCACTAGAGGAT
AAGGATAGTAATAAGACTACCAACTATAGCAGCTATAGATTAATAAATTGCAATACCTCAG
TCGTGACACAGGCGTGTCCAAAAGTAACCTTTGAGCCAATTCCCATACATTATTGTGCCCC
AGCTGGATTTGCGATTCTGAAATGTAATAATAAGACGTTCAATGGAACGGGTCCATGCAAA
AATGTCAGCACAGTACAGTGTACACATGGAATTAGGCCAGTAGTGTCAACTCAACTGTTGT
TGAATGGCAGTCTAGCAGAAGAAGAGATAATAATTAGATCTGAAAATATCACAAATAATGC
AAAAACCATAATAGTACAGCTTAATGAGTCTGTAACAATTGATTGCATAAGGCCCAACAAC
AATACAAGAAAAGTATACGCATAGGACCAGGGCAAGCACTCTATACAACAGACATAATAG
GGAATATAAGACAAGCACATTGTAATGTTAGTAAAGTAAAATGGGGAAGAATGTTAAAAAG
GGTAGCTGAAAAATTAAAAGACCTTCTTAACCAGACAAAGAACATAACTTTTGAACCATCC
TCAGGAGGGGACCCAGAAATTACAACACACAGCTTTAATTGTGGAGGGGAATTCTTCTACT
GCAATACATCAGGACTATTTAATGGGAGTCTGCTTAATGAGCAGTTTAATGAGACATCAAA
TGATACTCTCACACTCCAATGCAGAATAAAACAAATTATAAACATGTGGCAAGGAGTAGGA
AAAGCAATGTATGCCCCTCCCATTGCAGGACCAATCAGCTGTTCATCAAATATTACAGGAC
TATTGTTGACAAGAGATGGTGGTAATACTGGTAATGATTCAGAGATCTTCAGACCTGGAGG
GGGAGATATGAGAGACAATTGGAGAAGTGAATTATACAAATATAAAGTAGTAAGAATTGAA
CCAATGGGTCTAGCACCCACCAGGGCAAAAAGAAGAGTGGTGGAAAGAGAAAAAAGAGCAA
TAGGACTGGGAGCTATGTTCCTTGGGTTCTTGGGAGCGGCAGGAAGCACGATGGGCGCAGC
GTCACTGACGCTGACGGTACAGGCCAGACAGTTATTGTCTGGTATAGTGCAACAGCAAAAC
AATTTGCTGAGAGCTATAGAGGCGCAACAGCATCTGTTGCAACTCACAGTCTGGGGCATTA
AACAGCTCCAGGCAAGAGTCCTGGCTATGGAAAGCTACCTAAAGGATCAACAGCTCCTAGG
AATTTGGGGTTGCTCTGGAAAACACATTTGCACCACTACTGTGCCCTGGAACTCTACCTGG
AGTAATAGATCTGTAGAGGAGATTTGGAATAATATGACCTGGATGCAGTGGGAAAGAGAAA
TTGAGAATTACACAGGTTTAATATACACCTTAATTGAAGAATCGCAAACCCAGCAAGAAAA
GAATGAACAAGAACTATTGCAATTGGATAAATGGGCAAGTTTGTGGAATTGGTTTAGTATA
ACAAAATGGCTGTGGTATATAAAAATATTCATAATGATAGTAGGAGGCTTAATAGGTTTAA
GAATAGTTTTTGCTGTGCTTTCTTTAGTAAATAGAGTTAGGCAGGGATATTCACCTCTGTC
TTTTCAGACCCTCCTCCCAGCCCCGAGGGGACCCGACAGGCCCGAAGGAATAGAAGAAGAA
GGTGGAGAGCAAGGCTAA
```

Fig. 9

```
ATGGGTGCGAGAGCGTCAGTATTAAGCGGAGGAAAATTAGATGAATGGGAAAAAATT
CGGTTACGGCCAGGAGGAAACAAAAATATAGATTAAAACATTTAGTATGGGCAAGC
AGGGAGCTAGAACGATTTGCACTTAATCCTGGTCTTTTAGAAACATCAGAAGGCTGT
AGACAAATAATAGAACAGCTACAACCATCTATTCAGACAGGATCAGAGGAACTTAAA
TCATTACATAATACAGTAGTAACCCTCTATTGTGTACATGAAAGGATAAAGGTAGCA
GATACCAAGGAAGCTTTAGATAAGATAAAGGAAGAACAAACCAAAGTAAGAAAAAA
GCACAGCAAGCAACAGCTGACAGCAGCCAGGTCAGCCAAAATTATCCTATAGTACAA
AACCTACAGGGACAAATGGTACACCAGTCCTTATCACCTAGGACTTTGAATGCATGG
GTAAAAGTAATAGAAGAGAAGGCTTTCAGCCCAGAAGTAATACCCATGTTTTCAGCA
TTATCAGAAGGAGCCACACCAACAGATTTAAACACCATGCTAAACACAGTAGGAGGA
CATCAAGCAGCCATGCAAATGTTAAAAGAGACTATCAATGAGGAAGCTGCAGAATGG
GATAGGCTACATCCAGTGCCTGCAGGGCCTGTTGCACCAGGCCAAATGAGAGAACCA
AGAGGAAGTGATATAGCAGGAACTACCAGTACCCTTCAGGAACAAAGAAATCTATAA
AAGATGGATAATCCTAGGATTAAATAAAATAGTAAGAATGTATAGCCCTGTCAGCAT
TTTGGACATAAGACAAGGACCAAAGGAACCCTTTAGAGACTATGTAGATCGGTTCTA
TAAAACTCTACGAGCCGAGCAAGCTTCACAGGATGTAAAAAATTGGATGACTGAAAC
CTTGTTAGTCCAAAATGCGAATCCAGATTGTAAAACTATCTTAAAAGCATTGGGACC
AGCGGCTACATTAGAAGAAATGATGACAGCATGTCAGGGAGTGGGGGGACCCAGTCA
TAAAGCAAGAGTTTTGGCTGAGGCAATGAGCCAAGCATCAAACACAAATGCTGTTAT
AATGATGCAGAGGGGCAATTTCAAGGGCAAGAAAATCATTAAGTGTTTCAACTGTGG
CAAAGAAGGACACCTAGCAAAAAATTGTAGGGCTCCTAGGAAAAGAGGCTGTTGGAA
ATGTGGAAAGGAAGGGCACCAAATGAAAGATTGTAATGAAAGACAGGCTAATTTTTT
AGGGAGAATTTGGCCTTCCCACAAGGGGAGGCCAGGGAATTTCCTTCAGAGCAGACC
AGAGCCAACAGCCCCACCAGCAGAGAGCTTCGGGTTTGGGGAAGAGATAACACCCTC
CCAGAAACAGGAGGGGAAAGAGGAGCTGTATCCTTCAGCCTCCCTCAAATCACTCTT
TGGCAACGACCCCTAGTCACAATAAAAATAGGGGGACAGCTAAAGGAAGCTCTATTA
GATACAGGAGCAGATGATACAGTAGTAGAAGAAATGAATTTGCCAGGAAAATGGAAA
CCAAAAATGATAGGGGGAATTGGGGGCTTTATCAAAGTAAGACAGTATGATCAAATA
CTCGTAGAAATCTATGGATATAAGGCTACAGGTACAGTATTAGTAGGACCTACACCT
GTCAACATAATTGGAAGAAATTTGTTGACTCAGATTGGTTGCACTTTAAATTTTCCA
ATTAGTCCTATTGAAACTGTACCAGTAAAATTAAAGTCAGGGATGGATGGTCCAAGA
GTTAAACAATGGCCATTGACAGAAGAGAAAATAAAAGCACTAATAGAAATTTGTACA
GAAATGGAAAAGGAAGGAAAACTTTCAAGAATTGGACCTGAAAATCCATACAATACT
CCAATATTTGCCATAAAGAAAAAGACAGTACTAAGTGGAGAAAATTAGTAGATTTC
AGAGAACTTAATAAGAGAACTCAAGATTTCTGGGAAGTTCAACTAGGAATACCACAT
CCTGCAGGGCTAAAAAAGAAAAAATCAGTAACAGTACTGGAGGTGGGTGATGCATAT
TTTTCAGTTCCCTTATATGAAGACTTTAGAAAATACACTGCATTCACCATACCTAGT
ATAAACAATGAGACACCAGGAATTAGATATCAGTACAATGTGCTTCCACAAGGATGG
AAAGGATCACCGGCAATATTCCAAAGTAGCATGACAAAAATTTTAGAACCTTTTAGA
AAACAAAATCCAGAAGTGGTTATCTACCAATACATGCACGATTTGTATGTAGGATCT
GACTTA
```

Fig. 10-1

```
GAAATAGGGCAGCATAGAATAAAAATAGAGGAATTAAGGGGACACCTATTGAAGTGGG
GATTTACCACACCAGACAAAAATCATCAGAAGGAACCTCCATTTCTTTGGATGGGTTA
TGAACTCCATCCTGATAAATGGACAGTACAGCCTATAAAACTGCCAGAAAAAGAAAGC
TGGACTGTCAATGATCTGCAGAAGTTAGTGGGGAAATTAAATTGGGCAAGTCAAATTT
ATTCAGGAATTAAAGTAAGACAATTATGCAAATGCCTTAGGGGAACCAAAGCACTGAC
AGAAGTAGTACCACTGACAGAAGAAGCAGAATTAGAACTGGCAGAAAACAGGGAACTT
CTAAAAGAAACAGTACATGGAGTGTATTATGACCCATCAAAAGACTTAATAGCAGAAA
TACAGAAACAAGGGCAAGACCAATGGACATATCAAATTTATCAAGAACAATATAAAAA
TTTGAAAACAGGAAAGTATGCAAAGAGGAGGAGTACCCACACTAATGATGTAAAACAA
TTAACAGAGGCAGTGCAAAAAATAGCCCAAGAATGTATAGTGATATGGGGAAAGACTC
CTAAATTCAGACTACCCATACAAAAGGAAACATGGGAAACATGGTGGACAGAGTATTG
GCAGGCCACCTGGATTCCTGAGTGGGAGTTTGTCAATACCCCTCCCTTGGTTAAATTA
TGGTACCAGTTAGAGAAGGAACCCATAGTAGGAGCAGAAACCTTCTAA
```

Fig. 10-2

A
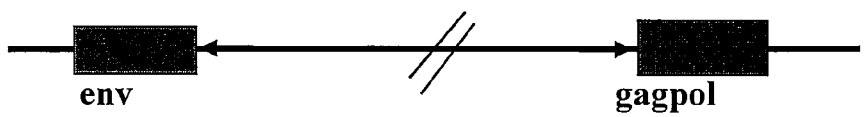
B
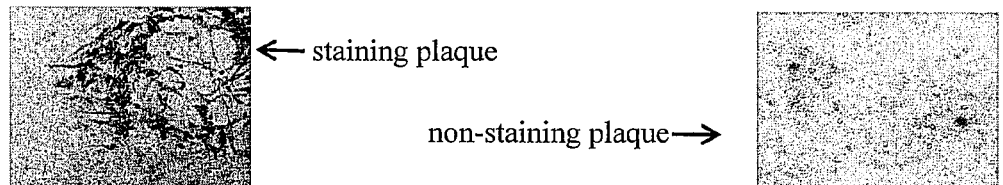
Fig. 11

| Virus | % of Non-staining Plaques at Selected Passages using HIV Env MAbs | | | | | |
|---|---|---|---|---|---|---|
| | P1 | P3 | P5 | P7 | P9 | P11 |
| MVA/UGDenv(del II) | | | 7 | | 12 | |
| MVA/UGDenv(I8/G1) | | | <1 | | | |
| MVA/UGDenv(del IIrst) | <1 | <1 | <1 | <1 | <1 | <1 |

Figure 29

EcoRI (1)
1   GAATTCGGAG TATACGAACC GGGAAAGAGA AGATGGTTAA AAATAAAGCG AGACTATTTG AACGAGGGTT
    CTTAAGCCTC ATATGCTTGG CCCTTTCTCT TCTACCAATT TTTATTTCGC TCTGATAAAC TTGCTCCCAA

71  CCATGGCAGA TTCTGCCGAT TTAGTAGTAC TAGGTGCTTA CTATGGTAAA GGAGCAAAGG GTGGTATCAT
    GGTACCGTCT AAGACGGCTA AATCATCATG ATCCACGAAT GATACCATTT CCTCGTTTCC CACCATAGTA

141 GGCAGTCTTT CTAATGGGTT GTTACGACGA TGAATCCGGT AAATGGAAGA CGGTTACCAA GTGTTCAGGA
    CCGTCAGAAA GATTACCCAA CAATGCTGCT ACTTAGGCCA TTTACCTTCT GCCAATGGTT CACAAGTCCT

211 CACGATGATA ATACGTTAAG GGAGTTGCAA GACCAATTAA AGATGATTAA AATTAACAAG GATCCCAAAA
    GTGCTACTAT TATGCAATTC CCTCAACGTT CTGGTTAATT TCTACTAATT TTAATTGTTC CTAGGGTTTT
    ──────────────────────────────────▶

281 AAATTCCAGA GTGGTTAGTA GTTAATAAAA TCTATATTCC CGATTTTGTA GTAGAGGATC CAAAACAATC
    TTTAAGGTCT CACCAATCAT CAATTATTTT AGATATAAGG GCTAAAACAT CATCTCCTAG GTTTTGTTAG

351 TCAGATATGG GAAATTTCAG GAGCAGAGTT TACATCTTCC AAGTCCCATA CCGCAAATGG AATATCCATT
    AGTCTATACC CTTTAAAGTC CTCGTCTCAA ATGTAGAAGG TTCAGGGTAT GGCGTTTACC TTATAGGTAA

421 AGATTTCCTA GATTTACTAG GATAAGAGAG GATAAAACGT GGAAAGAATC TACTCATCTA AACGATTTAG
    TCTAAAGGAT CTAAATGATC CTATTCTCTC CTATTTTGCA CCTTTCTTAG ATGAGTAGAT TTGCTAAATC

AscI (519)
491 TAAACTTGAC TAAATCTTAA TTTTTATGGC GCGCCTTTCA TTTTGTTTTT TTCTATGCTA TAAATGGTGA
    ATTTGAACTG ATTTAGAATT AAAAATACCG CGCGGAAAGT AAAACAAAAA AAGATACGAT ATTTACCACT
    ──────────────                   ──────────────────────────────▶

561 GCAAGGGCGA GGAGCTGTTC ACCGGGGTGG TGCCCATCCT GGTCGAGCTG GACGGCGACG TAAACGGCCA
    CGTTCCCGCT CCTCGACAAG TGGCCCCACC ACGGGTAGGA CCAGCTCGAC CTGCCGCTGC ATTTGCCGGT
    ◀──────────────────

631 CAAGTTCAGC GTGTCCGGCG AGGGCGAGGG CGATGCCACC TACGGCAAGC TGACCCTGAA GTTCATCTGC
    GTTCAAGTCG CACAGGCCGC TCCCGCTCCC GCTACGGTGG ATGCCGTTCG ACTGGGACTT CAAGTAGACG

Figure 31-1

701  ACCACCGGCA AGCTGCCCGT GCCCTGGCCC ACCCTCGTGA CCACCCTGAC CTACGGCGTG CAGTGCTTCA
     TGGTGGCCGT TCGACGGGCA CGGGACCGGG TGGGAGCACT GGTGGGACTG GATGCCGCAC GTCACGAAGT

771  GCCGCTACCC CGACCACATG AAGCAGCACG ACTTCTTCAA GTCCGCCATG CCCGAAGGCT ACGTCCAGGA
     CGGCGATGGG GCTGGTGTAC TTCGTCGTGC TGAAGAAGTT CAGGCGGTAC GGGCTTCCGA TGCAGGTCCT

841  GCGCACCATC TTCTTCAAGG ACGACGGCAA CTACAAGACC CGCGCCGAGG TGAAGTTCGA GGGCGACACC
     CGCGTGGTAG AAGAAGTTCC TGCTGCCGTT GATGTTCTGG GCGCGGCTCC ACTTCAAGCT CCCGCTGTGG

911  CTGGTGAACC GCATCGAGCT GAAGGGCATC GACTTCAAGG AGGACGGCAA CATCCTGGGG CACAAGCTGG
     GACCACTTGG CGTAGCTCGA CTTCCCGTAG CTGAAGTTCC TCCTGCCGTT GTAGGACCCC GTGTTCGACC

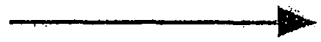

981  AGTACAACTA CAACAGCCAC AACGTCTATA TCATGGCCGA CAAGCAGAAG AACGGCATCA AGGTGAACTT
     TCATGTTGAT GTTGTCGGTG TTGCAGATAT AGTACCGGCT GTTCGTCTTC TTGCCGTAGT TCCACTTGAA

1051 CAAGATCCGC CACAACATCG AGGACGGCAG CGTGCAGCTC GCCGACCACT ACCAGCAGAA CACCCCCATC
     GTTCTAGGCG GTGTTGTAGC TCCTGCCGTC GCACGTCGAG CGGCTGGTGA TGGTCGTCTT GTGGGGGTAG

1121 GGCGACGGCC CCGTGCTGCT GCCCGACAAC CACTACCTGA GCACCCAGTC CGCCCTGAGC AAAGACCCCA
     CCGCTGCCGG GGCACGACGA CGGGCTGTTG GTGATGGACT CGTGGGTCAG GCGGGACTCG TTTCTGGGGT

1191 ACGAGAAGCG CGATCACATG GTCCTGCTGG AGTTCGTGAC CGCCGCCGGG ATCACTCTCG GCATGCACGA
     TGCTCTTCGC GCTAGTGTAC CAGGACGACC TCAAGCACTG GCGGCGGCCC TAGTGAGAGC CGTACGTGCT

SacI (1278)
1261 GCTGTACAAG TAAGAGCTCC CCGATTTTGT AGTAGAGGAT CCAAAACAAT CTCAGATATG GGAAATTTCA
     CGACATGTTC ATTCTCGAGG GGCTAAAACA TCATCTCCTA GGTTTTGTTA GAGTCTATAC CCTTTAAAGT

1331 GGAGCAGAGT TTACATCTTC CAAGTCCCAT ACCGCAAATG GAATATCCAT TAGATTTCCT AGATTTACTA
     CCTCGTCTCA AATGTAGAAG GTTCAGGGTA TGGCGTTTAC CTTATAGGTA ATCTAAAGGA TCTAAATGAT

1401 GGATAAGAGA GGATAAAACG TGGAAAGAAT CTACTCATCT AAACGATTTA GTAAACTTGA CTAAATCCTA
     CCTATTCTCT CCTATTTTGC ACCTTTCTTA GATGAGTAGA TTTGCTAAAT CATTTGAACT GATTTAGAAT

Figure 31-2

```
             XhoI (1479)
1471 ATTTTTATCT CGAGGCCGCT GGTACCCAAC CTAAAAATTG AAAATAAATA CAAAGGTTCT TGAGGGTTGT
     TAAAAATAGA GCTCCGGCGA CCATGGGTTG GATTTTTAAC TTTTATTTAT GTTTCCAAGA ACTCCCAACA

PstI (1602)
                                         SmaI (1577)    SalI (1592)
1541 GTTAAATTGA AAGCGAGAAA TAATCATAAA TAAGCCCGGG GATCCTCTAG AGTCGACCTG CAGCTAATGT
     CAATTTAACT TTCGCTCTTT ATTAGTATTT ATTCGGGCCC CTAGGAGATC TCAGCTGGAC GTCGATTACA
     ──────────────────────────────────▶

1611 ATTAGTTAAA TATTAAAACT TACCACGTAA AACTTAAAAT TTAAAATGAT ATTTCATTGA CAGATAGATC
     TAATCAATTT ATAATTTTGA ATGGTGCATT TTGAATTTTA AATTTTACTA TAAAGTAACT GTCTATCTAG
                                                          ◀──────────────────────

1681 ACACATTATG AACTTTCAAG GACTTGTGTT AACTGACAAT TGCAAAAATC AATGGGTCGT TGGACCATTA
     TGTGTAATAC TTGAAAGTTC CTGAACACAA TTGACTGTTA ACGTTTTTAG TTACCCAGCA ACCTGGTAAT
     ─────────

1751 ATAGGAAAAG GTGGATTTGG TAGTATTTAT ACTACTAATG ACAATAATTA TGTAGTAAAA ATAGAGCCCA
     TATCCTTTTC CACCTAAACC ATCATAAATA TGATGATTAC TGTTATTAAT ACATCATTTT TATCTCGGGT

1821 AAGCTAACGG ATCATTATTT ACCGAACAGG CATTTTATAC TAGAGTACTT AAACCATCCG TTATCGAAGA
     TTCGATTGCC TAGTAATAAA TGGCTTGTCC GTAAAATATG ATCTCATGAA TTTGGTAGGC AATAGCTTCT

1891 ATGGAAAAAA TCTCACAATA TAAAGCACGT AGGTCTTATC ACGTGCAAGG CATTTGGTCT ATACAAATCC
     TACCTTTTTT AGAGTGTTAT ATTTCGTGCA TCCAGAATAG TGCACGTTCC GTAAACCAGA TATGTTTAGG

1961 ATTAATGTGG AATATCGATT CTTGGTAATT AATAGATTAG GTGCAGATCT AGATGCGGTG ATCAGAGCCA
     TAATTACACC TTATAGCTAA GAACCATTAA TTATCTAATC CACGTCTAGA TCTACGCCAC TAGTCTCGGT

2031 ATAATAATAG ATTACCAAAA AGGTCGGTGA TGTTGATCGG AATCGAAATC TTAAATACCA TACAATTTAT
     TATTATTATC TAATGGTTTT TCCAGCCACT ACAACTAGCC TTAGCTTTAG AATTTATGGT ATGTTAAATA

2101 GCACGAGCAA GGATATTCTC ACGGAGATAT TAAAGCGAGT AATATAGTCT TGGATCAAAT AGATAAGAAT
     CGTGCTCGTT CCTATAAGAG TGCCTCTATA ATTTCGCTCA TTATATCAGA ACCTAGTTTA TCTATTCTTA
```

Figure 31-3

```
                                                                HindIII (2215)
2171 AAATTATATC TAGTGGATTA CGGATTGGTT TCTAAATTCA TGTCAAGCTT GTCTCCCTAT AGTGAGTCGT
     TTTAATATAG ATCACCTAAT GCCTAACCAA AGATTTAAGT ACAGTTCGAA CAGAGGGATA TCACTCAGCA 2241 ATTAGAGCTT GGCGTAATCA TGGTCATAGC TGTTTCCTGT GTGAAATTGT TATCCGCTCA CAATTCCACA
     TAATCTCGAA CCGCATTAGT ACCAGTATCG ACAAAGGACA CACTTTAACA ATAGGCGAGT GTTAAGGTGT 2311 CAACATACGA GCCGGAAGCA TAAAGTGTAA AGCCTGGGGT GCCTAATGAG TGAGCTAACT CACATTAATT
     GTTGTATGCT CGGCCTTCGT ATTTCACATT TCGGACCCCA CGGATTACTC ACTCGATTGA GTGTAATTAA 2381 GCGTTGCGCT CACTGCCCGC TTTCGAGTCG GGAAACCTGT CGTGCCAGCT GCATTAATGA ATCGGCCAAC
     CGCAACGCGA GTGACGGGCG AAAGCTCAGC CCTTTGGACA GCACGGTCGA CGTAATTACT TAGCCGGTTG 2451 GCGCGGGGAG AGGCGGTTTG CGTATTGGGC GCTCTTCCGC TTCCTCGCTC ACTGACTCGC TGCGCTCGGT
     CGCGCCCCTC TCCGCCAAAC GCATAACCCG CGAGAAGGCG AAGGAGCGAG TGACTGAGCG ACGCGAGCCA 2521 CGTTCGGCTG CGGCGAGCGG TATCAGCTCA CTCAAAGGCG GTAATACGGT TATCCACAGA ATCAGGGGAT
     GCAAGCCGAC GCCGCTCGCC ATAGTCGAGT GAGTTTCCGC CATTATGCCA ATAGGTGTCT TAGTCCCCTA 2591 AACGCAGGAA AGAACATGTG AGCAAAAGGC CAGCAAAAGG CCAGGAACCG TAAAAAGGCC GCGTTGCTGG
     TTGCGTCCTT TCTTGTACAC TCGTTTTCCG GTCGTTTTCC GGTCCTTGGC ATTTTTCCGG CGCAACGACC 2661 CGTTTTTCGA TAGGCTCCGC CCCCCTGACG AGCATCACAA AAATCGACGC TCAAGTCAGA GGTGGCGAAA
     GCAAAAAGCT ATCCGAGGCG GGGGGACTGC TCGTAGTGTT TTTAGCTGCG AGTTCAGTCT CCACCGCTTT 2731 CCCGACAGGA CTATAAAGAT ACCAGGCGTT TCCCCCTGGA AGCTCCCTCG TGCGCTCTCC TGTTCCGACC
     GGGCTGTCCT GATATTTCTA TGGTCCGCAA AGGGGGACCT TCGAGGGAGC ACGCGAGAGG ACAAGGCTGG 2801 CTGCCGCTTA CCGGATACCT GTCCGCCTTT CTCCCTTCGG GAAGCGTGGC GCTTTCTCAT AGCTCACGCT
     GACGGCGAAT GGCCTATGGA CAGGCGGAAA GAGGGAAGCC CTTCGCACCG CGAAAGAGTA TCGAGTGCGA 2871 GTAGGTATCT CAGTTCGGTG TAGGTCGTTC GCTCCAAGCT GGGCTGTGTG CACGAACCCC CCGTTCAGCC
     CATCCATAGA GTCAAGCCAC ATCCAGCAAG CGAGGTTCGA CCCGACACAC GTGCTTGGGG GGCAAGTCGG 2941 CGACCGCTGC GCCTTATCCG GTAACTATCG TCTTGAGTCC AACCCGGTAA GACACGACTT ATCGCCACTG
     GCTGGCGACG CGGAATAGGC CATTGATAGC AGAACTCAGG TTGGGCCATT CTGTGCTGAA TAGCGGTGAC 3011 GCAGCAGCCA CTGGTAACAG GATTAGCAGA GCGAGGTATG TAGGCGGTGC TACAGAGTTC TTGAAGTGGT
     CGTCGTCGGT GACCATTGTC CTAATCGTCT CGCTCCATAC ATCCGCCACG ATGTCTCAAG AACTTCACCA 3081 GGCCTAACTA CGGCTACACT AGAAGGACAG TATTTGGTAT CTGCGCTCTG CTGAAGCCAG TTACCTTCGG
     CCGGATTGAT GCCGATGTGA TCTTCCTGTC ATAAACCATA GACGCGAGAC GACTTCGGTC AATGGAAGCC
```

Figure 31-4

```
3151 AAAAAGAGTT GGTAGCTCTT GATCCGGCAA ACAAACCACC GCTGGTAGCG GTGGTTTTTT TGTTTGCAAG
     TTTTTCTCAA CCATCGAGAA CTAGGCCGTT TGTTTGGTGG CGACCATCGC CACCAAAAAA ACAAACGTTC

3221 CAGCAGATTA CGCGCAGAAA AAAAGGATCT CAAGAAGATC CTTTGATCTT TTCTACGGGG TCTGACGCTC
     GTCGTCTAAT GCGCGTCTTT TTTTCCTAGA GTTCTTCTAG GAAACTAGAA AAGATGCCCC AGACTGCGAG

3291 AGTGGAACGA AAACTCACGT TAAGGGATTT TGGTCATGAG ATTATCAAAA AGGATCTTCA CCTAGATCCT
     TCACCTTGCT TTTGAGTGCA ATTCCCTAAA ACCAGTACTC TAATAGTTTT TCCTAGAAGT GGATCTAGGA

3361 TTTAAATTAA AAATGAAGTT TTAAATCAAT CTAAAGTATA TATGAGTAAA CTTGGTCTGA CAGTTACCAA
     AAATTTAATT TTTACTTCAA AATTTAGTTA GATTTCATAT ATACTCATTT GAACCAGACT GTCAATGGTT

3431 TGCTTAATCA GTGAGGCACC TATCTCAGCG ATCTGTCTAT TTCGTTCATC CATAGTTGCC TGACTCCCCG
     ACGAATTAGT CACTCCGTGG ATAGAGTCGC TAGACAGATA AAGCAAGTAG GTATCAACGG ACTGAGGGGC

3501 TCGTGTAGAT AACTACGATA CGGGAGGGCT TACCATCTGG CCCCAGTGCT GCAATGATAC CGCGAGACCC
     AGCACATCTA TTGATGCTAT GCCCTCCCGA ATGGTAGACC GGGGTCACGA CGTTACTATG GCGCTCTGGG

3571 ACGCTCACCG GCTCCAGATT TATCAGCAAT AAACCAGCCA GCCGGAAGGG CCGAGCGCAG AAGTGGTCCT
     TGCGAGTGGC CGAGGTCTAA ATAGTCGTTA TTTGGTCGGT CGGCCTTCCC GGCTCGCGTC TTCACCAGGA

3641 GCAACTTTAT CCGCCTCCAT CCAGTCTATT AATTGTTGCC GGGAAGCTAG AGTAAGTAGT TCGCCAGTTA
     CGTTGAAATA GGCGGAGGTA GGTCAGATAA TTAACAACGG CCCTTCGATC TCATTCATCA AGCGGTCAAT

3711 ATAGTTTGCG CAACGTTGTT GGCATTGCTA CAGGCATCGT GGTGTCACGC TCGTCGTTTG GTATGGCTTC
     TATCAAACGC GTTGCAACAA CCGTAACGAT GTCCGTAGCA CCACAGTGCG AGCAGCAAAC CATACCGAAG

3781 ATTCAGCTCC GGTTCCCAAC GATCAAGGCG AGTTACATGA TCCCCCATGT TGTGCAAAAA AGCGGTTAGC
     TAAGTCGAGG CCAAGGGTTG CTAGTTCCGC TCAATGTACT AGGGGGTACA ACACGTTTTT TCGCCAATCG

3851 TCCTTCGGTC CTCCGATCGT TGTCAGAAGT AAGTTGGCCG CAGTGTTATC ACTCATGGTT ATGGCAGCAC
     AGGAAGCCAG GAGGCTAGCA ACAGTCTTCA TTCAACCGGC GTCACAATAG TGAGTACCAA TACCGTCGTG

3921 TGCATAATTC TCTTACTGTC ATGCCATCCG TAAGATGCTT TTCTGTGACT GGTGAGTACT CAACCAAGTC
     ACGTATTAAG AGAATGACAG TACGGTAGGC ATTCTACGAA AAGACACTGA CCACTCATGA GTTGGTTCAG

3991 ATTCTGAGAA TAGTGTATGC GGCGACCGAG TTGCTCTTGC CCGGCGTCAA TACGGGATAA TACCGCGCCA
     TAAGACTCTT ATCACATACG CCGCTGGCTC AACGAGAACG GGCCGCAGTT ATGCCCTATT ATGGCGCGGT
```

Figure 31-5

4061 CATAGCAGAA CTTTAAAAGT GCTCATCATT GGAAAACGTT CTTCGGGGCG AAAACTCTCA AGGATCTTAC
     GTATCGTCTT GAAATTTTCA CGAGTAGTAA CCTTTTGCAA GAAGCCCCGC TTTTGAGAGT TCCTAGAATG

4131 CGCTGTTGAG ATCCAGTTCG ATGTAACCCA CTCGTGCACC CAACTGATCT TCAGCATCTT TTACTTTCAC
     GCGACAACTC TAGGTCAAGC TACATTGGGT GAGCACGTGG GTTGACTAGA AGTCGTAGAA AATGAAAGTG

4201 CAGCGTTTCT GGGTGAGCAA AAACAGGAAG GCAAAATGCC GCAAAAAAGG GAATAAGGGC GACACGGAAA
     GTCGCAAAGA CCCACTCGTT TTTGTCCTTC CGTTTTACGG CGTTTTTTCC CTTATTCCCG CTGTGCCTTT

4271 TGTTGAATAC TCATACTCTT CCTTTTTCAA TATTATTGAA GCATTTATCA GGGTTATTGT CTCATGAGCG
     ACAACTTATG AGTATGAGAA GGAAAAAGTT ATAATAACTT CGTAAATAGT CCCAATAACA GAGTACTCGC

4341 GATACATATT TGAATGTATT TAGAAAAATA AACAAATAGG GGTTCCGCGC ACATTTCCCC GAAAAGTGCC
     CTATGTATAA ACTTACATAA ATCTTTTTAT TTGTTTATCC CCAAGGCGCG TGTAAAGGGG CTTTTCACGG

4411 ACCTGACGTC TAAGAAACCA TTATTATCAT GACATTAACC TATAAAAATA GGCGTATCAC GAGGCCCTTT
     TGGACTGCAG ATTCTTTGGT AATAATAGTA CTGTAATTGG ATATTTTTAT CCGCATAGTG CTCCGGGAAA

4481 CGTCTCGCGC GTTTCGGTGA TGACGGTGAA AACCTCTGAC ACATGCAGCT CCCGGAGACG GTCACAGCTT
     GCAGAGCGCG CAAAGCCACT ACTGCCACTT TTGGAGACTG TGTACGTCGA GGGCCTCTGC CAGTGTCGAA

4551 GTCTGTAAGC GGATGCCGGG AGCAGACAAG CCCGTCAGGG CGCGTCAGCG GGTGTTGGCG GGTGTCGGGG
     CAGACATTCG CCTACGGCCC TCGTCTGTTC GGGCAGTCCC GCGCAGTCGC CCACAACCGC CCACAGCCCC

4621 CTGGCTTAAC TATGCGGCAT CAGAGCAGAT TGTACTGAGA GTGCACCATA TGCGGTGTGA AATACCGCAC
     GACCGAATTG ATACGCCGTA GTCTCGTCTA ACATGACTCT CACGTGGTAT ACGCCACACT TTATGGCGTG

4691 AGATGCGTAA GGAGAAAATA CCGCATCAGG CGCCATTCGC CATTCAGGCT GCGCAACTGT TGGGAAGGGC
     TCTACGCATT CCTCTTTTAT GGCGTAGTCC GCGGTAAGCG GTAAGTCCGA CGCGTTGACA ACCCTTCCCG

4761 GATCGGTGCG GGCCTCTTCG CTATTACGCC AGCTGGCGAA AGGGGGATGT GCTGCAAGGC GATTAAGTTG
     CTAGCCACGC CCGGAGAAGC GATAATGCGG TCGACCGCTT TCCCCCTACA CGACGTTCCG CTAATTCAAC

4831 GGTAACGCCA GGGTTTTCCC AGTCACGACG TTGTAAAACG ACGGCCAGTG AATTGGATTT AGGTGACACT
     CCATTGCGGT CCCAAAAGGG TCAGTGCTGC AACATTTTGC TGCCGGTCAC TTAACCTAAA TCCACTGTGA
     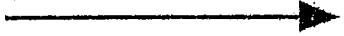

4901 ATA
     TAT

Figure 31-6

RECOMBINANT MODIFIED VACCINIA ANKARA (MVA) VACCINIA VIRUS CONTAINING RESTRUCTURED INSERTION SITES

RELATED APPLICATIONS

This application claims the benefit of U.S. Provisional Application No. 61/252,326 filed Oct. 16, 2009, which is hereby expressly incorporated by reference in its entirety.

FIELD OF THE INVENTION

The present invention relates to insertion sites useful for the stable integration of heterologous DNA sequences into the MVA genome. More specifically, the invention relates to methods of restructuring regions of the modified vaccinia Ankara (MVA) virus genome that contain a combination of essential and non-essential gene, so that heterologous DNA remains stably integrated into the genome.

BACKGROUND

The members of the poxvirus family have large double-stranded DNA genomes encoding several hundred proteins (Moss, B. 2007 "Poxviridae: The Viruses and Their Replication" in *Fields Virology*, 5*th* Ed. (D. M. Knipe, P. M. Howley, D. E. Griffin, R. A. Lamb, M. A. Martin, B. Roizman, and S. E. Straus, Eds), Lippincott Williams & Wilkins, Philadelphia, Pa.). Poxviruses are divided into the subfamilies Chordopoavirinae and Entomopaxvirinae, based on vertebrate and insect host range. The subfamily Chordopoxvirinae consists of eight genera: *Orthopoxvirus, Parapoxvirus, Avipoxvirus, Capripoxvirus, Leporipoxvirus, Suipoxvirus, Molluscipoxvirus,* and *Yatapoxvirus*. The prototypal member of the genus *Orthopoxvirus* is vaccinia virus. Vaccinia virus (VACV), the first recombinant virus shown to induce a protective immune response against an unrelated pathogen (Moss, B., G. L. Smith, J. L. Geria, and R. H. Purcell. 1984. Live recombinant vaccinia virus protects chimpanzees against hepatitis B. Nature 311:67-69; Paoletti, E., B. R, Lipinskas, C. Samsonolf S. R. Mercer, and D. Panicali. 1984. Construction of live vaccines using genetically engineered poxviruses; biological activity of vaccinia virus recombinants expressing the hepatitis B virus surface antigen and the herpes simplex virus glycoprotein D. Proc. Natl. Acad. Sci. USA 81:193-197), is being employed as a vector for veterinary and wildlife vaccines (Moss, B. 1996. Genetically engineered poxviruses for recombinant gene expression, vaccination, and safety. Proc. Natl. Acad. Sci. USA 93:11341-11348). Development of recombinant VACV for human use, however, has been impeded by safety concerns. For this reason, there is interest in modified VACV Ankara (MVA), a highly attenuated smallpox vaccine with an exemplary safety profile even in immunodeficient animals (Mayr, A., V. Hochstein-Mintzel, and H. Stickl. 1975. Passage history, properties, and applicability of the attenuated vaccinia virus strain MVA. Infection 3:6-14. (In German); Stickl, H., V. Hochstein-Mintzel, A. Mayr, H. C. Huber, H. Schafer, and A. Holzner. 1974. MVA vaccination against smallpox: clinical trial of an attenuated live vaccinia virus strain (MVA). Dtsch. Med. Wschr. 99:2386-2392 (In German); Stittelaar, K. J., T. Kuiken, R. L. de Swart, G. van Amerongen, H. W. Vos, H. G. Niesters, P. van Schalkwijk, T. van der Kwast, L. S. Wyatt, B. Moss, and A. D. Osterhaus. 2001. Safety of modified vaccinia virus Ankara (MVA) in immune-suppressed macaques. Vaccine 19:3700-3709). The genomic sequence of MVA (Mayr, A. et al. 1978 *Zentralbl Bakteriol* 167:375-390), which cannot grow in most mammalian cells and which is a good candidate for a recombinant vaccine vector, is known (Sutter, G. and Moss, B. 1992 *Proc Natl Acad Sci USA* 89:10847-10851; and Sutter, G. et al. 1994 *Vaccine* 12:1032-1040) has been passaged over 570 times in chicken embryo fibroblasts, during which six major deletions relative to the parental wild-type strain Ankara, accompanied by a severe restriction in host range, have occurred (Meyer, H. et al. 1991 *J Gen Virol* 72:1031-1038). MVA is severely host range restricted and propagates poorly or not at all in most mammalian cells because of a block in virion assembly (Sutter, G., and B. Moss. 1992. Nonreplicating vaccinia vector efficiently expresses recombinant genes. Proc. Natl. Acad. Sci. USA 89:10847-10851). Initial experiments with recombinant MVA (rMVA) demonstrated its ability to robustly express foreign proteins (Sutter, G., and B. Moss. 1992. Nonreplicating vaccinia vector efficiently expresses recombinant genes. Proc. Natl. Acad. Sci. USA 89:10847-10851) and induce protective humoral and cell-mediated immunity (Sutter, G., L. S. Wyatt, P. L. Foley, J. R. Bennink, and B. Moss. 1994. A recombinant vector derived from the host range-restricted and highly attenuated MVA strain of vaccinia virus stimulates protective immunity in mice to influenza virus. Vaccine 12:1032-1040). Currently, rMVA candidate vaccines expressing genes from a wide variety of pathogens are undergoing animal and human testing (Gomez, C. E., J. L. Najera, M. Krupa, and M. Esteban. 2008. The poxvirus vectors MVA and NYVAC a gene delivery systems for vaccination against infection diseases and cancer. Curr. Gene Ther. 8:97-120).

While developing candidate human immunodeficiency virus (HIV) and other vaccines, it was observed that mutant rMVA loses the ability to express foreign proteins after tissue culture passage (Stittelaar, K. J., L. S. Wyatt, R. L. de Swart, H. W. Vos, J. Groen, G. van Amerongen, R. S. van Binnendijk, S. Rozenblatt, B. Moss. and A. Osterhaus. 2000. Protective immunity in macaques vaccinated with a modified vaccinia virus Ankara-based measles virus vaccine in the presence of passively acquired antibodies. J. Virol, 74:4236-4243; Wyatt, L. S., I. M. Belyakov, P. L. Earl, J. A. Berzofsky, and B. Moss. 2008. Enhanced cell surface expression, immunogenicity and genetic stability resulting from a spontaneous truncation of HIV Env expressed by a recombinant MVA. Virology 372:260-272; Wyatt, L. S., S. T. Shors, B. R. Murphy, and B. Moss. 1996. Development of a replication-deficient recombinant vaccinia virus vaccine effective against parainfluenza virus 3 infection in an animal model. Vaccine 14:1451-1458). This instability may initially go undetected, however, unless individual plaques are isolated and analyzed. Nevertheless, once established in the population, the nonexpressors can rapidly overgrow the original rMVA. These considerations are particularly important for production of large vaccine seed stocks of rMVA. The instability of cloned genes in MVA is surprising, since MVA had already undergone genetic changes during its adaptation through hundreds of passages in chicken embryo fibroblasts (CEFs) and is now quite stable. Indeed, identical 167,000-bp genome sequences have been reported for three independent plaque isolates, accession numbers U94848, AY603355, and DQ983236, and by Antoine et al. (Antoine, G., F. Scheiflinger, F. Dorner, and F. G. Falkner. 2006. Corrigendum 10 "The complete genomic sequence of the modified vaccinia Ankara (MVA) strain: comparison with other orthopoxviruses." Virology 350:501-502. [Correction to 244:365, 1998.]). Although the cause of the instability of the gene inserts had not been previously investigated, harmful effects of the recombinant protein seem to play a role in the selective advantage of nonexpressing mutants. Thus, reducing the expression level of parainfluenza virus and measles virus transmembrane proteins and deleting part of the cytoplasmic tail of HIV Env improves the stability of rMVAs (Stittelaar, K. J., L. S. Wyatt, R. L. de Swart, H. W. Vos, J. Groen, G. van Amerongen, R. S. van Binnandijk, S. Rozenblatt, B. Moss. and A. Osterhaus. 2000. Protective immunity in macaques vaccinated with a modified vaccinia virus Ankara-based measles virus vaccine in the presence of passively acquired antibodies. J. Virol, 74:4236-4243; Wyatt, L. S., I. M. Belyakov, P. L. Earl, J. A. Berzofsky, and B. Moss. 2008. Enhanced cell surface expression, immunogenicity and genetic stability resulting from a spontaneous truncation of HIV Env expressed by a recombinant MVA. Virology 372:260-272; Wyatt, L. S., S. T. Shors, B. R. Murphy, and B. Moss. 1996. Development of a replication-deficient recombinant vaccinia virus vaccine effective against parainfluenza virus 3 infection in an animal model. Vaccine 14:1451-1458). Reducing expression, however, can also decrease immunogenicity and therefore may be undesirable (Wyatt, L. S., P. L. Earl, J. Vogt, L. A. Eller, D. Chandran, J. Liu, H. L. Robinson, and B. Moss. 2008. Correlation of immunogenicities and in vitro expression levels of recombinant modified vaccinia virus Ankara HIV vaccines. Vaccine 26:486-493).

In view of the potential value of rMVA as a vaccine, it is important to understand this pernicious instability problem, and to develop methods for constructing stable, recombinant MVA viruses. Additionally, an understanding of the stability problem might provide insights that have application to other DNA expression vectors. The present invention provides such insights and provides for a solution to the problem of constructing stable, recombinant MVA viruses.

SUMMARY OF THE INVENTION

The present invention relates to the discovery that the genome of a modified vaccinia Ankara (MVA) virus can be made more stable by restructuring regions of the genome. In particular, the inventors have discovered that regions of the genome containing non-essential genes are genetically unstable. Moreover such regions can be made more stable by removing non-essential DNA, and making essential genes in these regions adjacent to one another. Because loss of essential genes results in a virus having a growth disadvantage, such viruses are quickly lost from the population resulting in a population of viruses in which the essential genes, and any intervening DNA, is maintained.

The disclosure provides a recombinant modified vaccinia Ankara (MVA) virus comprising a heterologous nucleic acid sequence located between two adjacent, essential open reading frames of the MVA virus genome. The choice of essential ORFs is such that the ORFs are non-adjacent in the genome of a parental MVA virus used to construct the recombinant viruses of the present invention. That is, the essential ORFs are separated by at least one non-essential ORF. However, in the recombinant modified vaccinia Ankara (MVA) progeny virus, the essential ORFs have been made adjacent. That is, there are no intervening, non-essential ORFs between the essential ORFs. Consequently, the region between the essential ORFs is stable, and is maintained in the virus population. Consequently, this region provides a new and useful site for the insertion of heterologous nucleic acid sequences. Such heterologous nucleic acid sequences can encode therapeutically useful proteins, such as antigens.

The disclosure also provides nucleic acid constructs that can be used to construct recombinant modified vaccinia Ankara (MVA) viruses of the present invention. Such constructs contain essential ORFs from the parental MVA virus, and that are non-adjacent in the parental virus. However, in the disclosed nucleic acid constructs, these essential ORFs have been made adjacent to one another. Moreover, constructs are disclosed that contain intergenic regions between the essential ORFs, which can be used for the insertion of heterologous nucleic acid sequences.

Finally, also disclosed are methods of using viruses of the present invention for the prevention and treatment of disease.

BRIEF DESCRIPTION OF THE DRAWINGS

FIG. 3. Tropic and biologic properties of HIV-1 isolates.

FIG. 8. Nucleotide sequence of the pLW-73 transfer vector (top strand, SEQ ID NO: 2; bottom strand, SEQ ID NO: 3).

FIG. 9. Nucleotide sequence encoding Ugandan clade D Env protein (isolate AO7412) (SEQ ID NO: 4).

FIG. 11. Generation of recombinant MVAs and analysis of stability of inserted genes. A) Schematic diagram of insertion of env and gagpol into Del II and Del III sites, respectively. B) Evaluation of stability by immunostaining.

Figure 1:
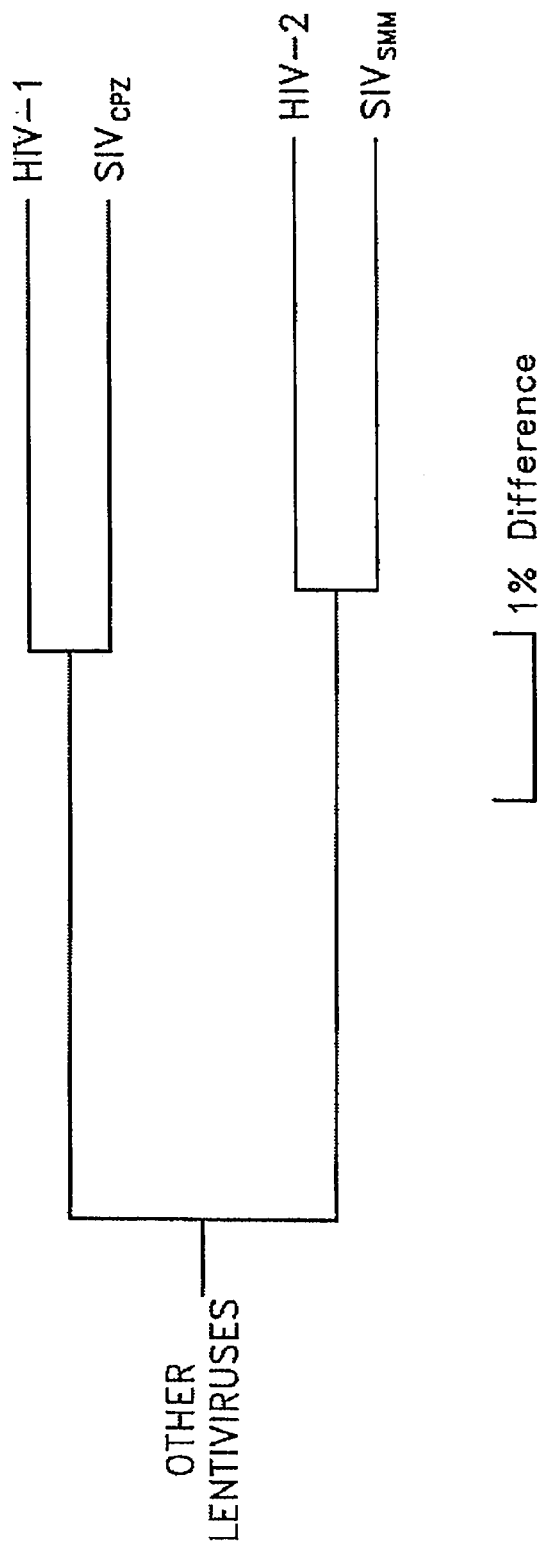
FIG. 1. Phylogenetic relationships of HIV-1 and HIV-2 based on identity of pol gene sequences. $SIV_{cpz}$ and $SIV_{smm}$ are subhuman primate lentiviruses recovered from a chimpanzee and sooty mangabey monkey, respectively.

FIG. 24. Cellular responses elicited by MVA/UGD4d.

FIG. 25. Antibody responses elicited by MVA/UGD4d.

FIG. 26. Outline of method for restructuring the del III site of MVA virus genome.

FIG. 27 pLW-76 nucleic acid construct (SEQ ID NO:21 and 22).

FIG. 28. Syncytial phenotype in rMVA due to restructuring of the del III site FIG. 29 Comparison of heterogous nucleic acid stability in different recombinant MVA viruses FIG. 30 Comparison of UGD Env protein expression level in different recombinant MVA viruses FIG. 31-1 through FIG. 31-6. Nucleotide sequence of the pLW-76 transfer vector (SEQ ID NO:21 and 22).

DEPOSIT OF MICROORGANISM

The following microorganism has been deposited in accordance with the terms of the Budapest Treaty with the American Type Culture Collection (ATCC), Manassas, Va., on the date indicated:

| Microorganism | Accession No. | Date |
|---|---|---|
| MVA 1974/NIH Clone 1 | PTA-5095 | Mar. 27, 2003 |

MVA 1974/NIH Clone 1 was deposited as ATCC Accession No.: PTA-5095 on Mar. 27, 2003 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited strain is not to be construed as a license to practice the invention in contravention of the rights granted under the authority of any government in accordance with its patent laws.

DETAILED DESCRIPTION OF THE PREFERRED EMBODIMENT

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology,* 3rd ed., J. Wiley & Sons, Chichester, N.Y., 2001 and *Fields Virology,* 5$^{th}$ Ed. (D. M. Knipe, P. M. Howley, D. E. Griffin, R. A. Lamb, M. A. Martin, B. Roizmnan, and S. E. Straus, eds), Lippincott Williams & Wilkins, Philadelphia, Pa., 2007. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

According to the present invention, an isolated protein, or nucleic acid molecule, is a protein, or nucleic acid molecule, that has been removed from its natural milieu. An isolated protein, or nucleic acid molecule, can, for example, be obtained from its natural source, be produced using recombinant DNA technology, or be synthesized chemically. As such, isolated does not reflect the state or degree to which a protein or nucleic acid molecule is purified.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

The transitional term "comprising" is synonymous with "including," "containing" or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

Complete genome sequences have been reported for at least one member of each chordopoxvirus genus and two entomopoxviruses. Nearly 100 genes are conserved in all chordopoxviruses, and about half of these are also present in entomopoxviruses. Based on the above, several generalizations can be made: Genes are largely nonoverlapping, tend to occur in blocks pointing toward the nearer end of the genome, are usually located in the central region if highly conserved and concerned with essential replication functions, and are usually located in the end regions if variable and concerned with host interactions. The arrangement of the central genes is remarkably similar in all chordopoxviruses. A convention for naming vaccinia virus genes or ORFs (open reading frames), originating prior to sequencing the entire genome and subsequently used for the complete sequence of the Copenhagen strain of vaccinia virus, consists of using the HindIII restriction endonuclease DNA fragment letter, followed by the ORF number (from left to right) within the fragment, and L or R, depending on the direction of the ORF. An exception to this rule was made for the HindIII C fragment; the ORFs were numbered from the right in order to avoid starting at the highly variable left end of the genome. Polypeptide names correspond to gene names, except that L or R is dropped. In most subsequent complete poxvirus genome sequences, ORFs were numbered successively from one end of the genome to the other. Nevertheless, the old letter designations have been retained as common names to provide continuity in the literature. The ORF number of the Western Reserve (WR) strain of vaccinia virus is commonly shown in reference books because this strain has been used for the great majority of biochemical and genetic studies.

The inventors of the present invention have identified new sites, and methods for creating new sites, for the stable insertion of exogenous DNA sequences into the genome of modified vaccinia Ankara (MVA) virus. The present invention resulted from work aimed at identifying methods of constructing stable, recombinant MVA viruses. It had previously been observed that while recombinant MVAs containing heterologous DNA sequences inserted into the MVA genome could be obtained, these insertions were often unstable. Investigations of this instability yielded the conclusion that the insertion of heterologous DNA sequences non-essential for viral propagation into spaces between ORFs could be expected to be deleted by the virus as well. Thus was recognized a need for improved strategies for constructing stable, recombinant MVA viruses.

As used herein, an open reading frame (ORF) means a string of contiguous nucleotides that encode the amino acids of a protein. Such proteins can be peptides, polypeptides, and can be any length greater than a single amino acid. It should be understood that an ORF may also include a stop codon, even though such codon does not encode an amino acid. It will be appreciated by those skilled in the art that, due to recombination events, some ORFs have lost portions of their original coding capacity and thus encode proteins that are non-functional. Such ORFs are sometimes referred to as ORF fragments. ORFs do not include regulatory elements (e.g., promoters, transcriptional control elements, enhancers, etc.) that are located outside of the coding region. In contrast, a gene refers to an ORF (including the stop codon) and regulatory elements capable of regulating transcription of the ORF.

ORFs can be referred to as adjacent or non-adjacent. As used herein, two ORFs are adjacent when they reside in the same nucleic acid molecule, and their two closest ends are not separated by another poxvirus ORF. Non-adjacent ORFs are ORFs whose two closest ends are separated by another poxvirus ORF. Adjacent ORFs can be contiguous, meaning that there is no other nucleotide sequence between a terminal codon belonging to one ORF and a terminal codon belonging to the other ORF. A terminal codon means the first or last codon of an ORF, including the stop codon. One example of a terminal codon is the codon encoding the first 5' amino acid of the protein encoded by the ORF. Another example of a terminal codon is the codon encoding the last 3' amino acid of the protein encoded by the ORF. Still another example of a terminal codon is the stop codon for the ORF.

Adjacent ORFs can also be separated by a nucleic acid sequence. Such a sequence is referred to as an intergenic region. As used herein an intergenic region means a nucleic acid sequence between the closest terminal codons of adjacent ORFs that does not contain nucleotide sequences derived from vaccinia virus, other than poxvirus transcriptional control elements. IGR sequences lie outside the stop codons of adjacent ORFs and thus do not encode any portion of the protein encoded by the adjacent ORFs. IGR sequences may contain poxvirus transcriptional control elements. IGRs may also contain sequences derived from organisms other than a poxvirus. Preferably IGRs are free of any poxvirus sequences that are not part of a poxvirus transcriptional control element. In one embodiment, the IGR comprises at least one heterologous nucleic acid sequence. Such sequence can be inserted at a restriction enzyme recognition site, or restriction site, which is naturally present in the IGR or which has been introduced into the IGR for the purpose of inserting other heterologous nucleic acid sequences.

While the nucleotide sequences of ORFs encode proteins, the intergenic regions (IGRs) between two ORFs have no coding capacity. Thus they may serve as sites into which heterologous DNA can be inserted without affecting the production of any viral proteins. IGRs may, however, comprise regulatory elements, binding sites, promoter and/or enhancer sequences essential for or involved in the transcriptional control of the viral gene expression. Thus, the IGR may be involved in the regulatory control of the viral life cycle. Even so, the inventors have found that the IGR's can be used to stably insert heterologous nucleic acid sequences into the MVA genome without influencing or changing the typical characteristics and gene expression of MVA. The new insertion sites are especially useful, since no ORF or coding sequence of MVA is altered.

Before further describing the invention, it is useful to have an understanding of the arrangement of genes in the poxvirus genome. The nucleotide sequence of an ORF regularly starts with a start codon and ends with a stop codon.

Depending on the orientation of the two adjacent ORFs the IGR, the region in between these ORFs, is flanked either by the two stop codons of the two adjacent ORFs, or, by the two start codons of the two adjacent ORFs, or, by the stop codon of the first ORF and the start codon of the second ORF, or, by the start codon of the first ORF and the stop codon of the second ORF.

Accordingly, the insertion site for the exogenous DNA sequence into the IGR may be downstream or 3' of the stop codon of a first ORF. In case the adjacent ORF, also termed second ORF, has the same orientation as the first ORF, this insertion site downstream of the stop codon of the first ORF lies upstream or 5' of the start codon of the second ORF.

In case the second ORF has an opposite orientation relative to the first ORF, which means the orientation of the two adjacent ORFs points to each other, then the insertion site lies downstream of the stop codons of both ORFs.

As a third alternative, in case the two adjacent ORFs read in opposite directions, but the orientation of the two adjacent ORFs points away from each other, which is synonymous with a positioning that is characterized in that the start codons of the two ORFs are adjacent to each other, then the exogenous DNA is inserted upstream relative to both start codons.

ORFs in the MVA genome occur in two coding directions. Consequently, mRNA synthesis activity occurs from left to right, i.e., forward direction and, correspondingly, from right to left (reverse direction). It is common practice in poxvirology and it became a standard classification for vaccinia viruses to identify ORFs by their orientation and their position on the different HindIII restriction digest fragments of the genome. For the nomenclature, the different HindIII fragments are named by descending capital letters corresponding with their descending size. The ORF are numbered from left to right on each HindIII fragment and the orientation of the ORF is indicated by a capital L (standing for transcription from right to Left) or R (standing for transcription from left to Right). Additionally, there is a more recent publication of the MVA genome structure, which uses a different nomenclature, simply numbering the ORF from the left to the right end of the genome and indicating their orientation with a capital L or R (Antoine, G. et al. 1998 *Virology* 244:365-396). As an example the I8R ORF, according to the old nomenclature, corresponds to the 069R ORF according to Antoine et al.

In their efforts to make recombinants of modified vaccinia virus Ankara (MVA) expressing HIV genes as candidate vaccines, the inventors determined that one of the causes of instability is due to deletions of the foreign gene and flanking MVA sequences. In an attempt to overcome this problem they set out to insert foreign genes between conserved genes in order to prevent viable deletions from occurring in recombinant MVAs. Viruses with such deletions have a growth advantage and will thus overgrow rMVA virus populations. If one inserts foreign genes between conserved genes in the vaccinia genome (these genes are considered to be required for vaccinia virus replication and are therefore "essential genes"), any deletion of an essential gene would inhibit virus replication, and, therefore, not overgrow the recombinant MVAs. Thus, the stable expression of the rMVA population is maintained. The strain of MVA that the inventors have been using to make their recombinants was provided by them to the Centers for Disease Control and Prevention (CDC) and was subsequently sequenced by Acambis (Genbank Accession number AY603355). The strain of MVA that Bavarian Nordic has based their WO03/097845 publication on is vaccinia virus strain modified vaccinia Ankara (Genbank Accession number U94848) sequenced by Antoine, G. et al. 1998 *Virology* 244:365-396. (Note that the gene numbers in these two sequences for a given gene are different.)

The inventors initially looked at genes conserved in the Poxviridae family as well as those genes conserved in subfamily Chordopoxvirinae (the vertebrate poxviruses) (Upton, C. et al. 2003 *Journal of Virology* 77:7590-7600). These genes are listed in the nomenclature of Copenhagen vaccinia virus (Genbank Accession number M35027) given on the Poxvirus Bioinformatics Resource Center found on the world wide web at poxvirus.org. These genes total 49 conserved genes in the Poxvirus family and 41 additional genes conserved in chordopoxviruses, making a total of 90 conserved genes. From these 90 conserved genes, the inventors listed intergenic sites between conserved gene pairs. These gene pairs re listed below in Table 1. (Note that genes are marked that have not been included in the Bavarian Nordic WO03/097845 publication).

TABLE 1

Intergenic Sites between Conserved Genes

| Genes/ Copenhagen | CDC/ Acambis Genes | Antoine et al. Genes | Listed in WO03/097845 publ? N = No |
|---|---|---|---|
| F9L-F10L | 040-041 | 038L-039L | |
| F12L-F13L | 044-045 | 042L-043L | N |
| F17R-E1L | 049-050 | 047R-048L | N |
| E1L-E2L | 050-051 | 048L-049L | N |
| E8R-E9L | 057-058 | 055R-056L | |
| E9L-E10R | 058-059 | 056L-057L | N |
| I1L-I2L | 064-065 | 062L-063L | N |
| I2L-I3L | 065-066 | 063L-064L | N |
| I5L-I6L | 068-069 | 066L-067L | |
| I6L-I7L | 069-070 | 067L-068L | N |
| I7L-I8R | 070-071 | 068L-069R | N |
| I8R-G1L | 071-072 | 069R-070L | N |
| G1L-G3L | 072-073 | 070L-071L | N |
| G3L-G2R | 073-074 | 071L-072R | N |
| G2R-G4L | 074-075 | 072R-073L | N |
| G4L-G5R | 075-076 | 073L-074R | N |
| G5R-G5.5R | 076-077 | 074R-075R | N |
| G5.5R-G6R | 077-078 | 075R-076R | N |
| G6R-G7L | 078-079 | 076R-077L | N |
| G7L-G8R | 079-080 | 077L-078R | |
| G8R-G9R | 080-081 | 078R-079R | |
| G9R-L1R | 081-082 | 079R-080R | N |
| L1R-L2R | 082-083 | 080R-081R | |
| L2R-L3L | 083-084 | 081R-082L | |
| L3L-L4R | 084-085 | 082L-083R | |
| L4R-L5R | 085-086 | 083R-084R | N |
| L5R-J1R | 086-087 | 084R-085R | N |
| J3R-J4R | 089-090 | 087R-088R | N |
| J4R-J5L | 090-091 | 088R-089L | |
| J5L-J6R | 091-092 | 089L-090R | |
| J6R-H1L | 092-093 | 090R-091L | N |
| H1L-H2R | 093-094 | 091L-092R | N |
| H2R-H3L | 094-095 | 092R-093L | |
| H3L-H4L | 095-096 | 093L-094L | N |
| H4L-H5R | 096-097 | 094L-095R | |
| H5R-H6R | 097-098 | 095R-096R | N |
| H6R-H7R | 098-099 | 096R-097R | |
| H7R-D1R | 099-100 | 097R-098R | |
| D1R-D2L | 100-101 | 098R-099L | N |
| D2L-D3R | 101-102 | 099L-100R | N |
| D3R-D4R | 102-103 | 100R-101R | N |
| D4R-D5R | 103-104 | 101R-102R | |
| D5R-D6R | 104-105 | 102R-103R | N |
| D6R-D7R | 105-106 | 103R-104R | |
| D9R-D10R | 108-109 | 106R-107R | N |
| D10R-D11L | 109-110 | 107R-108L | |
| D11L-D12L | 110-111 | 108L-109L | |
| D12L-D13L | 111-112 | 109L-110L | |
| D13L-A1L | 112-113 | 110L-111L | |

TABLE 1-continued Intergenic Sites between Conserved Genes

| Genes/ Copenhagen | CDC/ Acambis Genes | Antoine et al. Genes | Listed in WO03/097845 publ? N = No |
|---|---|---|---|
| A1L-A2L | 113-114 | 111L-112L | N |
| A2L-A2.5L | 114-115 | 112L-113L | N |
| A2.5L-A3L | 115-116 | 113L-114L | |
| A3L-A4L | 116-117 | 114L-115L | |
| A4L-A5R | 117-118 | 115L-116R | |
| A5R-A6L | 118-119 | 116R-117L | N |
| A6L-A7L | 119-120 | 117L-118L | |
| A7L-A8R | 120-121 | 118L-119R | |
| A8R-A9L | 121-122 | 119R-120L | N |
| A9L-A10L | 122-123 | 120L-121L | N |
| A10L-A11R | 123-124 | 121L-122R | N |
| A11R-A12L | 124-125 | 122R-123L | |
| A12L-A13L | 125-126 | 123L-124L | |
| A13L-A14L | 126-127 | 124L-125L | |
| A14L-A14.5L | 127-128 | 125L-125.5L | N |
| A14.5L-A15L | 128-129 | 125.5L-126L | N |
| A15L-A16L | 129-130 | 126L-127L | N |
| A16L-A17L | 130-131 | 127L-128L | N |
| A17L-A18R | 131-132 | 128L-129R | N |
| A18R-A19L | 132-133 | 129R-130L | N |
| A19L-A21L | 133-134 | 130L-131L | N |
| A21L-A20R | 134-135 | 131L-132R | N |
| A20R-A22R | 135-136 | 132R-133R | N |
| A22R-A23R | 136-137 | 133R-134R | |
| A23R-A24R | 137-138 | 134R-135R | |
| A28L-A29L | 141-142 | 139L-140L | N |
| A29L-A30L | 142-143 | 140L-141L | N |

The orientations of these genes are variable, with some being transcribed to the right, some to the left. This means that some of the intergenic sites contain promoters that would have to be preserved in the construction of the insertion vector. In addition, for overlapping conserved genes, during vector construction the genes would have to be reconstructed using alternative codons to minimize the repeating sequences The inventors focused on conserved genes whose orientation is "end to end" such that the 3' stop codon of the genes are in close proximity to one another. The construction of transfer vectors used in these sites are facilitated by the fact that there would be no promoter in this region between the stop codons. If there are intergenic nucleotides separating the stop codons, then construction of the insertion vector is straightforward. If the stop codon of one gene is within the 3' end of the other gene, then during construction of the plasmid transfer vector, the gene can be reconstructed using alternative codons to minimize repeating sequences, or, depending on the size of the overlap, simply corrected in the PCR of the flanks so as not to overlap. Table 2 gives the intergenic sites that meet the requirement of the orientation of the conserved genes being "end to end". The intergenic sites highlighted in bold typeface have no overlapping ends and therefore are simplest to construct.

TABLE 2

Conserved genes with "end to end" orientation

| Genes end to end | Overlapping ends | CDC/Acambis genes | Antoine genes |
|---|---|---|---|
| F17R-E1L | Yes | 049-050 | 047R-048L |
| E8R-E9L | No | 057-058 | 055R-056L |
| I8R-G1L | No | 071-072 | 069R-070L |
| G2R-G4L | Yes | 074-075 | 072R-073L |
| G6R-G7L | Yes | 078-079 | 076R-077L |
| L2R-L3L | Yes | 083-084 | 081R-082L |
| J4R-J5L | No | 090-091 | 088R-089L |
| J6R-H1L | Yes | 092-093 | 090R-091L |
| H2R-H3L | No | 094-095 | 092R-093L |
| D1R-D2L | Yes | 100-101 | 098R-099L |
| D10R-D11L | No | 109-110 | 107R-108L |
| A5R-A6L | Yes | 118-119 | 116R-117L |
| A8R-A9L | Yes | 121-122 | 119R-120L |
| A11R-A12L | No | 124-125 | 122R-123L |
| A18R-A19L | Yes | 132-133 | 129R-130L |

The highlighted (in bold typeface) genes have no overlapping ends and thus are simplest to use as intergenic sites.

From this list, the inventors focused on the six intergenic sites that have no overlapping ends. In a working example, of these six, the intergenic site, 071-072 (I8R-G1L), was chosen as a site into which to insert a heterologous gene. The construction of a recombinant MVA virus using this intergenic site, and the characteristics of the resultant virus, are described in Example 1, and in International Publication Number WO2008/142479 A2, which is herein incorporated by reference in its entirety.

In addition to the conserved genes and corresponding intergenic sites described above, the inventors have discovered other sites useful for the insertion of a heterologous nucleic acid sequence. For example, any gene, for which it has been experimentally demonstrated that the deletion, or inactivation, of which, results in a 0.5 log, 0.75 log or 1 log (10 fold) reduction in titer, could be considered an "essential gene". Similarly, an essential gene is any gene that results in at least an 50%, at least a 75%, or at least a 90% reduction in titer compared to a virus in which the corresponding gene has not been deleted or inactivated. If this gene lies adjacent to another essential gene, the intergenic site between the two genes would be a useful site for insertion of a heterologous nucleic acid sequence. While deletion of one or more of these ORF, along with the intervening heterologous nucleic acid sequence, would not prevent the virus from growing, it would result in decreased growth compared to a virus containing these ORFs. Thus, over time, virus that has lost one or more essential ORF would slowly become a smaller proportion of the total virus population and, given enough time, would disappear from the virus population entirely.

Thus, one embodiment of the present invention is a recombinant modified vaccinia Ankara (MVA) virus comprising a heterologous nucleic acid sequence located between, or flanked by, two adjacent essential ORFs from MVA virus. In one embodiment, adjacent ORF's are separated by an intergenic region (IGR). As described, the IGR may contain a heterologous nucleic acid sequence. Thus, one embodiment is a recombinant modified vaccinia Ankara (MVA) virus comprising a heterologous nucleic acid sequence in an intergenic region located between, or flanked by, two adjacent essential ORFs from MVA virus.

As used herein, heterologous, or exogenous, nucleic acid sequences are sequences which, in nature, are not normally found associated with the poxvirus as used according to the present invention. According to a further embodiment of the present invention, the exogenous nucleic acid sequence comprises at least one coding sequence. The coding sequence is operatively linked to a transcription control element, preferably to a poxviral transcription control element. Additionally, also combinations between poxviral transcription control element and, e.g., internal ribosomal entry sites can be used.

According to a further embodiment, the heterologous nucleic acid sequence can also comprise two or more coding sequences linked to one or several transcription control elements. Preferably, the coding sequence encodes one or more proteins. In some embodiments, the proteins are antigens, or comprise antigenic epitopes, especially those of therapeutically interesting genes.

Therapeutically interesting genes according to the present invention may be genes derived from or homologous to genes of pathogenous or infectious microorganisms which are disease causing. Accordingly, in the context of the present invention such therapeutically interesting genes are presented to the immune system of an organism in order to affect, preferably induce a specific immune response and, thereby, vaccinate or prophylactically protect the organism against an infection with the microorganism. In further preferred embodiments of the present invention the therapeutically interesting genes are selected from genes of infectious viruses, e.g., —but not limited to—dengue virus, hepatitis virus B or C, or human immunodeficiency viruses such as HIV.

According to a preferred embodiment of the present invention the heterologous nucleic acid sequence is derived from HIV and encodes HIV env, wherein the HIV env gene is preferably inserted into the IGR between the adjacent ORFs. The etiological agent of acquired immune deficiency syndrome (AIDS) is recognized to be a retrovirus exhibiting characteristics typical of the lentivirus genus, referred to as human immunodeficiency virus (HIV). The phylogenetic relationships of the human lentiviruses are shown in FIG. 1. HIV-2 is more closely related to $SIV_{smm}$, a virus isolated from sooty mangabey monkeys in the wild, than to HIV-1. It is currently believed that HIV-2 represents a zoonotic transmission of $SIV_{smm}$ to man. A series of lentiviral isolates from captive chimpanzees, designated $SIV_{cpz}$, are close genetic relatives of HIV-1.

Figure 2:
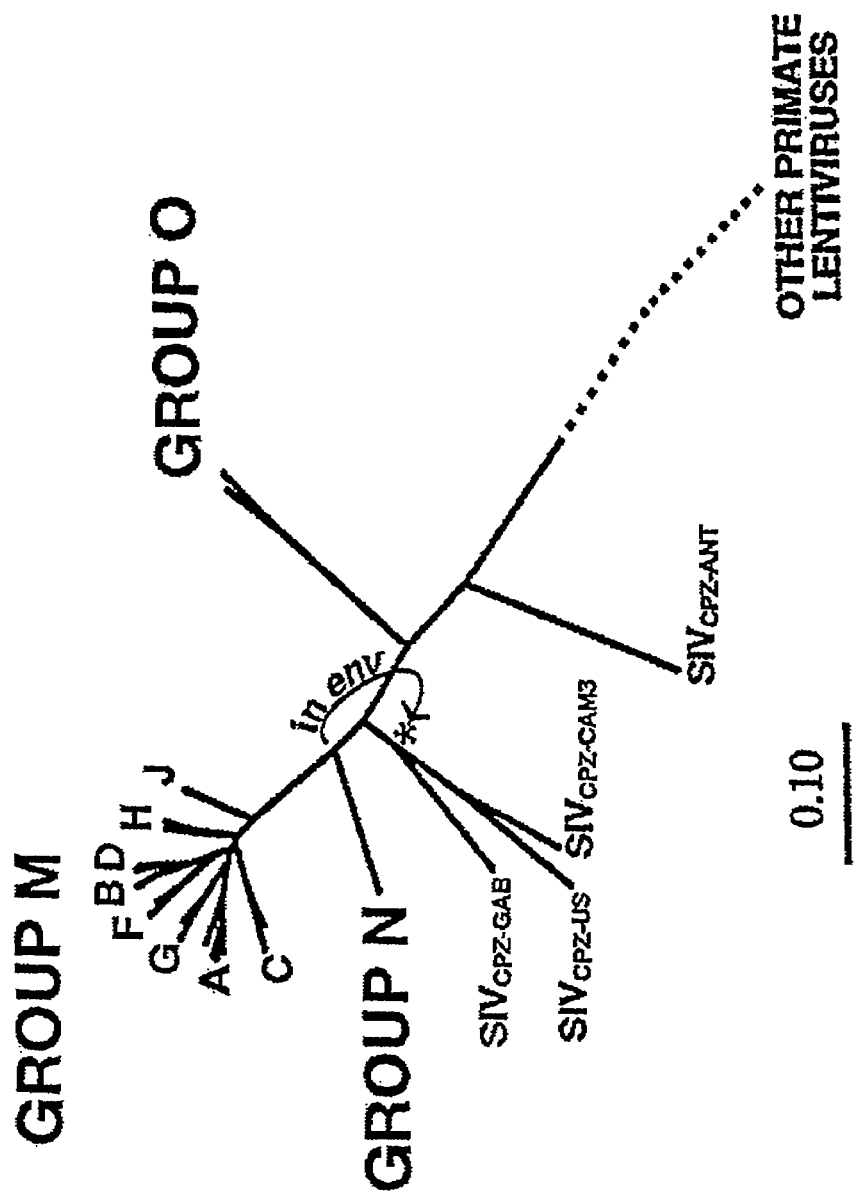
FIG. 2. Phylogenetic relationships of HIV-1 groups M, N and O with four different $SIV_{cpz}$ isolates based on full-length pol gene sequences. The bar indicates a genetic distance of 0.1 (10% nucleotide divergence) and the asterisk positions group N HIV-1 isolates based on env sequences.

The earliest phylogenetic analyses of HIV-1 isolates focused on samples from Europe/North America and Africa; discrete clusters of viruses were identified from these two areas of the world. Distinct genetic subtypes or clades of HIV-1 were subsequently defined and classified into three groups: M (major); O (outlier); and N (non-M or O) (FIG. 2). The M group of HIV-1, which includes over 95% of the global virus isolates, consists of at least eight discrete clades (A, B, C, D, F, G, H, and J), based on the sequence of complete viral genomes. Members of HIV-1 group O have been recovered from individuals living in Cameroon, Gabon, and Equatorial Guinea; their genomes share less than 50% identity in nucleotide sequence with group M viruses. The more recently discovered group N HIV-I strains have been identified in infected Cameroonians, fail to react serologically in standard whole-virus enzyme-linked immunosorbent assay (ELISA), yet are readily detectable by conventional Western blot analysis.

Most current knowledge about HIV-1 genetic variation comes from studies of group M viruses of diverse geographic origin. Data collected during the past decade indicate that the HIV-1 population present within an infected individual can vary from 6% to 10% in nucleotide sequence. HIV-1 isolates within a clade may exhibit nucleotide distances of 15% in gag and up to 30% in gp120 coding sequences. Interclade genetic variation may range between 30% and 40% depending on the gene analyzed.

All of the HIV-1 group M subtypes can be found in Africa. Clade A viruses are genetically the most divergent and were the most common HIV-1 subtype in Africa early in the epidemic. With the rapid spread of HIV-1 to southern Africa during the mid to late 1990s, clade C viruses have become the dominant subtype and now account for 48% of HIV-1 infections worldwide. Clade B viruses, the most intensively studied HIV-1 subtype, remain the most prevalent isolates in Europe and North America.

High rates of genetic recombination are a hallmark of retroviruses. It was initially believed that simultaneous infections by genetically diverse virus strains were not likely to be established in individuals at risk for HIV-1. By 1995, however, it became apparent that a significant fraction of the HIV-1 group M global diversity included interclade viral recombinants. It is now appreciated that HIV-1 recombinants will be found in geographic areas such as Africa, South America, and Southeast Asia, where multiple HIV-1 subtypes coexist and may account for more than 10% of circulating HIV-1 strains. Molecularly, the genomes of these recombinant viruses resemble patchwork mosaics, with juxtaposed diverse HIV-1 subtype segments, reflecting the multiple crossover events contributing to their generation. Most HIV-1 recombinants have arisen in Africa and a majority contains segments originally derived from clade A viruses. In Thailand, for example, the composition of the predominant circulating strain consists of a clade A gag plus pol gene segment and a clade B env gene. Because the clade B env gene in Thai HIV-1 strains is closely related to the clade E env present in virus isolates from the Central African Republic, it is believed that the original recombination event occurred in Africa, with the subsequent introduction of a descendent virus into Thailand. Interestingly, no full-length HIV-1 subtype E isolate (i.e., with subtype E gag, pol, and env genes) has been reported to date.

The discovery that α and μ chemokine receptors function as coreceptors for virus fusion and entry into susceptible $CD4^+$ cells has led to a revised classification scheme for HIV-1 (FIG. 3). Isolates can now be grouped on the basis of chemokine receptor utilization in fusion assays in which HIV-1 gp120 and $CD4^+$ coreceptor proteins are expressed in separate cells. As indicated in FIG. 3, HIV-1 isolates using the CXCR4 receptor (now designated X4 viruses) are usually T cell line (TCL)-tropic syncytium inducing (SI) strains, whereas those exclusively utilizing the CCR5 receptor (R5 viruses) are predominantly macrophage (M)-tropic and non-syncytium inducing (NSI). The dual-tropic R5/X4 strains, which may comprise the majority of patient isolates and exhibit a continuum of tropic phenotypes, are frequently SI.

Figure 4:
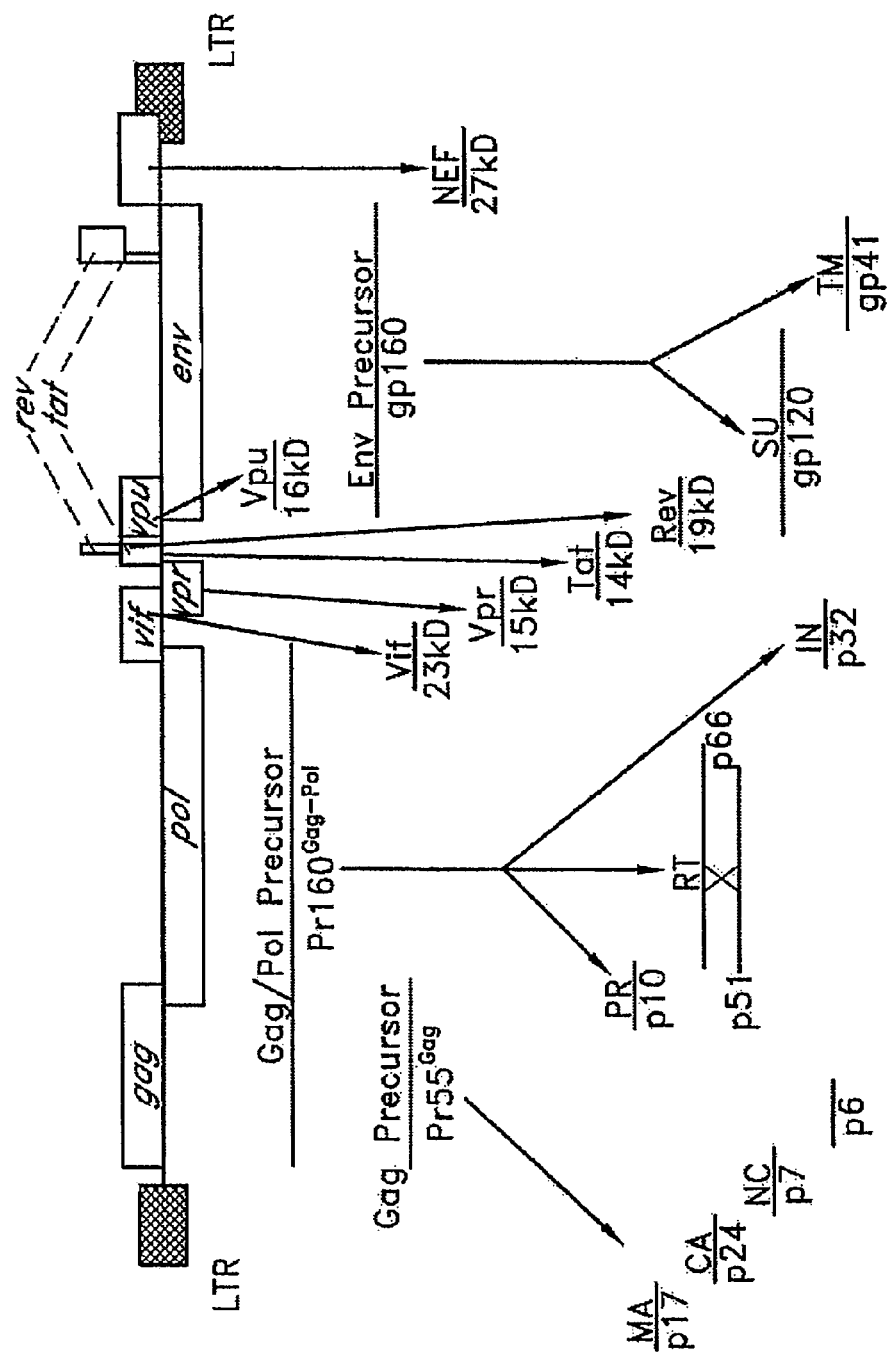
FIG. 4. HIV-encoded proteins. The location of the HIV genes, the sizes of primary translation products (in some cases polyproteins), and the processed mature viral proteins are indicated.

As is the case for all replication-competent retroviruses, the three primary HIV-1 translation products, all encoding structural proteins, are initially synthesized as polyprotein precursors, which are subsequently processed by viral or cellular proteases into mature particle-associated proteins (FIG. 4). The 55-kd Gag precursor $Pr55^{Gag}$ is cleaved into the matrix (MA), capsid (CA), nucleocapsid (NC), and p6 proteins. Autocatalysis of the 160-kd Gag-Pol polyprotein, $Pr160^{Gag-Pol}$, gives rise to the protease (PR), the heterodimeric reverse transcriptase (RT), and the integrase (IN) proteins, whereas proteolytic digestion by a cellular enzyme(s) converts the glycosylated 160-kd Env precursor gp160 to the gp120 surface (SU) and gp41 transmembrane (TM) cleavage products. The reining six HIV-1-encoded proteins (Vif, Vpr, Tat, Rev, Vpu, and Nef) are the primary translation products of spliced mRNAs.

Gag

Figure 5:
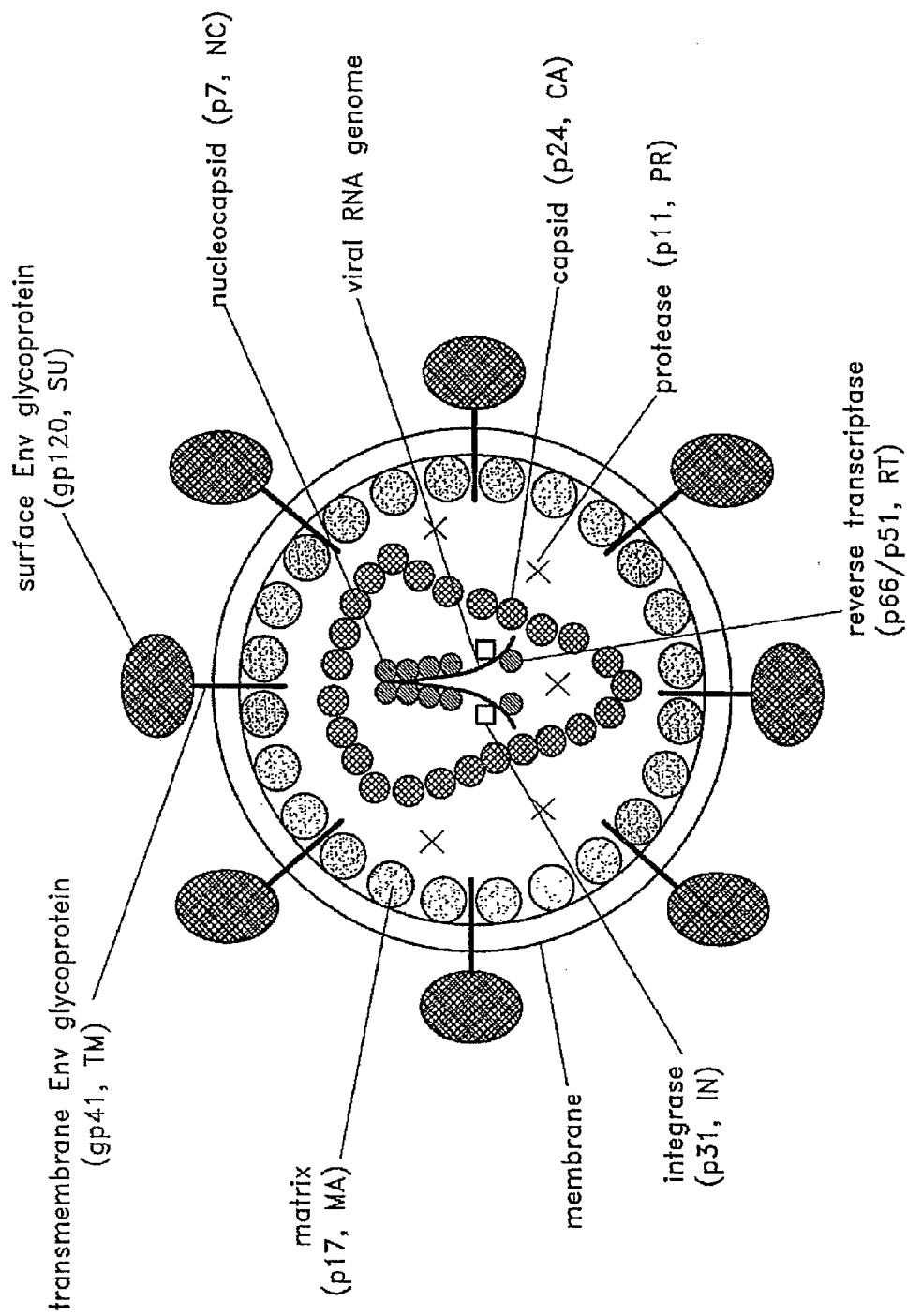
FIG. 5. Schematic representation of a mature HIV-1 virion.

The Gag proteins of HIV, like those of other retroviruses, are necessary and sufficient for the formation of noninfectious, virus-like particles. Retroviral Gag proteins are generally synthesized as polyprotein precursors; the HIV-1 Gag precursor has been named, based on its apparent molecular mass, Pr55$^{Gag}$. As noted previously, the mRNA for Pr55$^{Gag}$ is the unspliced 9.2-kb transcript (FIG. 4) that requires Rev for its expression in the cytoplasm. When the pol ORF is present, the viral protease (PR) cleaves Pr55$^{Gag}$ during or shortly after budding from the call to generate the mature Gag proteins p17 (MA), p24 (CA), p7 (NC), and p6 (see FIG. 4). In the viral, MA is localized immediately inside the lipid bilayer of the viral envelope, CA forms the outer portion of the cone-shaped core structure in the center of the particle, and NC is present in the core in a ribonucleoprotein complex with the viral RNA genome (FIG. 5).

The HIV Pr55$^{Gag}$ precursors oligomerizes following its translation and is targeted to the plasma membrane, where particles of sufficient size and density to be visible by EM are assembled. Formation of virus-like particles by Pr55$^{Gag}$ is a self-assembly process, with critical Gag-Gag interactions taking place between multiple domains along the Gag precursor. The assembly of virus-like particles does not require the participation of genomic RNA (although the presence of nucleic acid appears to be essential), pol-encoded enzymes, or Env glycoproteins, but the production of infectious virions requires the encapsidation of the viral RNA genome and the incorporation of the Env glycoproteins and the Gag-Pol polyprotein precursor Pr160$^{Gag-Pol}$.

Pol

Downstream of gag lies the most highly conserved region of the HIV genome, the pol gene, which encodes three enzymes: PR, RT, and IN (see FIG. 4). RT and IN are required, respectively, for reverse transcription of the viral RNA genome to a double-stranded DNA copy, and for the integration of the viral DNA into the host cell chromosome. PR plays a critical role late in the life cycle by mediating the production of mature, infectious virions. The pol gene products are derived by enzymatic cleavage of a 160-kd Gag-Pol fusion protein, referred to as Pr160$^{Gag-Pol}$. This fusion protein is produced by ribosomal frameshifting during translation of Pr55$^{Gag}$ (see FIG. 4). The frame-shifting mechanism for Gag-Pol expression, also utilized by many other retroviruses, ensures that the pol-derived proteins are expressed at a low level, approximately 5% to 10% that of Gag. Like Pr55$^{Gag}$, the N-terminus of Pr160$^{Gag-Pol}$ is myristylated and targeted to the plasma membrane.

Protease

Early pulse-chase studies performed with avian retroviruses clearly indicated that retroviral Gag proteins are initially synthesized as polyprotein precursors that are cleaved to generate smaller products. Subsequent studies demonstrated that the processing function is provided by a viral rather than a cellular enzyme, and that proteolytic digestion of the Gag and Gag-Pol precursors is essential for virus infectivity. Sequence analysis of retroviral PRs indicated that they are related to cellular "aspartic" proteases such as pepsin and resin. Like these cellular enzymes, retroviral PRs use two apposed Asp residues at the active site to coordinate a water molecule that catalyzes the hydrolysis of a peptide bond in the target protein. Unlike the cellular aspartic proteases, which function as pseudodimers (using two folds within the same molecule to generate the active site), retroviral PRs function as true dimers. X-ray crystallographic data from HIV-1 PR indicate that the two monomers are held together in part by a four-stranded antiparallel β-sheet derived from both N- and C-terminal ends of each monomer. The substrate-binding site is located within a cleft formed between the two monomers. Like their cellular homologs, the HIV PR dimer contains flexible "flaps" that overhang the binding site and may stabilize the substrate within the cleft; the active-site Asp residues lie in the center of the dimer. Interestingly, although some limited amino acid homology is observed surrounding active-site residues, the primary sequences of retroviral PRs are highly divergent, yet their structures are remarkably similar.

Reverse Transcriptase

By definition, retroviruses possess the ability to convert their single-stranded RNA genomes into double-stranded DNA during the early stages of the infection process. The enzyme that catalyzes this reaction is RT, in conjunction with its associated RNaseH activity. Retroviral RTs have three enzymatic activities: (a) RNA-directed DNA polymerization (for minus-strand DNA synthesis), (b) RNaseH activity (for the degradation of the tRNA primer and genomic RNA present in DNA-RNA hybrid intermediates), and (c) DNA-directed DNA polymerization (for second- or plus-strand DNA synthesis).

The mature HIV-1 RT holoenzyme is a heterodimer of 66 and 51 kd subunits. The 51-kd subunit (p51) is derived from the 66-kd (p66) subunit by proteolytic removal of the C-terminal 15-kd RNaseH domain of p66 by PR (see FIG. 4). The crystal structure of HIV-1 RT reveals a highly asymmetric folding in which the orientations of the p66 and p51 subunits differ substantially. The p66 subunit can be visualized as a right hand, with the polymerase active site within the palm, and a deep template-binding cleft formed by the palm, fingers, and thumb subdomains. The polymerase domain is linked to RNaseH by the connection subdomain. The active site, located in the palm, contains three critical Asp residues (110, 185, and 186) in close proximity, and two coordinated Mg$^{2+}$ ions. Mutation of these Asp residues abolishes RT polymerizing activity. The orientation of the three active-site Asp residues is similar to that observed in other DNA polymerases (e.g., the Klenow fragment of *E. coli* DNA polI). The p51 submit appears to be rigid and does not form a polymerizing cleft; Asp 110, 185, and 186 of this subunit are buried within the molecule. Approximately 18 base pairs of the primer-template duplex lie in the nucleic acid binding cleft, stretching from the polymerase active site to the RNaseH domain.

In the RT-primer-template-dNTP structure, the presence of a dideoxynucleotide at the 3' end of the primer allows visualization of the catalytic complex trapped just prior to attack on the incoming dNTP. Comparison with previously obtained structures suggests a model whereby the fingers close in to trap the template and dNTP prior to nucleophilic attack of the 3'-OH of the primer on the incoming dNTP. After the addition of the incoming dNTP to the growing chain, it has been proposed that the fingers adopt a more open configuration, thereby releasing the pyrophosphate and enabling RT to bind the next dNTP. The structure of the HIV-1 RNaseH has also been determined by x-ray crystallography; this domain displays a global folding similar to that of *E. coli* RNaseH.

Integrase

A distinguishing feature of retrovirus replication is the insertion of a DNA copy of the viral genome into the host cell chromosome following reverse transcription. The integrated viral DNA (the provirus) serves as the template for the synthesis of viral RNAs and is maintained as part of the host cell genome for the lifetime of the infected cell.

Retroviral mutants deficient in the ability to integrate generally fail to establish a productive infection.

The integration of viral DNA is catalyzed by integrase, a 32-kd protein generated by PR-mediated cleavage of the C-terminal portion of the HIV-1 Gag-Pol polyprotein (see FIG. 4).

Retroviral IN proteins are composed of three structurally and functionally distinct domains: an N-terminal, zinc-finger-containing domain, a core domain, and a relatively nonconserved C-terminal domain. Because of its low solubility, it has not yet been possible to crystallize the entire 288-amino-acid HIV-1 IN protein. However, the structure of all three domains has been solved independently by x-ray crystallography or NMR methods. The crystal structure of the core domain of the avian sarcoma virus IN has also been determined. The N-terminal domain (residues 1 to 55), whose structure was solved by NMR spectroscopy, is composed of four helices with a zinc coordinated by amino acids His-12, His-16, Cys-40, and Cys-43. The structure of the N-terminal domain is reminiscent of helical DNA binding proteins that contain a so-called helix-turn-helix motif however, in the HIV-1 structure this motif contributes to dimer formation. Initially, poor solubility hampered efforts to solve the structure of the core domain. However, attempts at crystallography were successful when it was observed that a Phe-to-Lys change at IN residue 185 greatly increased solubility without disrupting in vitro catalytic activity. Each monomer of the HIV-1 IN core domain (IN residues 50 to 212) is composed of a five-stranded n-sheet flanked by helices; this structure bears striking resemblance to other polynucleotidyl transferases including RNaseH and the bacteriophage MuA transposase. Three highly conserved residues are found in analogous positions in other polynucleotidyl transferases; in HIV-1 IN these are Asp-64, Asp-116 and Glu-152, the so-called D,D-35-E motif. Mutations at these positions block HIV IN function both in vive and in vitro. The close proximity of these three amino acids in the crystal structure of both avian sarcoma virus and HIV-1 core domains supports the hypothesis that these residues play a central role in catalysis of the polynucleotidyl transfer reaction that is at the heart of the integration process. The C-terminal domain, whose structure has been solved by NMR methods, adopts a five-stranded β-barrel folding topology reminiscent of a Src homology 3 (SH3) domain. Recently, the x-ray structures of SIV and Rous sarcoma virus IN protein fragments encompassing both the core and C-terminal domains have been solved.

Env

The HIV Env glycoproteins play a major role in the virus life cycle. They contain the determinants that interact with the CD4 receptor and coreceptor, and they catalyze the fusion reaction between the lipid bilayer of the viral envelope and the host cell plasma membrane. In addition, the HIV Env glycoproteins contain epitopes that elicit immune responses that are important from both diagnostic and vaccine development perspectives.

Figure 6:
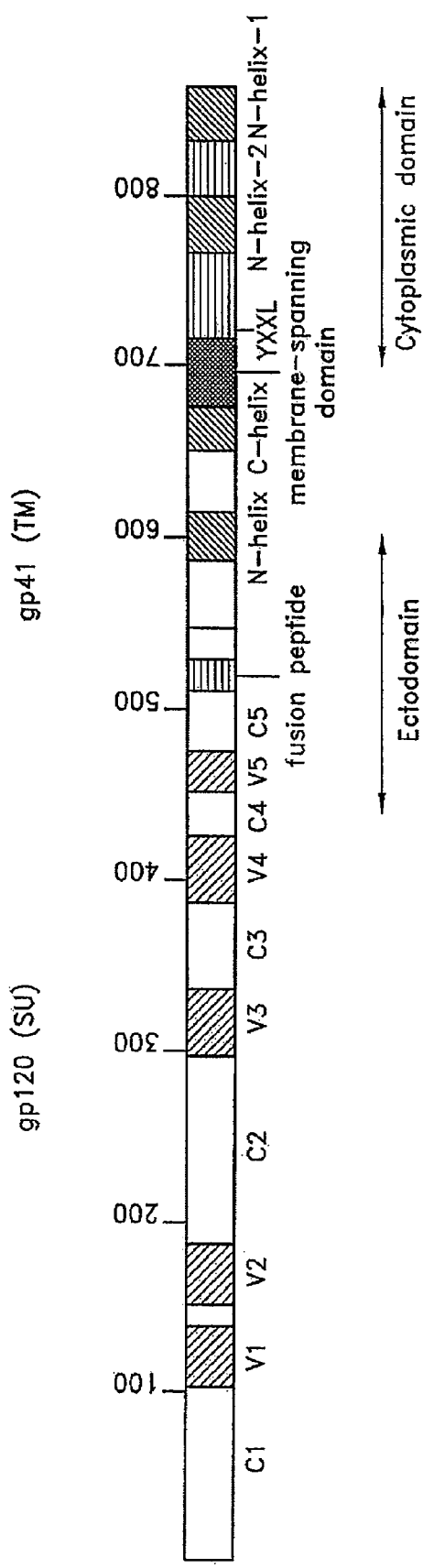
FIG. 6. Linear representation of the HIV-1 Env glycoprotein. The arrow indicates the site of gp160 cleavage to gp120 and gp41. In gp120, cross-hatched areas represent variable domains ($V_1$ to $V_5$) and open boxes depict conserved sequences ($C_1$ to $C_5$). In the gp41 ectodomain, several domains are indicated: the N-terminal fusion peptide, and the two ectodomain helices (N- and C-helix). The membrane-spanning domain is represented by a black box. In the gp41 cytoplasmic domain, the Tyr-X-X-Leu (YXXL) endocytosis motif (SEQ ID NO: 1) and two predicted helical domains (helix-1 and -2) are shown. Amino acid numbers are indicated.

The HIV Env glycoprotein is synthesized from the singly spliced 43-kb Vpu/Env bicistronic mRNA (see FIG. 4); translation occurs an ribosomes associated with the rough endoplasmic reticulum (ER). The 160-kd polyprotein precursor (gp160) is an integral membrane protein that is anchored to cell membranes by a hydrophobic stop-transfer signal in the domain destined to be the mature TM Env glycoprotein, gp41 (FIG. 6). The gp160 is cotranslationally glycosylated, forms disulfide bonds, and undergoes oligomerization in the ER. The predominant oligomeric form appears to be a trimer, although dimers and tetramers are also observed. The gp160 is transported to the Golgi, where, like other retroviral envelope precursor proteins, it is proteolytically cleaved by cellular enzymes to the mature SU glycoprotein gp120 and TM glycoprotein gp41 (see FIG. 6). The cellular enzyme responsible for cleavage of retroviral Env precursors following a highly conserved Lys/Arg-X-Lys/Arg-Arg motif is furin or a furin-like protease, although other enzymes may also catalyze gp160 processing. Cleavage of gp160 is required for Env-induced fusion activity and virus infectivity. Subsequent to gp160 cleavage, gp120 and gp41 form a noncovalent association that is critical for transport of the Env complex from the Golgi to the cell surface. The gp120-gp41 interaction is fairly weak, and a substantial amount of gp120 is shed from the surface of Env-expressing cells.

The HIV Env glycoprotein complex, in particular the SU (gp120) domain, is very heavily glycosylated; approximately half the molecular mass of gp160 is composed of oligosaccharide side chains. During transport of Env from its site of synthesis in the ER to the plasma membrane, many of the side chains are modified by the addition of complex sugars. The numerous oligosaccharide side chains form what could be imagined as a sugar cloud obscuring much of gp120 from host immune recognition. As shown in FIG. 6, gp120 contains interspersed conserved ($C_1$ to $C_5$) and variable ($V_1$ to $V_5$) domains. The Cys residues present in the gp120s of different isolates are highly conserved and form disulfide bonds that link the first four variable regions in large loops.

A primary function of viral Env glycoproteins is to promote a membrane fusion reaction between the lipid bilayers of the viral envelope and host cell membranes. This membrane fusion event enables the viral core to gain entry into the host cell cytoplasm. A number of regions in both gp120 and gp41 have been implicated, directly or indirectly, in Env-mediated membrane fusion. Studies of the $HA_2$ hemagglutinin protein of the orthomyxovixuses and the F protein of the paramyxoviruses indicated that a highly hydrophobic domain at the N-terminus of these proteins, referred to as the fusion peptide, plays a critical role in membrane fusion. Mutational analyses demonstrated that an analogous domain was located at the N-terminus of the HIV-1, HIV-2, and SIV TM glycoproteins (see FIG. 6). Nonhydrophobic substitutions within this region of gp41 greatly reduced or blocked syncytium formation and resulted in the production of noninfectious progeny virions.

C-terminal to the gp41 fusion peptide are two amphipathic helical domains (see FIG. 6) which play a central role in membrane fusion. Mutations in the N-terminal helix (referred to as the N-helix), which contains a Leu zipper-like heptad repeat motif impair infectivity and membrane fusion activity, and peptides derived from these sequences exhibit potent antiviral activity in culture. The structure of the ectodomain of HIV-1 and SIV gp41, the two helical motifs in particular, has been the focus of structural analyses in recent years. Structures were determined by x-ray crystallography or NMR spectroscopy either for fusion proteins containing the helical domains, a mixture of peptides derived from the N- and C-helices, or in the case of the SIV structure, the intact gp41 ectodomain sequence from residue 27 to 149. These studies obtained fundamentally similar trimeric structures, in which the two helical domains pack in an antiparallel fashion to generate a six-helix bundle. The N-helices form a coiled-coil in the center of the bundle, with the C-helices packing into hydrophobic grooves on the outside.

In the steps leading to membrane fusion CD4 binding induces conformation changes in Env that facilitate coreceptor binding. Following the formation of a ternary gp120/CD4/coreceptor complex, gp41 adopts a hypothetical conformation that allows the fusion peptide to insert into the target lipid bilayer. The formation of the gp41 six-helix bundle (which involves antiparallel interactions between the gp41 N- and C-helices) brings the viral and cellular membranes together and membrane fusion takes place.

Furthermore, therapeutically interesting genes according to the present invention also comprise disease related genes, which have a therapeutic effect an proliferative disorder, cancer or metabolic diseases. For example, a therapeutically interesting gene regarding cancer could be a cancer antigen that has the capacity to induce a specific anti-cancer immune reaction.

According to a further embodiment of the present invention, the heterologous nucleic acids sequence comprises at least one marker or selection gene.

Selection genes transduce a particular resistance to a cell, whereby a certain selection method becomes possible. The skilled practitioner is familiar with a variety of selection genes, which can be used in a poxviral system. Among these are, e.g., neomycin resistance gene (NPT) or phosphoribosyl transferase gene (gpt).

Marker genes induce a color reaction in transduced cells, which can be used to identify transduced cells. The skilled practitioner is familiar with a variety of marker genes, which can be used in a poxviral system. Among these are the gene encoding, e.g., β-galactosidase (β-gal), β-glucosidase (β-glu), green fluorescence protein (EGFP) or blue fluorescence protein.

According to still a further embodiment of the present invention the heterologous nucleic acid sequence comprises a spacing sequence, which separates poxviral transcription control element and/or coding sequence in the heterologous nucleic acid sequence from the stop codon and/or the start codon of the adjacent ORFs. This spacer sequence between the stop/start codon of the adjacent ORF and the inserted coding sequence in the heterologous nucleic acid sequence has the advantage to stabilize the inserted heterologous nucleic acid sequence and, thus, any resulting recombinant virus. The size of the spacer sequence is variable as long as the sequence is without its own coding or regulatory function.

According to a further embodiment, the spacer sequence separating the poxviral transcription control element and/or the coding sequence in the heterologous nucleic acid sequence from the stop codon of the adjacent ORF is at least one nucleotide long.

According to another embodiment of the present invention, the spacing sequence separating the poxviral transcription control element and/or the coding sequence in the heterologous nucleic acid sequence from the start codon of the adjacent ORF is at least 30 nucleotides. Particularly, in cases where a typical vaccinia virus promoter element is identified upstream of a start codon the insertion of heterologous nucleic acid sequence may not separate the promoter element from the start codon of the adjacent ORF. A typical vaccinia promoter element can be identified by scanning for e.g., the sequence "TAAAT" for late promoters (Davison & Moss 1989 *J. Mol. Biol.;* 210:771-784) and an A/T rich domain for early promoters. A spacing sequence of about 30 nucleotides is the preferred distance to secure that a poxviral promoter located upstream of the start codon of the ORF is not influenced. Additionally, according to a further preferred embodiment, the distance between the inserted heterologous nucleic acid sequence and the start codon of the adjacent ORF is around 50 nucleotides and more preferably around 100 nucleotides.

According to a further preferred embodiment of the present invention, the spacing sequence comprises an additional poxviral transcription control element which is capable of controlling the transcription of the adjacent ORF.

Thus far, the disclosure has focused on recombinant MVA viruses using ORFs that are adjacent in parental MVA virus. However, the present invention also includes recombinant viruses, and methods of making such viruses, in which heterologous nucleic acid sequences are inserted between adjacent, essential ORFs techniques, wherein the ORFs used for insertion are not adjacent in the parental MVA virus. That is, viruses can be constructed so that ORFs that are adjacent in the recombinant MVA virus are separated by one or more poxvirus ORFs (intervening ORFs) in the parental MVA virus. As used herein, a parental MVA virus is one from which a progeny, recombinant virus is constructed. An example of a parental MVA virus is MVA 1974/NIH Clone 1. Parental viruses can be used to construct recombinant viruses using techniques disclosed herein, such that the intervening ORFs can be removed during the construction process. It is appreciated by those skilled in the poxvirus arts that by using nucleic acid molecules comprising carefully selected poxvirus ORF's, sections of the viral genome between those two ORFs can be deleted through the process of homologous recombination. For example, it can be supposed that two essential ORFs are separated by a one kilobase region of the genome containing a non-essential ORF. A nucleic acid construct can be made in which the two essential ORFs are cloned, for example, into a plasmid such that the two ORFs are adjacent in the nucleic acid construct. Upon introduction of the nucleic acid construct into a poxvirus infected cell (e.g., a parental MVA virus infected cell), the essential ORFs will recombine with the corresponding ORFs in the viral genome of the parental virus. Through further recombination events understood by those skilled in the art, the one kilobase region will be excised from the viral genome, resulting in the two essential ORF becoming adjacent. Thus, one embodiment of the present invention is a recombinant modified vaccinia Ankara (MVA) virus comprising a heterologous nucleic acid sequence located between two adjacent essential ORFs from the MVA virus genome, wherein the recombinant MVA virus lacks non-essential ORFs that are present between the corresponding essential ORFs in the parental MVA virus. Thus the heterologous nucleic acid sequence is flanked by essential ORFs that are non-adjacent in the parental MVA virus. The essential ORF are chosen from pairs of essential ORFs present in the MVA genome that are separated by non-essential ORFs. In one embodiment, the essential ORFs are selected from the group consisting of A50R (MVA163), B1R (MVA167), F10 (MVA-039), F12 (MVA042), F13L (MVA043), F15L (MVA045), F17L (MVA047), E4L (MVA051), E6L (MVA053), E8L (MVA055), E10L (MVA057), I1L (MVA062), I3L (MVA064), I5L (MVA066), J1R (MVA085), J3R (MVA087), D7L (MVA104), D9L (MVA106), A24R (MVA135), and A28R (MVA139). In one embodiment, the two essential ORFs are selected from pairs of essential ORFs in the group of consisting of A50R-B1R (MVA163-MVA167), F10-F12 (MVA039-MVA042), F13L-F15L (MVA043-MVA045), F15L-F17L (MVA045-MVA047), E4L-B6L (MVA051-MVA053), E6L-E8L (MVA053-MVA055), E10L-I1L (MVA057-MVA062), I3L-I5L (MVA064-MVA066), J1R-J3R (MVA085-MVA087), D7L-D9L (MVA104-MVA106), and A24R-A28R (MVA135-MVA139). In one embodiment, the essential ORFs are selected from A50R (MVA163) and B1R (MVA167). In one embodiment, one essential ORF is A50R (MVA163) and the other essential ORF is B1R (MVA167).

As previously discussed, as a result of extensive passage in cell culture, the MVA virus genome contains six major deletions, referred to as Del I, II, II, IV, V and VI. Historically, the region around Del III, which is a deletion of approximately 31,000 nucleotides, has been used for insertion of heterologous nucleic acid sequences. Thus, in one embodiment of the present invention, the non-essential ORFs deleted during construction of the recombinant MVA virus flank the Del III region in the wild-type MVA virus.

As has been described, recombinant MVA viruses can contain additional sequences, such as IGRs and/or heterologous nucleic acid sequences, between the two adjacent, essential ORFs. Such sequences have been described herein. Thus, one embodiment of the present invention is a recombinant modified vaccinia Ankara (MVA) virus comprising a heterologous nucleic acid sequence located between two adjacent essential ORFs from the MVA virus genome, wherein the recombinant MVA virus lacks non-essential ORFs that are present between the corresponding essential ORFs in the parental MVA virus, and wherein the heterologous nucleic acid sequence is inserted into an IGR. The heterologous can contain coding sequences under the control of a transcriptional control element, as has been described elsewhere in the disclosure.

While the inventors have disclosed specific essential ORFs, and sequences thereof; the present invention also comprises recombinant MVA virus, and methods of making such, using portions or variants of the disclosed ORF. For example, while the present invention discloses ORF A50R, and portions thereof; (SEQ ID NO: 1 and SEQ ID NO:14), and ORF B1R, and portions thereof (SEQ ID NO:16 and SEQ ID NO:19), the present invention comprises recombinant MVA viruses comprising variants of these sequences, so long as the variant ORF encodes a protein having essentially the same function as the protein encoded by the corresponding wild-type ORF. Two proteins are considered as having essentially the same function if MVA viruses comprising the respective proteins produce titers that are within about 10%, about 20%, about 30% or about 40% of each other when grown using the same cell line. Thus, one embodiment of the present invention is a recombinant modified vaccinia Ankara (MVA) virus comprising a heterologous nucleic acid sequence located between two adjacent ORFs, wherein the adjacent ORFs comprise a nucleotide sequence at least 90%, at least 95%, at least 97% or at least 99% sequence identity with an essential ORF from MVA. In one embodiment, the adjacent ORFs comprise a nucleotide sequence at least 90%, at least 95%, at least 97% or at least 99% identical to essential ORFs selected from the group consisting of A50R (MVA163), B1R (MVA167), F10 (MVA-039), F12 (MVA042), F13L (MVA043), F15L (MVA045), F17L (MVA047), E4L (MVA051), E6L (MVA053), E8L (MVA055), E10L (MVA057), I1L (MVA062), I3L (MVA064), I5L (MVA066), J1R (MVA085), J3R (MVA087), D7L (MVA104), D9L (MVA106), A24R (MVA135), and A28R (MVA139). In a preferred embodiment, the two adjacent ORFs are not derived from the same essential ORF. In one embodiment, the two adjacent ORFs comprise nucleotide sequences at least 90%, at least 95%, at least 97% or at least 99% identical to pairs of essential ORFs in the group of consisting of A50R-B1R (MVA163-MVA167), F10-F12 (MVA039-MVA042), F13L-F15L (MVA043-MVA045), F15L-F17L (MVA045-MVA047), E4L-E6L (MVA051-MVA053), E6L-E8L (MVA053-MVA055), E10L-I1L (MVA057-MVA062), I3L-I5L (MVA064-MVA066), J1R-J3R (MVA085-MVA087), D7L-D9L (MVA104-MVA106), and A24R-A28R (MVA135-MVA139). In one embodiment one adjacent ORF comprises a nucleotide sequence at least 90%, at least 95%, at least 97% or at least 99% sequence identical with SEQ ID NO:A50R (MVA163) and the second adjacent ORF comprises a nucleotide sequence at least 90%, at least 95%, at least 97% or at least 99% sequence identical to a second essential ORF. In one embodiment one adjacent ORF comprises a nucleotide sequence at least 90%, at least 95%, at least 97% or at least 99% sequence identical with SEQ ID NO:B1R.

The present invention also discloses nucleic add constructs useful for producing recombinant viruses of the present invention. As used herein a nucleic acid construct is a recombinant nucleic acid molecule comprising at least a portion of at least one essential ORF from MVA virus. The nucleic acid construct enables transport of useful nucleic acid sequences to a cell within an environment, such as, but not limited to, an organism, tissue, or cell culture. A nucleic acid construct of the present disclosure is produced by human intervention. The nucleic acid construct can be DNA, RNA or variants thereof. The nucleic acid molecule can be linear DNA, a DNA plasmid, a viral vector, or other vector. In one embodiment, a nucleic acid molecule can be a DNA plasmid. In one embodiment, a nucleic acid molecule can be a DNA plasmid comprising viral components, plasmid components, transcriptional control elements, and any other useful elements know to those skilled in the art that enable nucleic acid molecule delivery and expression. Methods for the general construction of recombinant nucleic acid molecules are well known. See, for example, *Molecular Cloning: a Laboratory Manual*, $3^{rd}$ edition, Sambrook et al. 2001 Cold Spring Harbor Laboratory Press, and *Current Protocols in Molecular Biology*, Ausubel et al. eds., John Wiley & Sons, 1994.

One embodiment of the present invention is an isolated nucleic acid construct comprising: (a) a first nucleic acid sequence derived from, or homologous to, a first essential ORF from a modified vaccinia Ankara (MVA) virus genome; and (b) a second nucleic acid sequence derived from, or homologous to, a second essential ORF from a MVA virus genome; wherein the first and second essential MVA virus ORFs are separated by at least one non-essential ORF in the MVA virus genome, and wherein the first and second nucleic acid sequences are adjacent to each other in the isolated nucleic acid construct, and wherein the first and second nucleic acid sequences comprise at least 25 contiguous nucleotides from the first and second essential MVA ORFs, respectively. Such a nucleic acid construct is useful for constructing recombinant MVA viruses through the process of homologous recombination. Using this process, isolated nucleic acid constructs of the present invention can be used to construct recombinant MVA viruses in which ORFs that are not adjacent in a parental MVA virus (i.e, they are separated by other, non-essential MVA ORFs), are made adjacent in the progeny, recombinant MVA virus. This can be done, for example, by cloning non-adjacent ORFs from a parental MVA virus into a nucleic acid molecule, such as a plasmid, without also cloning the intervening non-essential ORFs. Thus, the no-adjacent ORFs are made adjacent in the nucleic acid construct. As has been described, recombination of such a nucleic acid construct into the MVA viral genome will result in deletion of the intervening non-essential ORFs from the parental MVA virus resulting in a progeny, recombinant MVA virus in which the originally non-adjacent ORFs are adjacent. Thus, in a preferred embodiment, the first and second nucleic acid sequences are derived from, or homologous to, first and second essential MVA ORFs, respectively, that are not adjacent in the parental MVA virus. That is, the first and second essential ORFs are separated by at least one non-essential ORF in the parental MVA virus genome.

As used herein, the phrase derived from refers to the source nucleic acid (i.e., ORF) from which the nucleic acid sequence was obtained. Thus, in this regard the nucleic acid sequence may be identical to all or part of the originating ORF. However, the nucleic acid sequence may also vary in sequence from the originating ORF. Thus, a nucleic acid sequence that is derived from an MVA ORF may or may not be identical in sequence to all, or a portion, of an MVA ORF, so long as the function of the original ORF is maintained in the derived nucleic acid sequence. For example, it is understood in the art that nucleic acid molecules from related species of poxviruses can recombine, even though the sequences of such molecules are not identical. Thus, in one embodiment of the present invention, the first and second nucleic acid sequences have sufficient sequence identity with the essential MVA ORFs from which they area derived to allow homologous recombination between a nucleic acid molecule comprising the first or second nucleic acid sequence, and a nucleic acid molecule comprising the essential MVA ORF from which such sequence was derived. In one embodiment, the first and second nucleic acid sequences are at least 75%, at least 85%, at least 90%, at least 95%, at least 97%, or at least 99% identical to at least a portion of the essential MVA ORF from which they are derived. In one embodiment, the nucleic acid sequence is identical to at least a portion of the essential MVA ORF from which it was derived.

It is also appreciated in the art that small polynucleotide molecules are capable of engaging in the process of homologous recombination. Consequently, nucleic acid sequences present in nucleic acid constructs of the present invention need not comprise the entire sequence of an essential MVA ORF in order for the nucleic acid construct to be able to recombine into the MVA virus genome. In fact, it has been shown that fragments of the poxvirus genome as small as 20 bases in length are capable of engaging in homologous recombination with their respective sequence in the viral genome. Thus, in one embodiment of the present invention, the first and second nucleic acid sequences can comprise 25, 30, 35, 40, 45, 50, 100, 150, 200, 250, or 300 nucleotides from an essential MVA ORF. One embodiment of the present invention is an isolated nucleic acid construct comprising: (a) a first nucleic acid sequence comprising at least 25 contiguous nucleotides from a first essential MVA ORF; and (b) a second nucleic acid sequence comprising at least 25 contiguous nucleotides from a second essential MVA ORF; wherein the first and second essential MVA virus ORFs are separated by at least one non-essential ORF in the MVA virus genome, and wherein the first and second nucleic acid sequences are adjacent to each other in the isolated nucleic acid construct. In one embodiment, the first nucleic acid sequences comprise 25 contiguous nucleotides from an essential ORF selected from the group consisting of A50R (MVA163), B1R (MVA167), F10 (MVA-039), F12 (MVA042), F13L (MVA043), F15L (MVA045), F17L (MVA047), E4L (MVA051), E6L (MVA053), E8L (MVA055), E10L (MVA057), I1L (MVA062), I3L (MVA064), I5L (MVA066), J1R (MVA085), J3R (MVA087), D7L (MVA104), D9L (MVA106), A24R (MVA135), and A28R (MVA139). In one embodiment, the second nucleic acid sequences comprise 25 contiguous nucleotides from an essential ORF selected from the group consisting of A50R (MVA163), B1R (MVA167), F10 (MVA-039), F12 (MVA042), F13L (MVA043), F15L (MVA045), F17L (MVA047), E4L (MVA051), E6L (MVA053), E8L (MVA055), E10L (MVA057), I1L (MVA062), I3L (MVA064), I5L (MVA066), J1R (MVA085), J3R (MVA087), D7L (MVA104), D9L (MVA106), A24R (MVA135), and A28R (MVA139). In one embodiment, the first nucleic acid sequence comprises at least 25 contiguous nucleotides from SEQ ID NO: 11 or SEQ ID NO:14, and the second nucleic add sequence comprises at least 25 contiguous nucleotides from SEQ ID NO:16 or SEQ ID NO:19.

Nucleic acid constructs of the present invention are used to deliver heterologous nucleic acid sequences into the genome of MVA virus. Thus, one embodiment, a nucleic acid construct of the present invention comprises a heterologous nucleic acid molecule between the first and second nucleic acid sequences. Exemplary heterologous nucleic acid sequences have been described elsewhere in the disclosure. Any heterologous nucleic add sequence disclosed herein is suitable for inclusion in a nucleic acid construct of the present invention.

Because nucleic acid constructs of the present invention can recombine with the genome of a parental MVA virus, they can be used to insert heterologous nucleic acid sequences into the viral genome. Thus, in one embodiment of the present invention a nucleic acid contrast of the present invention contains an intergenic region between the first and second nucleic acid sequences. The intergenic region can comprise such things as transcriptional control elements, restriction sites and non-vaccinia open reading frames. Thus, the intergenic region can be used to insert heterologous nucleic acid sequences comprising genes under the control of a transcriptional control element. Upon recombination of the nucleic acid construct with the MVA virus genome, the heterologous nucleic acid sequence will be inserted into the MVA viral genome between the essential ORFs corresponding to the two adjacent, essential ORFs flanking the nucleic acid sequence in the nucleic acid construct. The resulting MVA virus will be a recombinant MVA virus containing the heterologous nucleic acid sequence stably integrated into the MVA virus genome.

In one embodiment, a nucleic acid construct of the present invention comprises complete or partial fragment of an IGR sequence located between the two adjacent ORFs of the viral genome. Preferably, the nucleic acid construct comprises inserted into said IGR-derived sequence at least one cloning site for the insertion of an heterologous DNA sequence of interest and, preferably, for the insertion of a poxviral transcription control element operatively linked to said heterologous DNA sequence. Optionally, the nucleic acid construct comprises a reporter- and/or selection gene cassette. The nucleic acid construct preferably also comprises sequences of the two adjacent ORFs flanking said complete or partial fragment of the IGR sequence.

Some IGRs have been identified which do not include nucleotide sequences. In these cases, the plasmid vector comprises DNA sequences of the IGR flanking sequences, i.e., DNA sequences of the two adjacent ORFs. Preferably, the cloning site for the insertion of the heterologous DNA sequence is inserted into the IGR. The DNA of the IGR flanking sequences is used to direct the insertion of exogenous DNA sequences into the corresponding IGR in the MVA genome. Such a plasmid vector may additionally include a complete or partial fragment of an IGR sequence which comprises the cloning site for the insertion of the heterologous DNA sequence and, optionally, of the, reporter- and/or selection gone cassette.

One embodiment of the present invention is a method to produce a stable, recombinant modified vaccinia Ankara virus. Such a method makes use of the nucleic acid constructs disclosed herein. Thus, the method comprises first obtaining a nucleic acid construct comprising a heterologous nucleic acid sequence located between, or flanked by, two adjacent essential open reading frames (ORFs) of the MVA virus genome, wherein the MVA virus is lacking nonessential ORFS, or ORF fragments, that are present between the corresponding two essential ORFS in the parental MVA virus. For example, to obtain an appropriate nucleic acid construct, nucleic acid sequences from essential MVA ORFs can be isolated and cloned into a standard cloning vector, such as pBluescript (Stratagene), so that they flank the heterologous DNA to be inserted into the MVA genome. This construct can then be introduced into a cell using methods know to those in the art (e.g., transfection). The call containing the nucleic acid construct is then infected with a MVA virus and cultured under conditions suitable to allow homologous recombination between the nucleic acid construct and the MVA virus genome. At the appropriate time the cells are then harvested and the recombinant MVA virus isolated. The resultant virus will be a stable, recombinant MVA virus. Such a virus may also be called a derivative virus. It will be appreciated that the order of the steps of introducing the nucleic acid construct into the cell, and infecting the cell can be reversed, or that these two steps may happen simultaneously.

General methods to introduce heterologous nucleic acid sequences in a nucleic acid construct into an MVA genome and methods to obtain recombinant MVA are well known to the person skilled in the art and, additionally, can be deduced can be deduced from *Molecular Cloning, A Laboratory Manual*, Second Edition, J. Sambrook, E. F. Fritsch and T. Maniatis, Cold Spring Harbor Laboratory Press, 1989 and *Current Protocols in Molecular Biology*, John Wiley and Son Inc. 1998, Chapter 16, section IV, "Expression of proteins in mammalian cells using vaccinia viral vectors".

The DNA sequences according to the invention can be used to identify or isolate the MVA or its derivatives according to the invention and cells or individuals infected with an MVA according to the present invention. The DNA sequences are, e.g., used to generate PCR-primers, hybridization probes or are used in array technologies.

The term derivative virus, and the like, according to the present invention refers to progeny viruses showing the same characteristic features as the parent virus but showing differences in one or more parts of its genome. The term "derivative of MVA" describes a virus, which has the sane functional characteristics compared to MVA. For example, a derivative of MVA 1974/NIH Clone 1 has the characteristic features of MVA 1974/NIH Clone 1. One of these characteristics of MVA 1974/NIH Clone 1 or derivatives thereof is its attenuation and severe restriction in host range.

The recombinant MVA according to the present invention is useful as a medicament or vaccine. Thus, one embodiment of the present invention is a method to protect an individual from a disease using a recombinant MVA virus of the present invention.

A recombinant MVA virus of the present invention can also be used for the introduction of the exogenous coding sequence into a target cell, said sequence being either homologous or heterologous to the genome of the target cell.

The introduction of an exogenous coding sequence into a target cell may be done in vitro to produce proteins, polypeptides, peptides, antigens or antigenic epitopes. This method comprises the infection of a host cell with the recombinant MVA according to the invention, cultivation of the infected host cell under suitable conditions, and isolation and/or enrichment of the polypeptide, peptide, protein, antigen, epitope and/or virus produced by said host cell.

Furthermore, the method for introduction of one or more homologous or one or more heterologous sequence into cells may be applied for in vitro and in vivo therapy. For in vitro therapy, isolated cells that have been previously (ax vivo) infected with the recombinant MVA according to the invention are administered to the living animal body for affecting, preferably inducing an immune response. For in vivo therapy, the recombinant poxvirus according to the invention is directly administered to the living animal body for affecting, preferably inducing an immune response. In this case, the cells surrounding the site of inoculation, but also cells where the virus is transported to via, e.g., the blood stream, are directly infected in vivo by the recombinant MVA according to the invention. After infection, these cells synthesize the proteins, peptides or antigenic epitopes of the therapeutic genes, which are encoded by the exogenous coding sequences and, subsequently, present them or parts thereof on the cellular surface. Specialized cells of the immune system recognize the presentation of such heterologous proteins, peptides or epitopes and launch a specific immune response.

Since the MVA is highly growth restricted and, thus, highly attenuated, it is useful for the treatment of a wide range of mammals including humans, including immune-compromised animals or humans. The present invention also provides pharmaceutical compositions and vaccines for inducing an immune response in a living animal body, including a human.

The pharmaceutical composition may generally include one or more pharmaceutical acceptable and/or approved carriers, additives, antibiotics, preservatives, adjuvants, diluents and/or stabilizers. Such auxiliary substances can be water, saline, glyceol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the recombinant poxvirus according to the invention is converted into a physiologically acceptable form. This can be done based on the experience in the preparation of poxvirus vaccines used for vaccination against smallpox (as described by Stickl, H. et al. 1974 *Dtsch Med Wochenschr.* 99:2386-2392). For example, the purified virus is stored at −80° C. with a titer of 5×10E8 $TCID_{50}$/ml formulated in about 10 mM Tris, 140 mM NaCl pH 7.4. For the preparation of vaccine shots, e.g., 10E2-10E8 particles of the virus are lyophilized in 100 ml of phosphate buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in viva administration. The glass ampoule is then sealed and can be stored between 4° C. and room temperature for several months. However, as long as no need exists the ampoule is stored preferably at temperatures below −20° C.

For vaccination or therapy the lyophilisate can be dissolved in 0.1 to 0.5 ml of an aqueous solution, preferably physiological saline or Tris buffer, and administered either systemically or locally, i.e., parenterally, subcutaneous, intramuscularly, by scarification or any other path of administration know to the skilled practitioner. The mode of administration, the dose and the number of administrations can be optimized by those skilled in the art in a known manner. However, most commonly a patient is vaccinated with a second shot about one month to six weeks after the first vaccination shot.

One embodiment of the present invention is a method to generate an immune response against antigen. Such a response can be a CD8$^+$ T cell immune response or an antibody response. More particularly, the present invention relates to "prime and boost" immunization regimes in which the immune response induced by administration of a priming composition is boosted by administration of a boosting composition. The present invention is based on prior experimental demonstration that effective boosting can be achieved using modified vaccinia Ankara (MVA) vectors, following priming with any of a variety of different types of priming compositions including recombinant MVA itself.

A major protective component of the immune response against a number of pathogens is mediated by T lymphocytes of the CD8$^+$ type, also known as cytotoxic T lymphocytes (CTL). An important function of CD8$^+$ cells is secretion of gamma interferon (IFNγ), and this provides a measure of CD8$^+$ T cell immune response. A second component of the immune response is antibody directed to the proteins of the pathogen.

The present invention employs MVA which, as prior experiments show, has been found to be an effective means for providing a boost to a CD8$^+$ T cell immune response primed to antigen using any of a variety of different priming compositions and also eliciting an antibody response.

Notably, prior experimental work demonstrates that use of predecessors of the present invention allows for recombinant MVA virus expressing an HIV antigen to boost a CD8$^+$ T cell immune response primed by a DNA vaccine and also eliciting an antibody response. The MVA may be found to induce a CD8$^+$ T cell response after immunization. Recombinant MVA may also be shown to prime an immune response that is boosted by one or more inoculations of recombinant MVA.

Non-human primates immunized with plasmid DNA and boosted with the MVA were effectively protected against intramucosal challenge with live virus (Amara et al 2001 Science 292:69-74). Advantageously, the inventors contemplate that a vaccination regime using intradermal, intramuscular or mucosal immunization for both prime and boost can be employed, constituting a general immunization regime suitable for inducing CD8$^+$ T cells and also eliciting an antibody response, e.g., in humans.

The present invention in various aspects and embodiments employs an MVA vector encoding an HIV antigen for boosting a CD8$^+$ T cell immune response to the antigen primed by previous administration of nucleic acid encoding the antigen and also eliciting an antibody response.

A general aspect of the present invention provides for the use of an MVA vector for boosting a CD8$^+$ T cell immune response to an HIV antigen and also eliciting an antibody response.

One aspect of the present invention provides a method of boosting a CD8$^+$ T cell immune response to an HIV antigen in an individual, and also eliciting an antibody response, the method including provision in the individual of an MVA vector including nucleic acid encoding the antigen operably linked to regulatory sequences for production of antigen in the individual by expression from the nucleic acid, whereby a CD8$^+$ T cell immune response to the antigen previously primed in the individual is boosted.

An immune response to an HIV antigen may be primed by immunization with plasmid DNA or by infection with an infectious agent.

A further aspect of the invention provides a method of inducing a CD8$^+$ T cell immune response to an HIV antigen in an individual, and also eliciting an antibody response, the method comprising administering to the individual a priming composition comprising nucleic acid encoding the antigen and then administering a boosting composition which comprises an MVA vector including nucleic acid encoding the antigen operably linked to regulatory sequences for production of antigen in the individual by expression from the nucleic acid.

A further aspect provides for use of an MVA vector, as disclosed, in the manufacture of a medicament for administration to a mammal to boost a CD8$^+$ T cell immune response to an HIV antigen, and also eliciting an antibody response. Such a medicament is generally for administration following prior administration of a priming composition comprising nucleic acid encoding the antigen.

The priming composition may comprise DNA encoding the antigen, such DNA preferably being in the form of a circular plasmid that is not capable of replicating in mammalian cells. Any selectable marker should not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with a boosting composition, or first and second boosting compositions, the first and second boosting compositions being the same or different from one another. Still further boosting compositions may be employed without departing from the present invention. In one embodiment, a triple immunization regime employs DNA, then adenovirus as a first boosting composition, then MVA as a second boosting composition, optionally followed by a further (third) boosting composition or subsequent boosting administration of one or other or both of the same or different vectors. Another option is DNA then MVA then adenovirus, optionally followed by subsequent boosting administration of one or other or both of the same or different vectors.

The antigen to be encoded in respective priming and boosting compositions (however many boosting compositions are employed) need not be identical, but should share at least one CD8$^+$ T cell epitope. The antigen may correspond to a complete antigen, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

An HIV antigen of the invention to be encoded by a recombinant MVA virus includes polypeptides having immunogenic activity elicited by an amino acid sequence of an HIV Env, Gag. Pol, Vif Vpr, Tat, Rev, Vpu, or Nef amino acid sequence as at least one CD8⁺ T cell epitope. This amino acid sequence substantially corresponds to at least one 10-900 amino acid fragment and/or consensus sequence of a known HIV Env or Pol; or at least one 10-450 amino acid fragment and/or consensus sequence of a known HIV Gag; or at least one 10-100 amino acid fragment and/or consensus sequence of a known HIV Vif, Vpr, Tat, Rev, Vpu, or Nef.

Although a full length Env precursor sequence is presented for use in the present invention, Env is optionally deleted of subsequences. For example, regions of the gp120 surface and gp41 transmembrane cleavage products can be deleted.

Although a full length Gag precursor sequence is presented for use in the present invention, Gag is optionally deleted of subsequences. For example, regions of the matrix protein (p17), regions of the capsid protein (p24), regions of the nucleocapsid protein (p7), and regions of p6 (the C-terminal peptide of the Gag polyprotein) can be deleted.

Although a full length Pol precursor sequence is presented for use in the present invention, Pol is optionally deleted of subsequences. For example, regions of the protease protein (p10), regions of the reverse transcriptase protein (p66/p51), and regions of the integrase protein (p32) can be deleted.

Such an HIV Env, Gag, or Pol can have overall identity of at least 50% to a known Env, Gag, or Pol protein amino acid sequence, such as 50-99% identity, or any range or value therein, while eliciting an immunogenic response against at least one strain of an HIV.

Percent identity can be determined, for example, by comparing sequence information using the GAP computer program, version 6.0, available from the University of Wisconsin Genetics Computer Group (UWGCG). The GAP program utilizes the alignment method of Needleman and Wunsch (*J Mol Biol* 1970 48:443), as revised by Smith and Waterman (*Adv Appl Math* 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (*Nucl Acids Res* 1986 14:6745), as described by Schwartz and Dayhoff (eds., *Atlas of Protein Sequence and Structure*, National Biomedical Research Foundation, Washington, D.C. 1979, pp. 353-358); (2) a penalty of 3.0 for each gap and an additional 0.10 penalty for each symbol in each gap; and (3) no penalty for end gaps.

In a preferred embodiment, an Env of the present invention is a variant form of at least one HIV envelope protein. Preferably, the Env is composed of gp120 and the membrane-spanning and ectodomain of gp41 but lacks part or all of the cytoplasmic domain of gp41.

Known HIV sequences are readily available from commercial and institutional HIV sequence databases, such as GENBANK, or as published compilations, such as Myers et al. eds., *Human Retroviruses and AIDS, A Compilation and Analysis of Nucleic Acid and Amino Acid Sequences*, Vol. I and II, Theoretical Biology and Biophysics, Los Alamos, N. Mex. (1993), or on the world wide web at hiv-web.lanl.gov/.

Substitutions or insertions of an HIV Env, Gag, or Pol to obtain an additional HIV Env, Gag, or Pol, encoded by a nucleic acid for use in a recombinant MVA virus of the present invention, can include substitutions or insertions of at least one amino acid residue (e.g., 1-25 amino acids). Alternatively, at least one amino acid (e.g., 1-25 amino acids) can be deleted from an HIV Env, Gag, or Pol sequence. Preferably, such substitutions, insertions or deletions are identified based on safety features, expression levels, immunogenicity and compatibility with high replication rates of MVA.

Amino acid sequence variations in an HIV Env, Gag, or Pol of the present invention can be prepared e.g., by mutations in the DNA. Such HIV Env, Gag, or Pol include, for example, deletions, insertions or substitutions of nucleotides coding for different amino acid residues within the amino acid sequence. Obviously, mutations that will be made in nucleic acid encoding an HIV Env, Gag, or Pol must not place the sequence out of reading frame and preferably will not create complementary domains that could produce secondary mRNA structures.

HIV Env, Gag, or Pol-encoding nucleic acid of the present invention can also be prepared by amplification or site-directed mutagenesis of nucleotides in DNA or RNA encoding an HIV Env, Gag, or Pol and thereafter synthesizing or reverse transcribing the encoding DNA to produce DNA or RNA encoding an HIV Env, Gag, or Pol, based on the teaching and guidance presented herein.

Recombinant MVA viruses expressing HIV Env, Gag, or Pol of the present invention, include a finite set of HIV Env, Gag, or Pol-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., 1978 *Principles of Protein Structure*, Springer-Verlag, New York, N.Y., and Creighton, T. E., 1983 *Proteins: Structure and Molecular Properties*, W. H. Freeman & Co., San Francisco, Calif. For a presentation of nucleotide sequence substitutions, such as codon preferences, see Ausubel et al. eds. *Current Protocols in Molecular Biology*, Greene Publishing Assoc., New York, N.Y. 1994 at §§A.1.1-A.1.24, and Sambrook, J. et al. 1989 *Molecular Cloning: A Laboratory Manual*, Second Edition, Cold Spring Harbor Laboratory Press, Cold Spring Harbor, N.Y. at Appendices C and D.

Thus, one of ordinary skill in the art, given the teachings and guidance presented herein, will know how to substitute other amino acid residues in other positions of an HIV env, gag, or pol DNA or RNA to obtain alternative HIV Env, Gag, or Pol, including substitutional, deletional or insertional variants.

Within the MVA vector, regulatory sequences for expression of the encoded antigen will include a promoter. By "promoter" is meant a sequence of nucleotides from which transcription may be initiated of DNA operably linked downstream (i.e., in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, marker genes and other sequences may be included as appropriate, in accordance with the knowledge and practice of the ordinary person skilled in the art: see, for example, Moss, B. (2001). Poxviridae: the viruses and their replication. In Fields Virology, D. M. Knipe, and P. M. Howley, eds. (Philadelphia, Lippincott Williams & Wilkins), pp. 2849-2883. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, 1998 Ausubel et al. eds., John Wiley & Sons.

Promoters for use in aspects and embodiments of the present invention may be compatible with poxvirus expression systems and include natural, modified and synthetic sequences.

Either or both of the priming and boosting compositions may include an adjuvant, such as granulocyte macrophage-colony stimulating factor (GM-CSF) or encoding nucleic acid therefor.

Administration of the boosting composition is generally about 1 to 6 months after administration of the priming composition, preferably about 1 to 3 months.

Preferably, administration of priming composition, boosting composition, or both priming and boosting compositions, is intradermal, intramuscular or mucosal immunization.

Administration of MVA vaccines may be achieved by using a needle to inject a suspension of the virus. An alternative is the use of a needleless injection device to administer a virus suspension (using. e.g., Biojector™ needleless injector) or a resuspended freeze-dried powder containing the vaccine, providing for manufacturing individually prepared doses that do not need cold storage. This would be a great advantage for a vaccine that is needed in rural areas of Africa.

MVA is a virus with an excellent safety record in human immunizations. The generation of recombinant viruses can be accomplished simply, and they can be manufactured reproducibly in large quantities. Intradermal, intramuscular or mucosal administration of recombinant MVA virus is therefore highly suitable for prophylactic or therapeutic vaccination of humans against AIDS which can be controlled by a $CD8^+$ T cell response.

The individual may have AIDS such that delivery of the antigen and generation of a $CD8^+$ T cell immune response to the antigen is of benefit or has a therapeutically beneficial effect.

Most likely, administration will have prophylactic aim to generate an immune response against HIV or AIDS before infection or development of symptoms.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, nasal, intramuscular, intraperitoneal routes.

As noted, administration is preferably intradermal, intramuscular or mucosal.

Physiological saline solution, dextrose or other saccharide solution or glycols such as ethylene glycol, propylene glycol or polyethylene glycol may be included.

For intravenous, cutaneous, subcutaneous, intramuscular or mucosal injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included as required.

A slow-release formulation may be employed.

Following production of MVA particles and optional formulation of such particles into compositions, the particles may be administered to an individual, particularly human or other primate. Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16th edition, 1980, Osol, A. (ed.).

In one preferred regimen, DNA is administered at a dose of 300 μg to 3 mg/injection, followed by MVA at a dose of $10^6$ to $10^9$ infectious virus particles/injection.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against HIV or AIDS.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1

The following Example demonstrates a shuttle plasmid, recombinant MVA/HIV1 clinical vaccine construct and mechanism for retention of intact foreign gene inserts in recombinant MVA by codon alteration of the foreign gone and insertion of the foreign gene between two vaccinia virus essential genes. The disclosure provides mechanisms for.

retention of intact foreign genes by inserting than between two vaccinia virus genes that are essential for MVA replication. Deletion of the foreign gone can provide a significant growth advantage for the recombinant MVA allowing it to compete with MVA containing the intact foreign gene upon repeated passage. However, most deletions of a foreign gene include loss of some part of the flanking vaccinia virus DNA. If that vaccinia virus DNA is essential, then those viruses with deletions will not replicate and compete with the MVA containing the intact foreign gene. This methodology will be useful in production of recombinant vaccinia viruses that must be amplified to large scale such as for use in clinical trials, and stabilizing foreign gene inserts by alteration of specific "hot spots" that otherwise readily undergo mutation after repeated passage of the recombinant virus. This methodology is useful in production of recombinant viruses that must be amplified to large scale such as for use in clinical trials.

And describes:

the shuttle plasmid, pLW-73, used for insertion of a foreign gene between 2 essential vaccinia virus genes; and the recombinant MVA/HIV-1 clinical vaccine construct MVA/UGD4d, a material that embodies use of these two mechanisms.

Generation of Stable Recombinant MVA Viruses

Modified vaccinia virus Ankara (MVA) recombinants expressing env and gagpol genes from HIV-1 isolates from different geographical locations were constructed. The foreign genes were inserted into 2 sites, Deletion II and Deletion III of MVA. The stability of these genes after repeated passage of recombinant MVA in tissue culture has proven to be variable. The inventors demonstrated that the instability was due to either deletion of the entire foreign gene and some flanking DNA or specific point mutations resulting in propagation of progeny virions that have a growth advantage because they do not express the foreign gene. Here the inventors describe two novel methods of retaining the intact foreign gene recombinant MVA. First, the inventors constructed a transfer vector that directs insertion of a foreign gene between two essential vaccinia virus genes in the conserved central region of the genome. Use of this site for insertion of genes prevents the outgrowth of variants containing large deletions that include the essential vaccinia virus DNA. In addition, this plasmid can be used for insertion of additional genes into recombinant viruses. Second, analysis of isolates with point mutations revealed certain "hot spots" with a propensity for insertion or deletion of a single base that causes premature termination during translation. The inventors showed that generation of silent mutations in these sites resulted in stabilization of the inserted gene.

I. Novel Transfer Vector Construction and Application
Construction of Novel Transfer Vector, pLW-73

1. The central region of the MVA genome, K7R-A24R, was examined for 1) pairs of genes conserved in the poxvirus family or chordopoxvirus subfamily and 2) genes that are in opposite orientation such that their 3' ends are in close proximity, thereby providing an insertion site that would not disrupt a vaccinia promoter. The site chosen as the new insertion site was between two essential genes, I8R and G1L.

2. The left flank of the new vector was constructed in the following way Plasmid LAS-1 was cut with restriction enzymes EcoRI and XhoI to remove the del III MVA flank, GFP, and direct repeat of MVA flank. This insert was cut with AscI and SacI and the GFP fragment was isolated. Five hundred thirty one base pairs at the end of the I8R gene (including the TAA stop codon) was PCR amplified with EcoRI and AscI restriction sites on the ends of the PCR product. PCR amplification of 229 base pairs of the direct repeat (from the end of the I8R gene including the TAA stop codon) was performed with oligonucleotides containing SacI and XhoI restriction sites. All four pieces of DNA, 1) the vector backbone with EcoRI and Xho I ends, 2) new left flank containing end of I8R with EcoRI and AscI ends, 3) GFP with AcsI and SacI ends and the 4) direct repeat of the I8R flank with SacI and XhoI ends were ligated together to make plasmid pLW-72.

Figure 7:
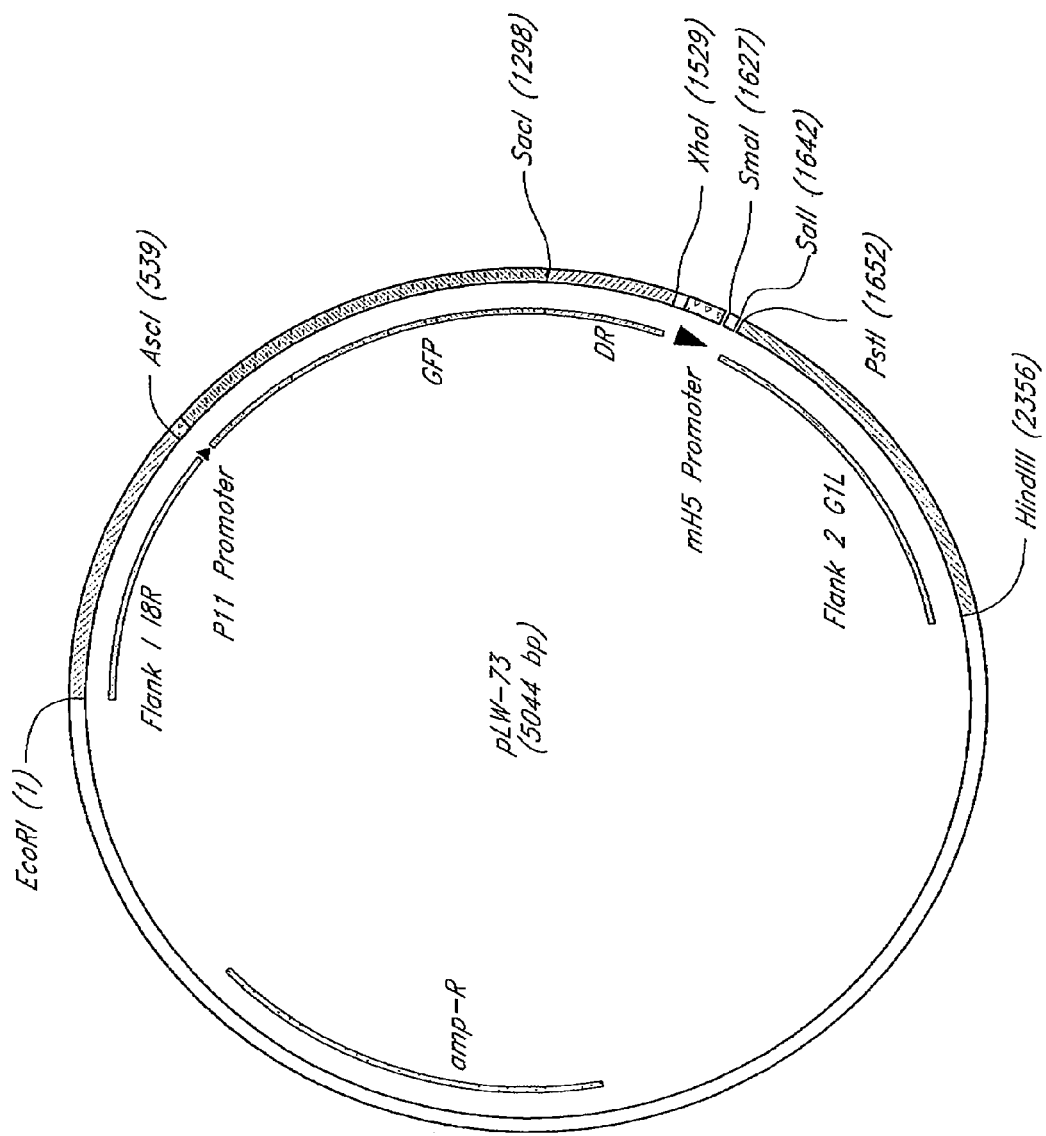
FIG. 7. pLW-73 nucleic acid construct (SEQ ID NO:2 and 3).

3. The right flank was made as follows: pLW-72 was cut with restriction enzymes PstI and HindIII to release del III flank of the MVA in the plasmid. Seven hundred and two base pairs at the end of the G1L gene was PCR amplified with PstI and HindIII restriction enzyme sites on the ends and ligated into the pLW-72 vector to make pLW-73 (FIG. 7). The sequence of pLW-73 is given in FIG. 8.

4. The salient features of pLW-73 are: 1) the vector was designed for insertion of foreign genes between essential genes in MVA genome. The left flank consists of end of I8R gene and right flank consists of end of G1L gene. 2) the GFP gene is included for easy initial selection of recombinant virus 3) the GFP is flanked by direct repeats of the I8R gene which allows for transient expression of GFP as the GFP will be lost upon repeated passage of the recombinant virus. Referring to WO 2004/087201, features 2 and 3 were also contained in earlier plasmids used for making MVA/HIV recombinants, pLAS-1 and pLAS-2.

Application of pLW-73

1. The any gene from the clade B ADA isolate of HIV-1 was cloned into pLW-73 and a recombinant MVA virus was made. DNA sequencing confirmed the location and integrity of the envy gene.

2. A recombinant MVA virus expressing the Ugandan clade D (isolate AO7412) env gene (FIG. 9) in the Deletion II site of MVA proved to be unstable, i.e., after repeated serial passage in culture, the gene was deleted from a significant portion of the virus progeny. The same gene was then cloned into pLW-73 and a recombinant MVA virus was made and characterized. The env gene insert was stable after repeated serial passage (8×) in culture i.e., no deletions of the inserted gene or the MVA flanking region were found. In addition, no other mutations arose when the gene was inserted into this site.

II. Point Mutation of "Hot Spots"

Analysis of Point Mutations

A recombinant MVA virus expressing the Ugandan Clade D (isolate AO3349) gagpol gene in the Deletion III site of MVA proved to be unstable. The major genetic alteration was the generation of single point mutations in runs of 4-6 G or C residues (Table 3). In addition, similar point mutations were found in non-staining plaques from similar recombinant viruses expressing the gagpol genes from a Kenyan clade A isolate and a Tanzanian clade C isolate of HIV-1.

Mutagenesis of Hot Spots and Analysis of Stability in Recombinant Virus

Figure 10:
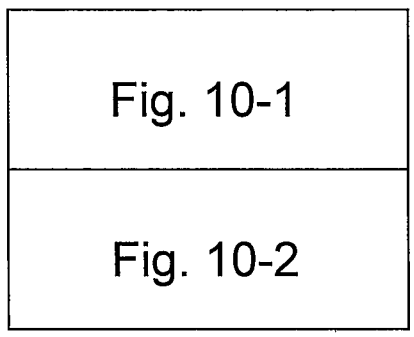
FIG. 10. Codon altered nucleotide sequence encoding Ugandan clade D gagpol protein (isolate AO3349) (SEQ ID NO: 5).

Using site-directed mutagenesis, silent mutations were made in 6 such regions of the gag gene from the Ugandan HIV-1 isolate. This altered gene, UGD 4d gagpol orf (FIG. 10), was cloned into pLAS-1 and recombined into the same Deletion III site of MVA as was done in construction of the unstable virus. After repeated serial passage (8×) in culture, no non-expressing plaques were found. DNA sequencing of the passage 8 virus stock verified that the integrity of the gagpol gene was maintained.

III. Double Recombinant Construction

MVA/UGD4d Virus

MVA/UGD4d virus, a recombinant virus that expresses the Ugandan subtype D AO7412 envelope and the AO3349 gagpol, was constructed in the following way: The envelope and gagpol genes were inserted into MVA 1974/NIH Clone 1 by homologous recombination utilizing shuttle plasmids pLW-73 and pLAS-1, respectively. MVA/UGD4d was isolated by 6 rounds of plaque purification in chicken embryo fibroblast cells and subsequently amplified and characterized.

Summary

1. A plasmid transfer vector was constructed that directs recombination of a foreign gene between two essential genes, I8R and G1L, in the conserved central region of the MVA genome. The use of this site was shown to inhibit selection of mutant viruses with deletions of inserted gene/MVA flanks.

2. Highly mutable runs of G and C residues were altered by site-directed mutagenesis and silent mutations in the coding sequence were generated. This change was shown to stabilize the gene when inserted into Deletion III of MVA.

3. Utilizing these two methods above, UGD4d double MVA recombinant that stably expresses both the env and gagpol of Ugandan Clade D was constructed.

Example 2

Recombinant MVAs expressing HIV-1 my and gagpol genes from many different isolates have been made. The stability of inserted genes after repeated passage in tissue culture has proven to be variable. Here the inventors (1) demonstrate that the instability represents a combination of spontaneous mutation or deletion of the inserted gene and selection for non-expressing mutants and (2) describe novel methods for reducing instability.

Overview

Recombinant MVAs expressing env and gagpol from many different isolates were constructed. Each virus was subjected to repeated passages in chicken embryo fibroblast cells to mimic the large-scale amplification required for production of virus for clinical trials. Insert stability was monitored by env and gag immunostaining of individual plaques. For some recombinant viruses, any and/or gag expression was found to be rapidly lost in a significant fraction of the virus population. To identify the mechanism(s) of loss of expression, individual plaques were isolated and the nature of the mutations was characterized. In some cases, specific DNA sequences with propensity to mutate by addition or deletion of a single nucleotide were identified. Generation of such mutations could be avoided by altering codons without changing the predicted translation product. In other cases, loss of expression was caused by large deletions that frequently extended into flanking non-essential MVA genes. To prevent this from occurring, a new shuttle plasmid was constructed that was designed to direct insertion of foreign genes between two essential MVA genes. Recombination into this site reduced deletions of the foreign DNA. In one case, however, the toxicity associated with high-level HIV env expression was so severe that the selection of rare mutants still resulted in an unstable population. In this case, only truncation of the transmembrane domain of env allowed the construction of a stable recombinant MVA.

Generation of Recombinant MVAs and Analysis of Stability of Inserted Genes

Env and gagpol genes were cloned into MVA shuttle vectors. Expression and function were analyzed by transient expression assays. Gagpol was recombined into MVA 1974/NIH Clone 1. Recombinant MVA were plaque purified with 6-8 rounds followed by amplification of virus. Env was recombined into the MVA/gagpol isolate and double-recombinant MVA (FIG. 11A) were plaque purified with 6-8 rounds and were amplified. To assess the stability of inserts, virus was serially passaged in CEF cells using a multiplicity of infection (m.o.i.) of ~1 pfu/cell to mimic large-scale production. Stability was evaluated by determining the percentage of cells expressing env or gag, as determined by immunostaining with monoclonal antibodies (FIG. 11B).

Stability of Recombinant MVAs

Recombinant MVAs expressing genes from HIV-1 isolates from different geographical locations were constructed. The any and gagpol genes were inserted into deletions II and III of MVA, respectively; both under control of the modified H5 promoter. The stability of env and gagpol genes from seven recombinant MVAs is shown in Table 4. Varying degrees of instability were observed in the seven viruses. In MVA/65A/G, expression of env was rapidly lost with only 25% of virions expressing any by passage 6. In MVA/UGD4a, both env and gagpol expression were increasingly lost with successive virus passages. Since at least 6-7 passages are required for production of a lot of virus for a Phase I trial, these two viruses were deemed unsuitable.

Analysis of Expression of MVA/65A/G

Figure 12:
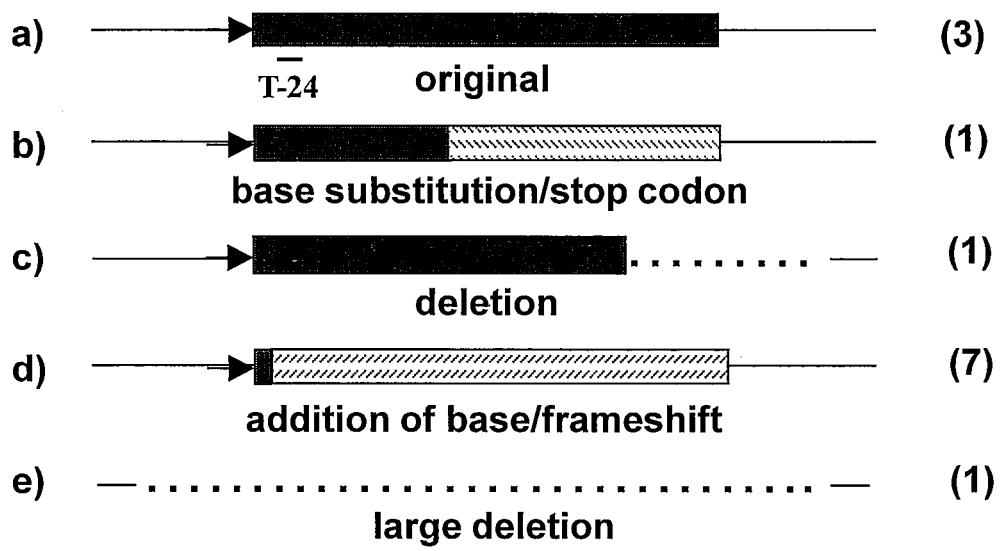
FIG. 12. Types and frequency of envy mutations in MVA/65A/G env.

Referring to FIG. 12, thirteen plaques were randomly picked from P3 and P5 of MVA/65A/G and analyzed by immunostaining with T-24 mAb (binding site shown on a), Western blotting, PCR, and sequencing. Five types of plaques were found and the number of these plaques obtained for each type are given at right of FIG. 12. Plaques a, b, and c stained, but b and c were truncated versions due to base substitution (causing stop codon) (b) and deletion of the end of the any gene and part of MVA flank (c). Non-staining plaques d and a resulted from addition of G to a 5G run causing a frameshift (d) and large deletion of entire env gene and parts of MVA flanks (e). Thus, base pair addition, substitution, and deletions all contributed to unstable expression of the env gene in MVA/65A/G. This A/G any, the most unstable example worked with, was picked to study modifications that might enhance stability.

Modifications to A/G Constructs to Increase Stability

1. Synthetic envelope was made by removing 4 and 5 G and C runs by silent mutations to prevent point mutations.

Figure 13:
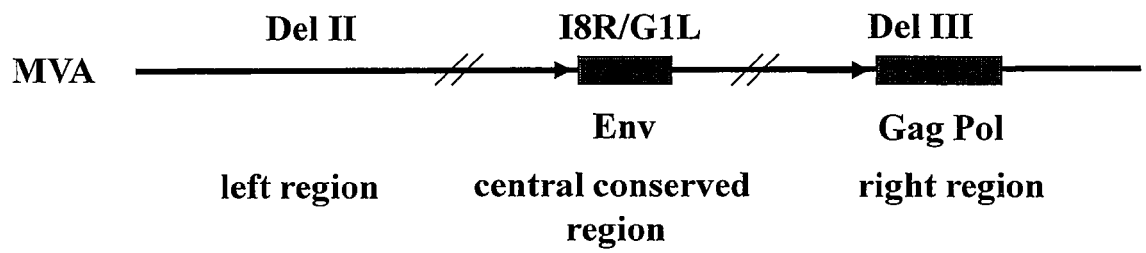
FIG. 13. Insertion of Env in I8R/G1L IGR and Gag Pol in Del III.

2. Vector I8/G1, i.e., pLW-73, was constructed with an insertion site between essential genes I8R and G1L to prevent deletions of genes and MVA flanks from being viable. The ends of the I8R (500 bp) and G1L (750 bp) genes of MVA were amplified by PCR and inserted into a vector containing vaccinia virus early/late mH5 promoter controlling foreign gene expression. This I8/G1 vector was used to insert foreign genes into MVA by homologous recombination (FIG. 13). Deletions of inserted genes and MVA flanking the inserted gene would not be viable because parts of essential genes would be deleted. Therefore, viruses with these mutations would not be able to overgrow the population with their normal growth advantage.

3. A/G gp140 envelope was mutated by deleting the transmembrane domain and the cytoplasmic tail of gp41, resulting in a secreted protein.

Testing Modifications to Increase Stability

Figure 14:
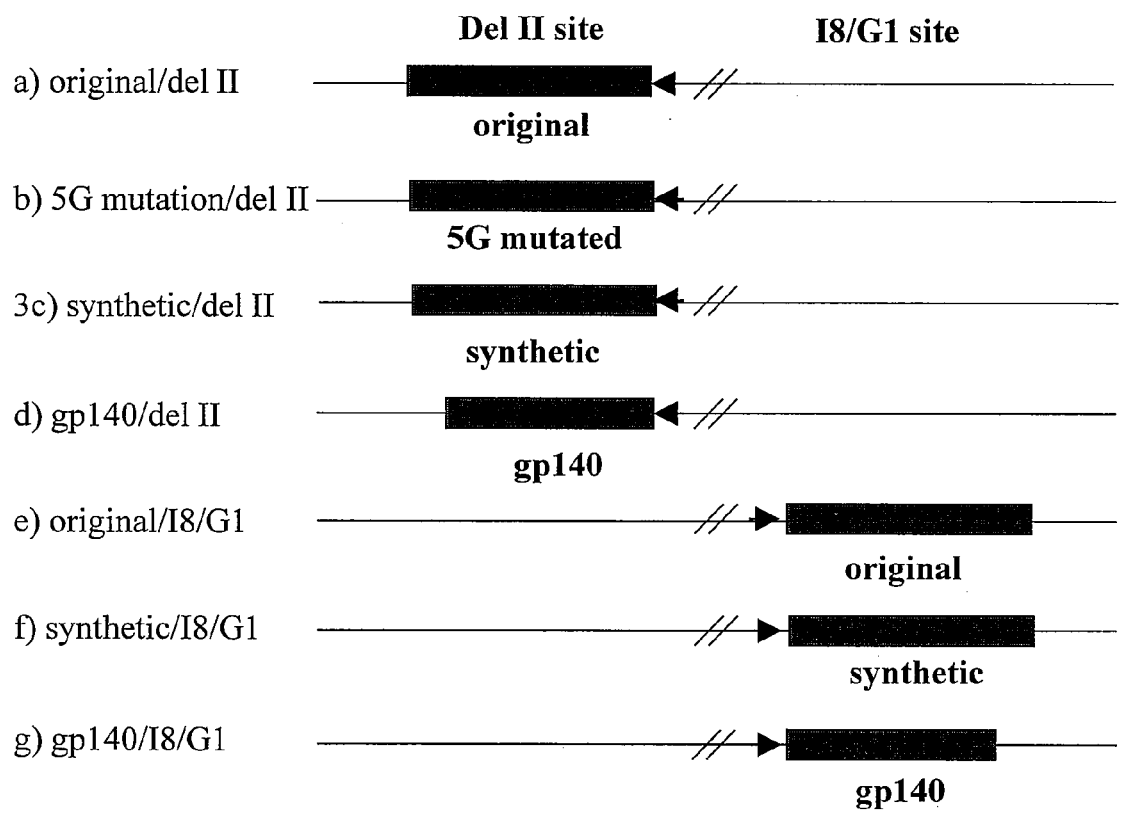
FIG. 14. Modifications to A/G constructs to increase stability.

Seven single recombinant viruses were made with env modifications and/or use of new vector as shown in FIG. 14. Five plaques of each virus were isolated and passaged independently in CEF to determine if modifications enhanced envelope stable expression. Passaged plaques were analyzed by immunostaining with mAb T-43 (binding site mapped to 101-125aa of env), Western blotting, PCR, and sequencing.

Env Expression after Plaque Passages

Figure 15:
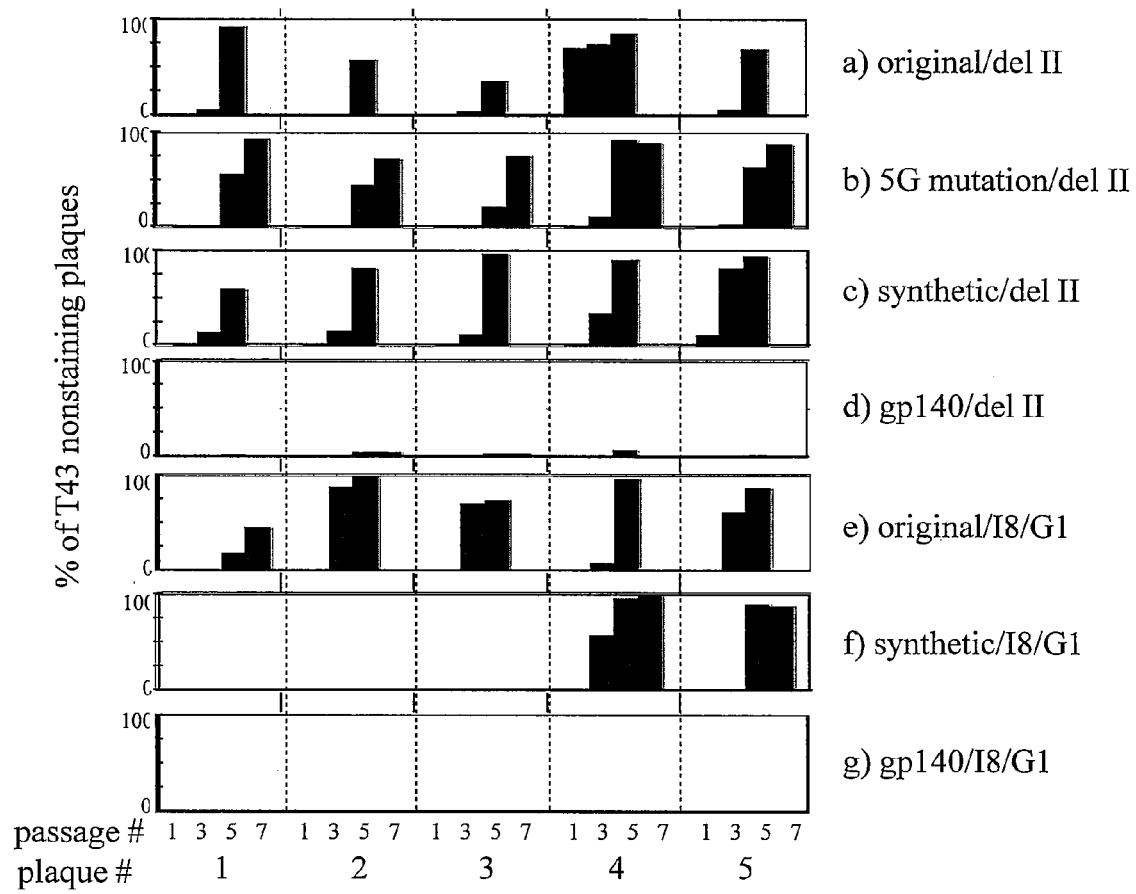
FIG. 15. Env expression after plaque passages.

Referring to FIG. 15, five independently passaged plaque isolates of each of the 7 recombinants listed above, were characterized at passages 1, 3, 5, and 7 by immunostaining with mAb T-43 (binds between 101-125a.a. in gp120). Four of 7 viruses (FIG. 15, a, b, c, e) had unstable protein expression in each of the 5 passaged plaques; two plaque passages of (FIG. 15f) also had unstable env expression. These included viruses with the synthetic env in both del II (FIG. 15c) and in the essential gene site (FIG. 15f) of MVA genome. Only recombinant viruses containing the envelope as truncated, secreted gp140 remained stably expressing envelope (FIGS. 15, d and g).

Western Blotting PCR and Sequence Analyses

Figure 16:
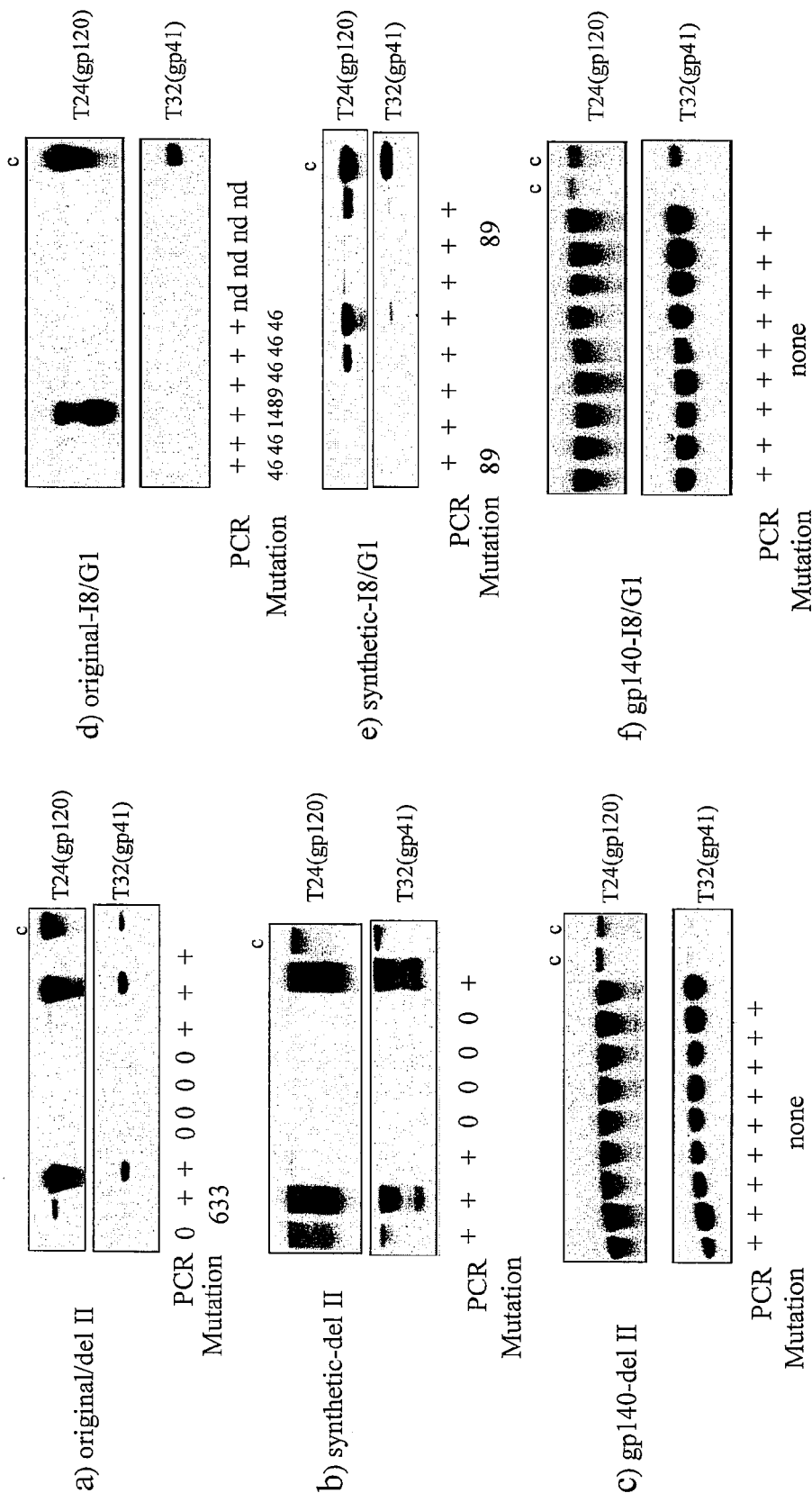
FIG. 16. PCR and Western blot analysis of individual clones.

From selected plaque passages, clones were picked to analyze protein expression by Western blotting, PCR, and sequence analysis (FIG. 16). For Western blot analysis, T-24 and T-32 binding at the beginning and end of the clade A envelope, respectively, were used in order to determine if only partial or full length envelope was being made. Control viruses, marked c, are at the right of each blot. For the three viruses made in deletion II of MVA (FIGS. 16a, b, and c), only in FIG. 16e (i.e., gp140 clones), were all the clones expressing detectable protein in Western. This protein (as measured by T-32) was not truncated. When envelope was inserted into the essential gene site by vector I8/G1 (FIGS. 16d, e and f), again, only the gp140 envelope was being expressed in all clones and was not truncated. Although use of I8/G1 vector did not prevent mutations to the env sequence, it did prevent deletions which had been seen in envelope inserted into del II. (Note positive PCR products from all clones tested from I8/G1 vector, but negative PCR products from clones tested using del II vector.)

Expression of Env in Clade A/G Double Recombinant

Figure 17:
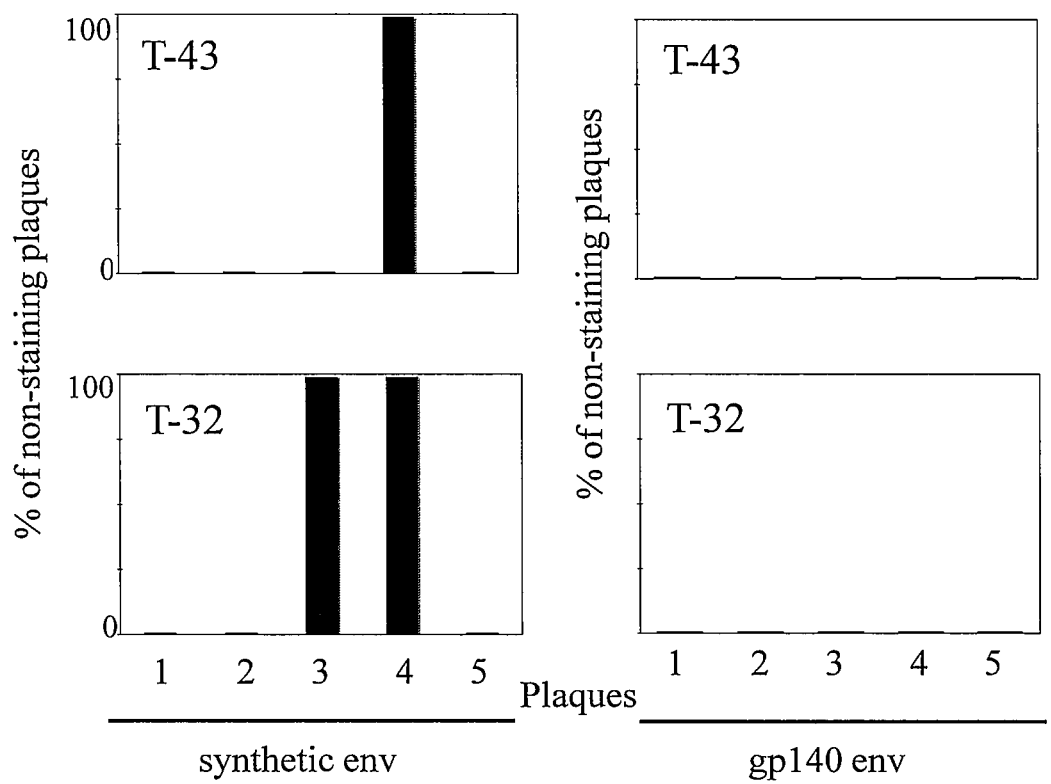
FIG. 17. Expression of A/G env by double recombinant MVA.

Based on previous results with single my analysis, double recombinants expressing gagpol with either gp140 or the synthetic gp160 gene were made and tested for stability of my expression (FIG. 17). Five plaques were isolated from each as previously described, and passaged 7 times to analyze stability of env expression. At passage 7, the passaged plaques were immunostained with both T-43 and T-32 mAbs (which bind to gp120 and gp41, respectively). With T-43 mAb, one of five clones of recombinant expressing synthetic envelope consisted of only non-staining plaques. Subsequent T-32 staining of these plaques showed another plaque had truncated envelope expression. All passaged plaques from double recombinant containing gp140 envelope appeared stable by both T-43 and T-32 immunostaining. Titers were also 2 logs higher than with the other double recombinant. Thus a clade A/G double recombinant stably expressing envelope could only be made with gp140 envelope.

Recombinant Viruses Expressing Env and Gagpol from Ugandan HIV-1 Isolates

Figure 18:
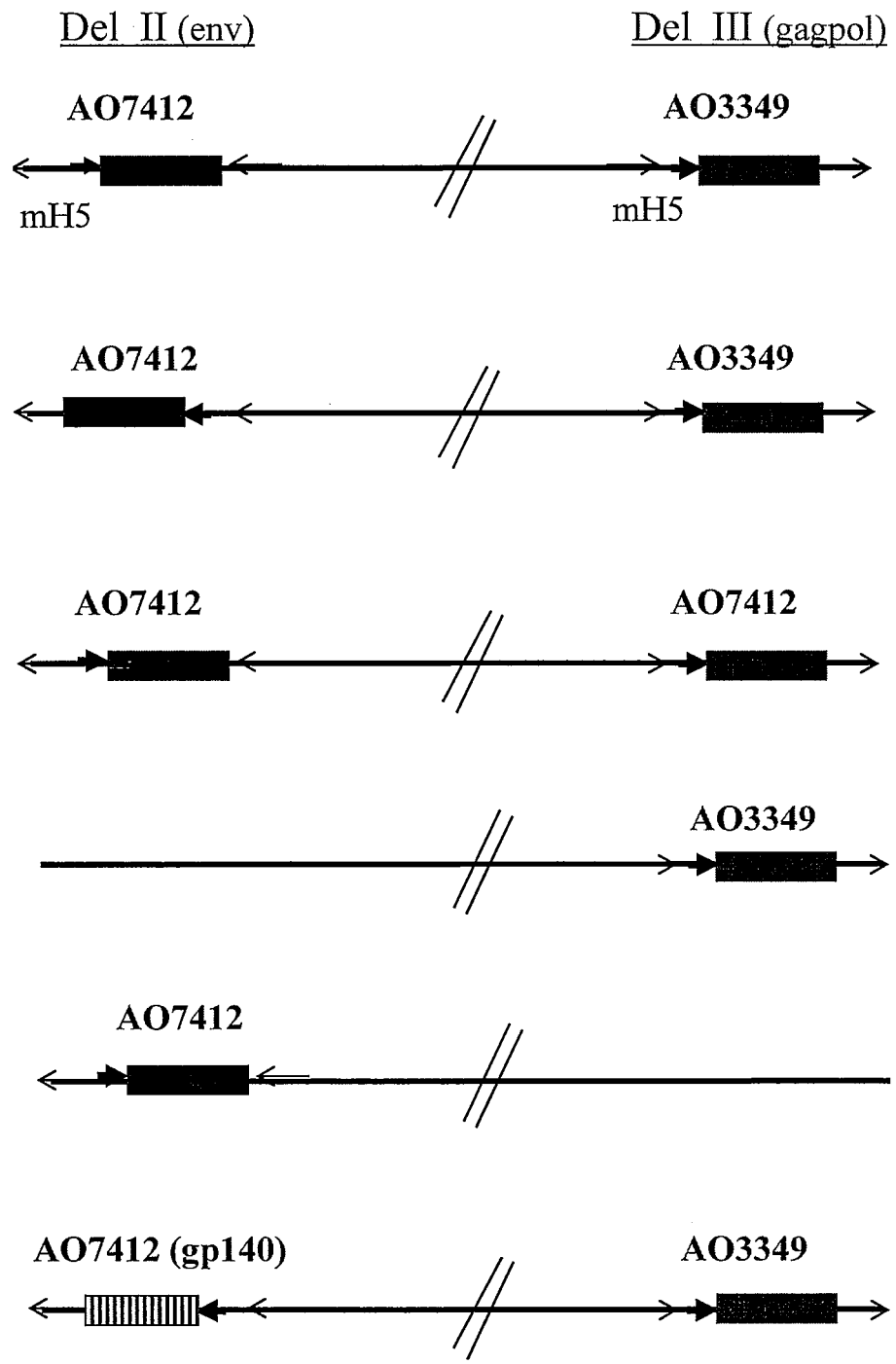
FIG. 18. Recombinant viruses expressing env and gagpol from Ugandan HIV-1 isolates.

Recombinant MVA viruses expressing HIV-1 env and gagpol genes from Ugandan isolates AO7412 and AO3349 were constructed as shown in FIG. 18. Four to six independent isolates of each were serially passaged and both genes were found to be unstable whether expressed alone or in combination (Table 5). In contrast, expression of gp140 instead of membrane bound gp160 resulted in stability of the env gene after serial passage (FIG. 18 and Table 5).

MVA/UGD4a—Analysis of Non-Staining Env Plaques

Figure 19:
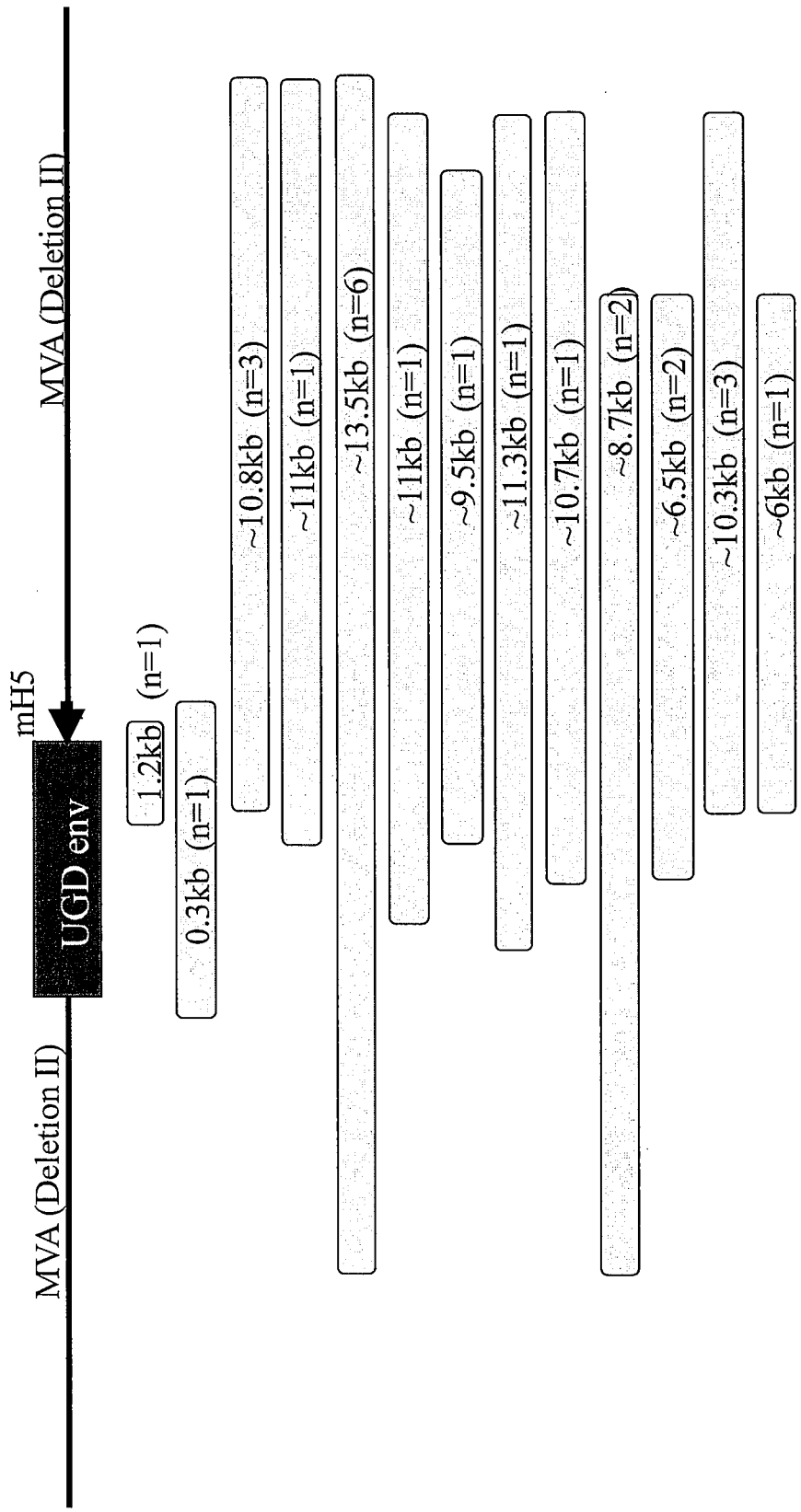
FIG. 19. MVA/UGD4a—analysis of non-staining env plaques.

To determine the mechanism of instability, 24 individual non-staining plaques (using Mab T-43) were isolated from passage 6 of MVA/UGD4a, amplified, and characterized. Two small deletions (1.2 and 0.3 kb) were identified by PCR amplification and DNA sequencing (FIG. 19). All other isolates contained very large deletions that extended into the flanking MVA. The approximate break-points for these deletions were identified using primer pairs from within the env ene or flanking MVA regions.

Modification of UGD Env Gene in Recombinant MVA

Figure 20:
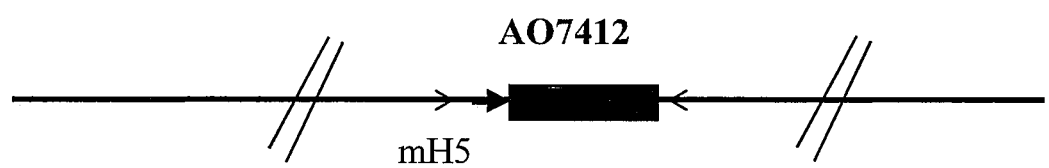
FIG. 20. Modification of UGD env gene in recombinant MVA.

To ameliorate the problem of instability of the UGD env gene, the AO7412 env gene was inserted into MVA using the new vector, I8/G1, which directs recombination of a foreign gone between 2 essential vaccinia virus genes, I8 and G1 and uses the modified H5 promoter (FIG. 20). Four independent plaques were serially passaged and analyzed for env expression by immunostaining with Mabs T-43 and T-32 at passage 5. In all isolates, the gene was stable (Table 6).

MVA/UGD4b—Analysis of Non-Staining Gag Plaques

Figure 21:
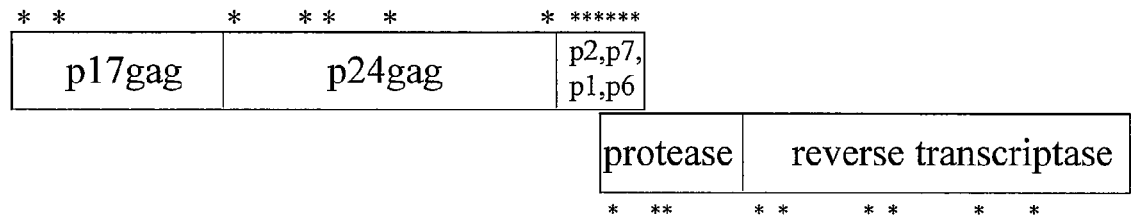
FIG. 21. MVA/UGD4b—analysis of non-staining gag plaques. *, location of runs of 4-6 G or C residues.

To determine the mechanism of instability of the gag gene, 8 individual non-staining plaques (using Mab 183-H12-5C-NIAID AIDS Repository) were picked from passage 6 of MVA/UGD4b, amplified, and the gagpol insert was sequenced (Table 7). In 7 isolates, an insertion or deletion of a single G residue at position 564-569 was found. In one isolate, a C residue was deleted from the sequence CCCC at position 530-534. Furthermore, non-staining plaques from high-passage stocks of MVA/KEA and MVA/TZC revealed a similar hot-spot for mutation, i.e., position 564-569. Examination of the full sequence of the UGD AO7412 gagpol gene demonstrated 22 runs of 4 or more G or C residues (FIG. 21).

Modification of UGD Gagpol Gene in Recombinant MVA

Figure 22:
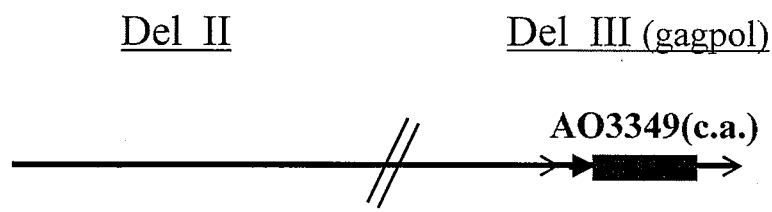
FIG. 22. Modification of UGD gagpol gene in recombinant MVA.

Since the mechanism of instability of the gagpol gene was primarily insertion or deletion of a single nucleotide within a run of 4-6 G or C residues, the strategy to improve the stability of this gene was to generate silent mutations at such sites. Thus, site-directed mutagenesis at 6 sites in p17 and p24 gag (Table 3) was employed. The resulting codon altered (c.a.) gene inserted into MVA at the same location, i.e., Deletion III, proved to be stable upon serial passage (FIG. 22 and Table 8).

Construction of Stable, Recombinant MVA Expressing UGD Env and Gagpol

Figure 23:
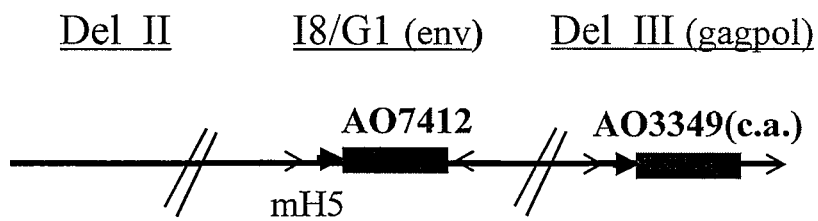
FIG. 23. Construction of stable recombinant MVA expressing UGD env and gagpol.
Figure 24:
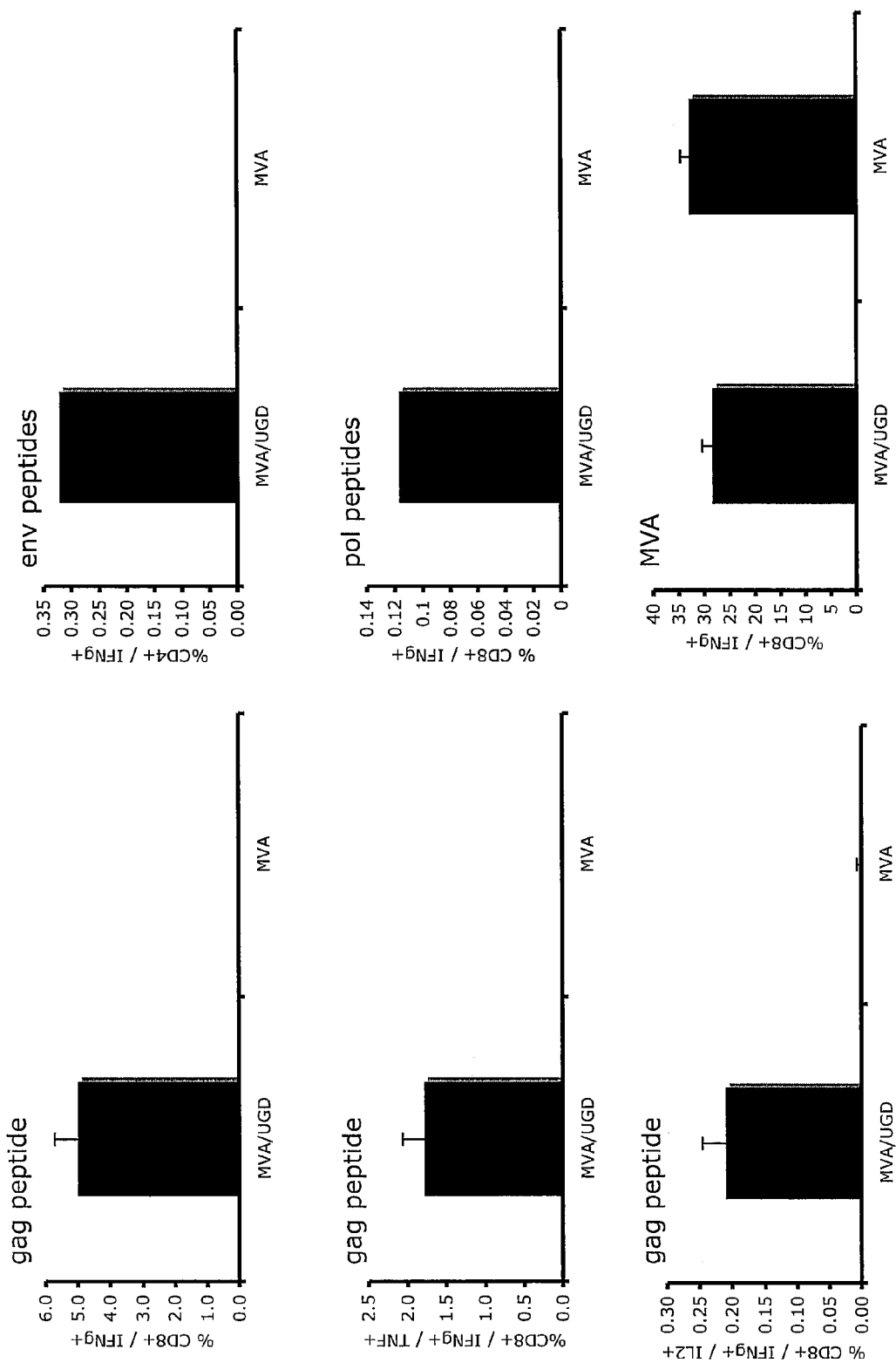
Figure 25:
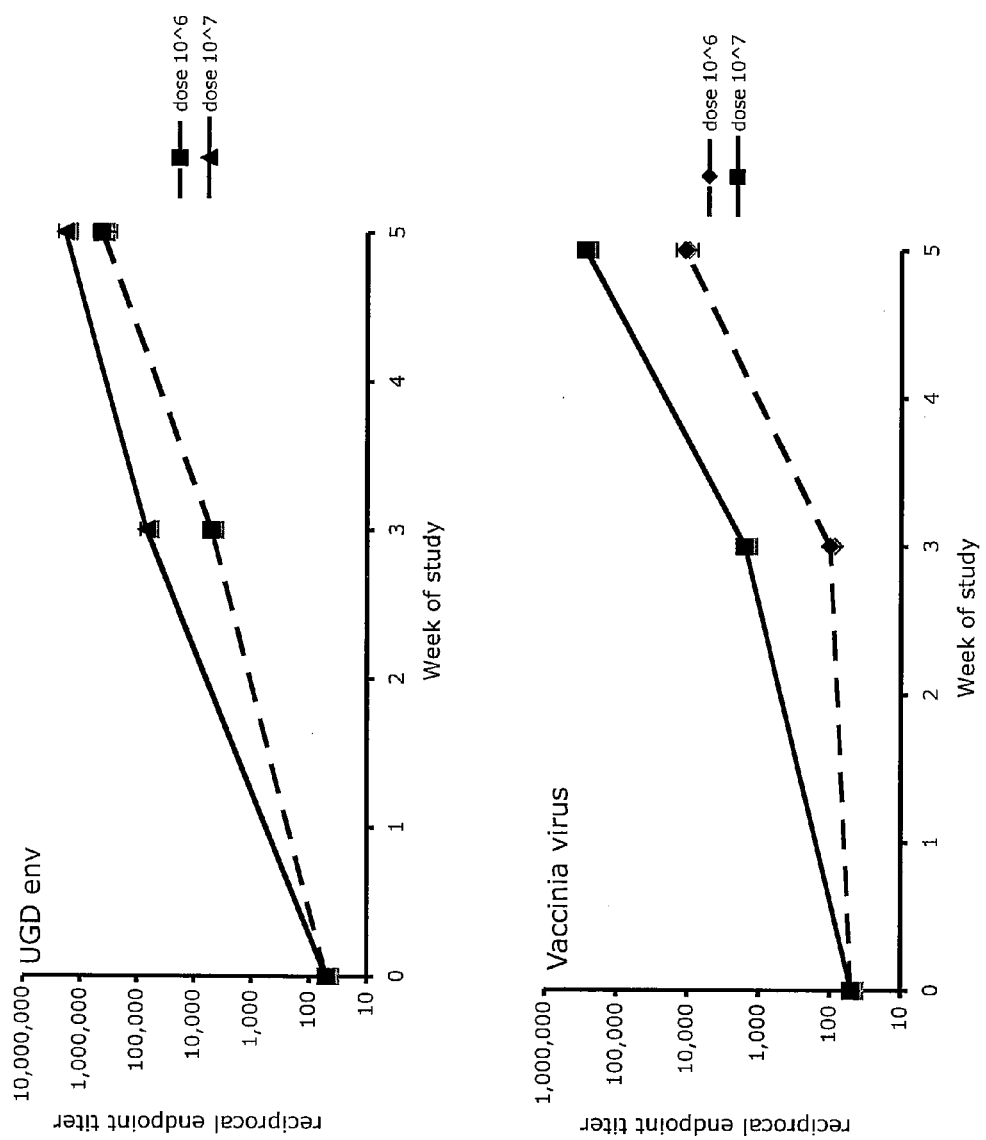

A recombinant virus expressing the UGD env gene in the I8/G1 locus and the codon altered gagpol gene in Deletion III of MVA was constructed (FIG. 23). Serial passage demonstrated no instability of either gene. Furthermore, the level of protein expression and DNA sequence were unaltered during passage (Table 9).

Conclusions

Instability of env and gagpol inserts is attributed to the generation of point mutations and deletions and the growth advantage of non-expressing MVA mutants. Instability can generally be reduced by codon alteration and/or insertion into an essential region of the MVA genome (MVA/UGD4d) but my had to be altered in one case (MVA/65A/G).

Example 3

Immunogenicity of MVA/UGD4d in BALB/c Mice

Groups of 10 mice each were immunized by the intraperitoneal route with either $10^6$ or $10^7$ infectious units of MVA/UGD4d. Groups of 5 mice each were similarly immunized with parental MVA-1974. Mice were immunized at weeks 0 and 3 and bled at weeks 0, 3, and 5. Spleens were harvested at week 5.

Cellular responses were measured in fresh splenocytes by intracellular cytokine staining. Splenocytes were separately stimulated with the following: 1) immunodominant gag peptide (AMQMLKETI (SEQ ID NO: 6)), 2) env peptides (DTEVHNVWATHACVP (SEQ ID NO: 7) and QQQSNLLRAIEAQQH (SEQ ID NO: 8)), 3) pol peptides (8 peptides with single amino acid variants of ELRQHLLRWGLTT (SEQ ID NO: 9) and HGVYYDPSKDLIAE (SEQ ID NO: 10)), and 4) MVA.

Cells were stained for surface expression of CD4 and CD8 and then for Intracellular expression of IFN-γ and either IL2 or TNF. As shown in FIG. 24, MVA/UGD4d elicited CD8/IFN-γ responses to the gag peptide, pol peptides, and MVA. The gag peptide responses were multifunctional, expressing both IFN-γ and either IL2 or TNF. Also, CD4/IFN-γ responses were elicited to the pool of env peptides.

Humoral responses were measured by ELISA (FIG. 25). Strong responses to UGD env were demonstrated at 3 weeks after one immunization and were boosted by the second immunization. In addition, strong vaccinia virus responses were elicited after one and two immunizations.

TABLE 3

MVA/UGD Nucleotide Changes Made to Eliminate Runs of G and C (HIV-1 isolate A03349)

| Nucleotide # starting with ATG | Original Sequence | Modified Sequence |
|---|---|---|
| 28-32 | GGGGG | GGAGG |
| 70-74 | GGGGG | GGAGG |
| 408-411 | GGGG | GGGA |
| 530-533 | CCCC | CACC |
| 564-569 | GGGGGG | AGGAGG |
| 686-689 | GGGG | GAGG |

TABLE 4

Stability of Recombinant MVAs

| | | | Percent non-staining plaques | | | | | | | | | | | |
|---|---|---|---|---|---|---|---|---|---|---|---|---|---|---|
| | | Geographic | LVD seed | | passage 3/4 | | passage 6/7 | | passage 9/9 | | passage 10-13 | | vaccine lot | |
| Virus | Clade | origin | env | gag | env | gag | env | gag | env | gag | env | gag | env | gag |
| KEA5b | A | Kenya | <1 | <1 | 0.13 | 0.33 | 0.34 | 0.36 | | | 0.54 | 2.4 | 0.64 | 0.77 |
| 65A/G | A/G | Ivory Coast | <2 | <1 | 28 | 1 | 75 | | | | | | | |
| 62B | B | US | <1 | <1 | <1 | <1 | | | 6 | <1 | 10 | 1 | | |
| TZCa | C | Tanzania | <1 | <1 | <1 | <1 | 1.7 | 2.8 | 3.6 | 3.7 | | | | |
| 71C | C | India | <1 | <1 | <1 | 1 | <1 | 2 | 12 | 14 | | | | |
| UGD4a | D | Uganda | <1 | <1 | 3 | 0.28 | 6.7 | 6 | 12.2 | 17.4 | | | | |
| CMDR | E/A | Thailand | <1 | <1 | <1 | <1 | <1 | <1 | | | | | <1 | <1 |

TABLE 5

Recombinant Viruses Expressing env and gagpol from Ugandan HIV-1 isolates

| | | % non-staining | |
|---|---|---|---|
| | passage | env | gag |
| UGD4a | 9 | 12.2 | 17.4 |
| | 5 | 5.8 | 2.6 |
| | 5 | 2.7 | 17.6 |
| | 5 | 8.4 | 7.2 |
| | 5 | 11.4 | 8.0 |
| UGD4b | 6 | 1.5 | 17.0 |
| | 5 | 3.3 | 9.3 |
| | 5 | 3.7 | 8.3 |
| | 5 | 7.9 | 4.4 |
| | 5 | 15.2 | 5.0 |
| UGD1a | 4 | nd | 18.8 |
| | 4 | nd | 46.7 |
| | 4 | nd | 64.9 |
| | 4 | nd | 38.1 |
| | 5 | 7.9 | 44.8 |
| UGD gag3349 | 8 | | 36.6 |
| | 8 | | 25.4 |
| | 6 | | 22.9 |
| | 6 | | 33.1 |
| UGD env | 8 | 9.0 | |
| | 8 | 2.9 | |
| | 8 | 13.3 | |
| | 8 | 12.5 | |
| | 8 | 14.3 | |
| UGDgag/gp140 | 5 | 1.2 | 18.9 |
| | 5 | 2.3 | 17.6 |

TABLE 6

Modification of UGD env Gene in Recombinant MVA

| | | % non-staining | |
|---|---|---|---|
| | passage | env | gag |
| UGD9 | 5 | 0.5 | |
| | 5 | 0.4 | |
| | 5 | 0.0 | |
| | 5 | 0.5 | |

TABLE 7

MVA/UGD4b-Analysis of Non-Staining gag Plaques

| | | | # individual plaques with mutation | | |
|---|---|---|---|---|---|
| gene | base | # sequence | MVA/UGD | MVA/KEA | MVA/TZC |
| p17 | 28 | GGGGG | | | |
| | 70 | GGGGG | | n = 1 | |
| p24 | 408 | GGGG | | | |
| | 530 | CCCC | n = 1 | | |
| | 564 | GGGGGG | n = 7 | n = 16 | n = 21 |
| | 686 | GGGG | | | |
| | 1050 | GGGGGG | | | |
| p7 | 1133 | GGGG | | | |
| p1 | 1320 | GGGG | | | |
| p6 | 1361 | CCCC | | | |
| | 1387 | GGGG | | | |
| | 1419 | GGGG | | | |
| | 1473 | CCCC | | | |

TABLE 7 -continued

MVA/UGD4b-Analysis of Non-Staining gag Plaques

| | | | # individual plaques with mutation | | |
|---|---|---|---|---|---|
| gene | base | # sequence | MVA/UGD | MVA/KEA | MVA/TZC |
| Protease | 1494 | GGGGG | | | |
| RT | 1590 | GGGGG | | | |
| | 1599 | GGGGG | | | |
| | 2362 | GGGG | | | |
| | 2380 | GGGG | | | |
| | 2528 | GGGGGG | | | |
| | 2596 | GGGG | | | |
| | 2893 | GGGG | | | |
| | 3001 | CCCC | | | |

TABLE 8

Modification of UGD gagpol Gene in Recombinant MVA

| | | % non-staining | |
|---|---|---|---|
| | Passage | env | gag |
| UGD gag (c.a.) | 6 | | 0.9 |
| | 6 | | 0.0 |
| | 6 | | 0.5 |

TABLE 9

Construction of Stable Recombinant MVA Expressing UGD env and gagpol

| | | % non-staining | |
|---|---|---|---|
| | Passage | env | gag |
| UGD4d | 11 | 0.0 | 0.7 |

Example 4

This Example demonstrates the use of additional insertion sites for generating stable, recombinant MVA viruses. The Del III region of the MVA virus genome contains several non-essential genes, and fragments of genes, and thus has historically been used to insert heterologous nucleic acid sequences. Thus, the flanking region around the del III insertion site of MVA was analyzed for the presence of fragmented or non-essential genes. Genes known to be important for VACV replication in some cells, i.e. A50R DNA ligase and B1R kinase were located about 1 kbp and 1.8 kbp, respectively, from the del III insertion site. We reasoned we could make this a more stable insertion site if we removed the non-essential genes flanking the Del III insertion site. To this end, a nucleic acid construct (e.g., shuttle vector) with flanking sequences comprising the 3' end part of A50R DNA ligase ORF (left), and the 5' end of the B1R ORF, and promoter (right), was constructed as follows. This would effectively remove the area of non-essential genes between these two important genes when homologous recombination occurred.

A. Preparation of the A50R/B1R Shuttle Vector

Analysis of the flanking regions around the del III insertion site in the MVA genome, (bp number 143552, Acambis 3000 Genbank AY603355) revealed that at least two genes known to be important for VACV replication in some cells.

Figure 26:
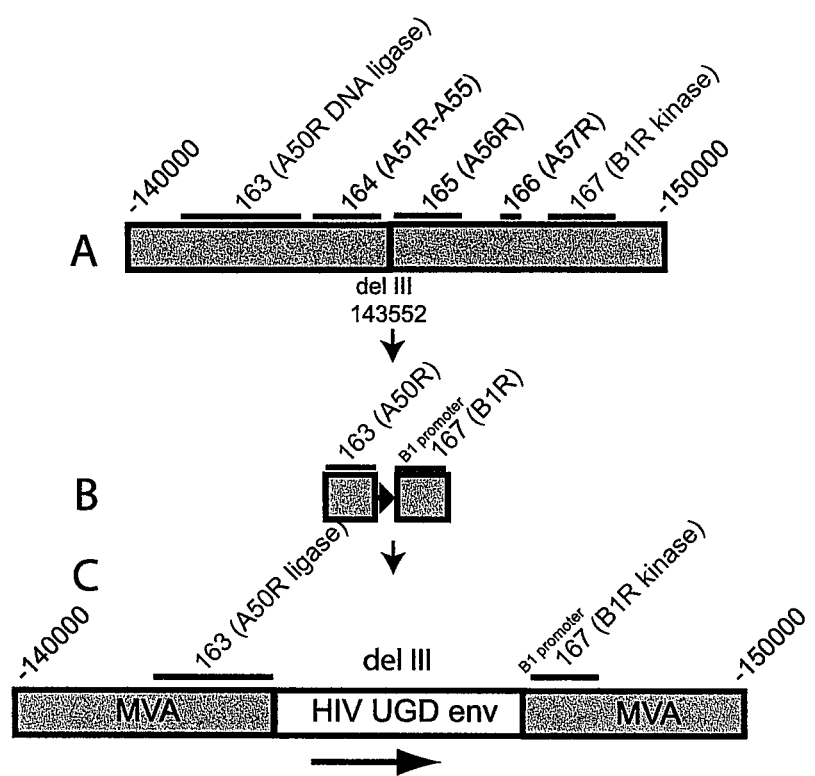
Figure 27:
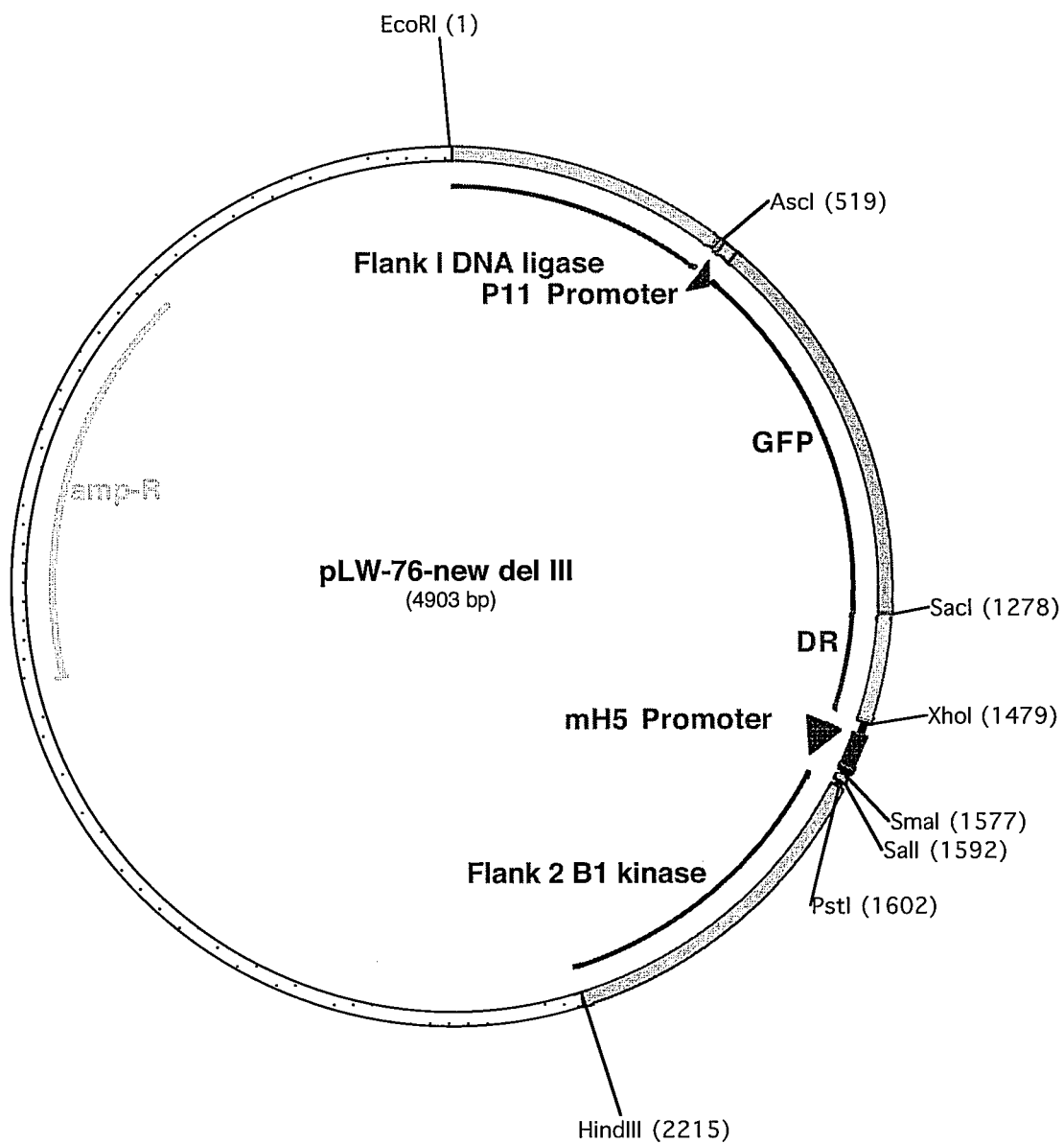
Figure 28:
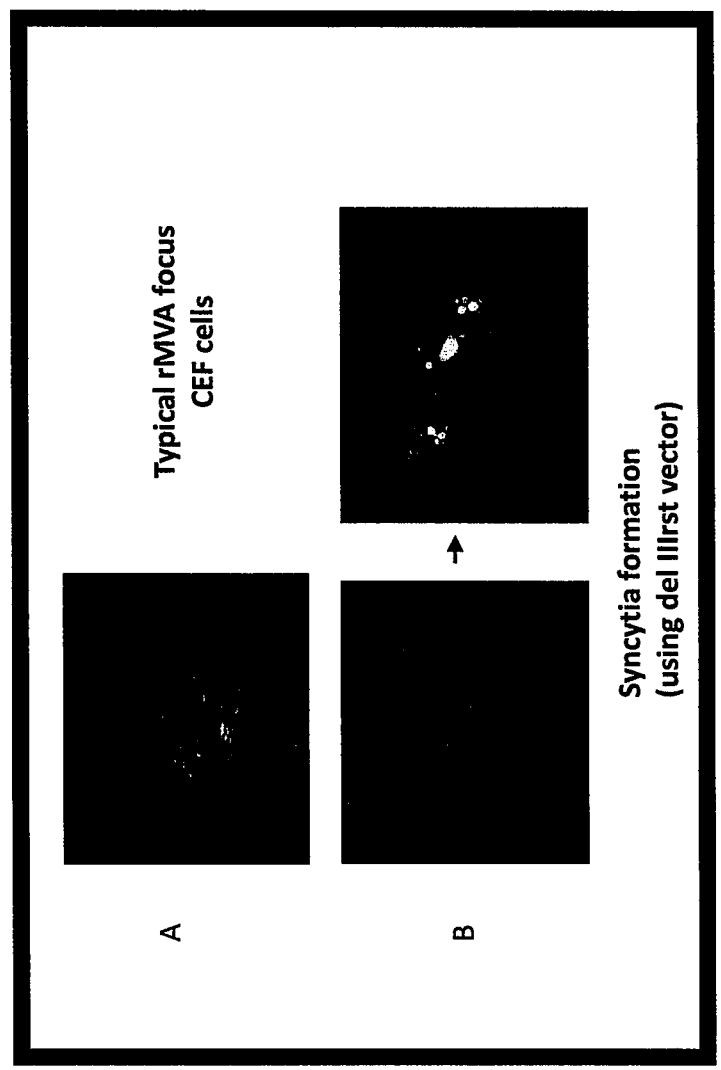
Figure 30:
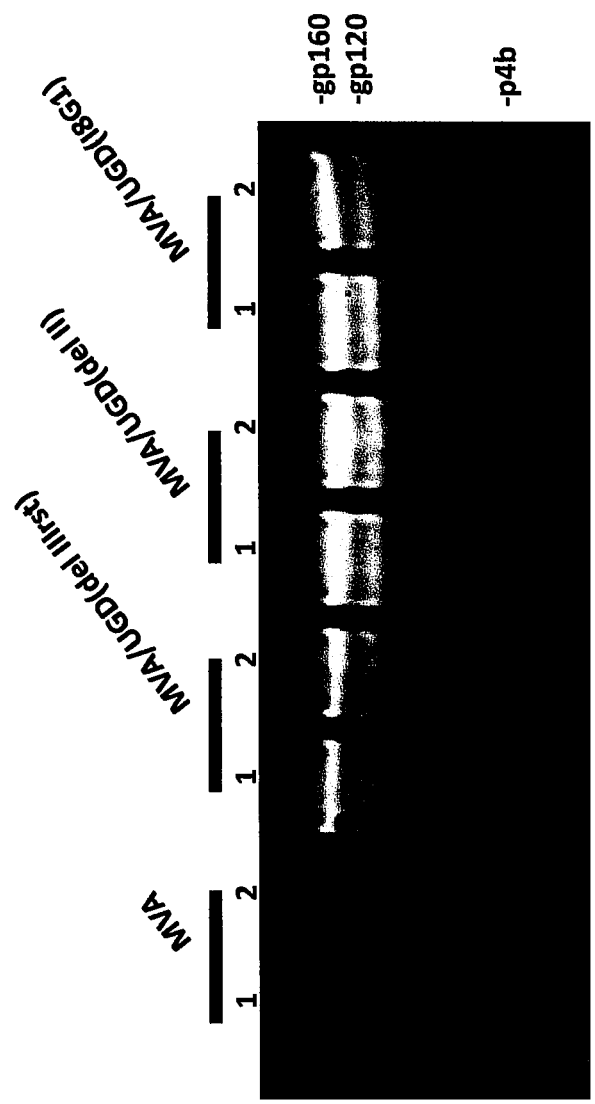

Specifically, A50R DNA ligase (ORF 163; ACAM3000_MVA_163; SEQ ID NO:11) and B1R kinase (ORF167; ACAM3000_MVA_167; SEQ ID NO:16) were located about 1 kbp and 1.8 kbp, respectively, from the del III insertion site. Thus, non-essential or fragmented genes located between ORF 163 and ORF 167 were targeted for removal. In particular, ORF 164, fragments of A51R-A55, ORF 165 (missing the part of the A56R promoter), ORF 166, and fragmented A57R were targeted for removal. In order to effect removal these non-essential and fragmented genes, a nucleic acid construct (i.e., a shuttle vector) was designed that would be capable of homologously recombining into the MVA genome between ORF 163 and ORF 167, thereby removing the intervening sequences. To achieve such recombination, the nucleic acid construct would comprise one nucleic acid sequence from ACAM3000_MVA_163 (the left flanking sequence), and one nucleic acid sequence from ACAM3000_MVA_167 (the right flanking sequence). These sequences would be adjacent in the nucleic acid construct, meaning that they would not be separated by any poxvirus ORF's. More specifically, the left flank would contain the C terminal end of the A50R ligase ORF and the right flank would contain the promoter region and the N terminal and of the B1R ORF. The design of the vector is shown in FIG. 26.

To construct the shuttle vector, each flank was created separately. The left flank of the restructured Del III vector was constructed first, as follows.

Plasmid LW-73 (FIG. 7) was digested with EcoRI and XhoI to excise the entire left flank (Flank 1 containing a portion of the I8R gene) along with the gene encoding green fluorescent protein (GFP) and direct repeat. The GFP containing fragment was then digested with restriction enzymes AcsI and SacI to liberate the GFP gene.

To create the left flank containing C-terminal portion of ORF 163, a DNA fragment was amplified from the MVA genome by the polymerase chain reaction (PCR) method using the primers LW470 (SEQ ID NO:23) and LW471 (SEQ ID NO:24). PCR amplification was performed using standard conditions. Next, the direct terminal repeat portion of ORF 163 was amplified from the MVA genome using the primers LW-472 (SEQ ID NO:25) and LW-473 (SEQ ID NO:26). Finally, the vector backbone, with EcoRI and XhoI sites, the GFP gene, with AcsI and SacI sites, the ORF 163 fragment (left flank) containing EcoRI and AscI sites, and the direct repeat from the ORF 163 C-terminus region, containing the SacI and XhoI sites, were ligated together to form the interim plasmid #2743.

To create the right flank containing the N-terminal portion of ORF 167, including its promoter region, interim plasmid #2743 was digested with the restriction enzymes Pst I and HindIII to release the right flank. Next, a DNA fragment was PCR amplified from the MVA genome using the primers LW-474 (SEQ ID NO:27) and LW-475 (SEQ ID NO 28). This fragment was digested with the restriction enzymes Pst I and Hind III, and the digested fragment ligated into similarly-digested, shuttle vector backbone to produce the LW-676 nucleic acid construct. (FIG. 27)

The salient features of pLW-76 are:

1) the vector is designed for insertion of foreign genes between the end of the A50R DNA ligase gene (ORF 163) and the promoter and N terminal portion of the B1R kinase gene (ORF 167) in MVA genome. The left flank consists of and of A50R ligase gene and right flank consists of promoter and beginning of the B1R kinase.

2) the GFP gene is included for easy initial selection of recombinant virus.

3) the GFP is flanked by direct repeat of the A50R ligase gene which allows for transient expression of GFP as the GFP will be lost upon repeated passage of the recombinant virus. Features 2 and 3 were also contained in earlier plasmids used for making MVA/HIV recombinants, pLAS-1 and pLAS-2.

The env gene from Ugandan clade D human immunodeficiency virus (HIV) (isolate AO7412) was then cloned into the new pLW-76 construct. The env containing nucleic acid construct was then transfected into cells, and the cells infected with MVA virus to produce a recombinant MVA virus expressing the HIV ENV protein rMVA/UGDenv (delIIIrst). This virus was then characterized.

When grown in chick embryo fibroblast (CEF) cells, it was observed that infection by rMVA/UGDenv(delIIIrst) resulted in syncytial-type, cytoplasmic effect (CPE). This was due to the deletion of the non-essential A56 hemagglutinin gene during recombination that occurred within the restructured del III site. Normal rMVA had a flay focus (FIG. 28A), whereas infection with rMVA/UGDenv (delIIrt) resulted in foci showing syncytial formation, progressing to condensed syncytial. (FIG. 28B).

rMVA/UGDenv (delIIIrst) was then characterized with regard to the stability of the inserted heterologous nucleic acid sequences. This was done by repeatedly passaging the virus in CEF cells, and testing each generation for the presence of expressed HIV ENV protein. Detection of ENV protein was done by screening viral plaques with monoclonal antibodies to the HIV envelope protein. The stability of rMVA/UGDenv (delIIIrst) was compared to a virus containing the env gene in the del II region, and a virus in which the env gene was inserted into the central conserved region. The results of this comparison are shown in FIG. 29. The level of ENV protein being expressed was also measured by Western blot, using monoclonal antibodies to the HIV ENV protein.

FIG. 29 shows that the MVA/UGDenv(del II) was clearly unstable, due to deletions that occurred within the any and extending into the flanking MVA. Viable deletions were prevented when the UGD env was placed between two VACV essential genes, as in MVA/UGDenv(I8/G1). Finally, integration of the HIV my gene int rMVA/UGDenv(del IIIrst), was observed to be stable at least through 11 passages.

FIG. 30 shows that 11 viral constructs expressed similar amounts of ENV protein.

Thus, the results of these studies suggest that the del III region of the MVA virus genome had been made more stable by restructuring the del III site by removing the non-essential genes.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated nucleic acid construct comprising:
   (a) a first nucleic acid sequence derived from, or homologous to, a first essential ORF from a poxvirus genome; and
   (b) a second nucleic acid sequence derived from, or homologous to, a second essential ORF from a poxvirus genome;
   wherein the first and second essential poxvirus ORFs are separated by at least one non-essential ORF in the parental poxvirus genome, and wherein the first and second nucleic acid sequences are adjacent to each other in the isolated nucleic acid construct.

2. The isolated nucleic acid sequence of claim 1, wherein the first nucleic acid sequence comprises at least 20 contiguous nucleotides from the first essential ORF, and wherein the second nucleic acid sequence comprises at least 20 contiguous nucleotides from the second essential ORF.

3. The isolated nucleic acid construct of claim 1, wherein the first nucleic acid sequence comprises an at least 100 contiguous polynucleotide region that is at least 75% identical to an at least 100 contiguous polynucleotide region in the first essential ORF, and wherein the second nucleic acid sequence comprises an at least 100 contiguous polynucleotide region that is at least 75% identical to an at least 100 contiguous polynucleotide region in the second essential ORF.

4. The isolated nucleic acid construct of claim 1, wherein the first essential ORF is selected from the group consisting of A11R, A12L, A50R, B1R, F10, F12, F13L, F15L, F17R, G1L, H2R, H3L, E1L, E4L, E6L, E8L, E10L, I1L, I3L, I5L, I8R, J1R, J3R, J4R, J5L, D7L, D9L, A24R, and A28R.

5. The isolated nucleic acid construct of claim 1, wherein the second essential ORF is selected from the group consisting of A11R, A12L, A50R, B1R, F10, F12, F13L, F15L, F17R, G1L, H2R, H3L, E1L, E4L, E6L, E8L, E10L, I1L, I3L, I5L, I8R, J1R, J3R, J4R, J5L, D7L, D9L, A24R, and A28R.

6. The isolated nucleic acid construct of claim 1, wherein the first essential ORF is A50R and the second essential ORF is B1R.

7. The isolated nucleic acid construct of claim 1, wherein adjacent ends of the first and second nucleic acid sequences are separated by a third nucleic acid sequence comprising at least one nucleotide sequence selected from the group consisting of (a) an intergenic region, and (b) a restriction enzyme recognition site.

8. The isolated nucleic acid construct of claim 1, wherein adjacent ends of the first and second nucleic acid sequences are separated by a heterologous nucleic acid sequence.

9. The isolated nucleic acid construct of claim 8, wherein the heterologous nucleic sequence comprises at least one coding sequence under the transcriptional control of a transcriptional control element.

10. The isolated nucleic acid construct of claim 1, wherein the poxvirus genome is from a poxvirus in the subfamily Chordopoxvirinae.

11. The isolated nucleic acid construct of claim 1, wherein the poxvirus genome is from a poxvirus in the genus *Orthopoxvirus*.

12. A method for producing a stable, recombinant poxvirus, the method comprising:
   (a) transfecting a cell with a nucleic acid construct comprising:
      i. a first nucleic acid sequence derived from, or homologous to, a first essential ORF from a poxvirus genome; and,
      ii. a second nucleic acid sequence derived from, or homologous to, a second essential ORF from a poxvirus genome;
   wherein the first and second essential poxvirus ORFs are separated by at least one non-essential ORF in the parental poxvirus genome, and wherein the first and second nucleic acid sequences are adjacent to each other in the isolated nucleic acid construct;

(b) infecting the transfected cell with a poxvirus;
(c) culturing the infected cell under conditions suitable to allow homologous recombination between the nucleic acid construct and the poxvirus genome.

13. The method of claim 12, wherein the first nucleic acid sequence comprises at least 20 contiguous nucleotides from the first essential ORF, and wherein the second nucleic acid sequence comprises at least 20 contiguous nucleotides from the second essential ORF.

14. The method of claim 12, wherein the first nucleic acid sequence comprises an at least 100 contiguous polynucleotide region that is at least 75% identical to an at least 100 contiguous polynucleotide region in the first essential ORF, and wherein the second nucleic acid sequence comprises an at least 100 contiguous polynucleotide region that is at least 75% identical to an at least 100 contiguous polynucleotide region in the second essential ORF.

15. The method of claim 12, wherein the first essential ORF is selected from the group consisting of A11R, A12L, A50R, B1R, F10, F12, F13L, F15L, F17R, G1L, H2R, H3L, E1L, E4L, E6L, E8L, E10L, I1L, I3L, I5L, I8R, J1R, J3R, J4R, J5L, D7L, D9L, A24R, and A28R.

16. The method of claim 12, wherein the second essential ORF is selected from the group consisting of A11R, A12L, A50R, B1R, F10, F12, F13L, F15L, F17R, G1L, H2R, H3L, E1L, E4L, E6L, E8L, E10L, I1L, I3L, I5L, I8R, J1R, J3R, J4R, J5L, D7L, D9L, A24R, and A28R.

17. The method of claim 12, wherein the first essential ORF is A50R and the second essential ORF is B1R.

18. The method of claim 12, wherein adjacent ends of the first and second nucleic acid sequences are separated by a third nucleic acid sequence comprising at least one nucleotide sequence selected from the group consisting of (a) an intergenic region, and (b) a restriction enzyme recognition site.

19. The method of claim 12, wherein adjacent ends of the first and second nucleic acid sequences are separated by a heterologous nucleic acid sequence.

20. The method of claim 19, wherein the heterologous nucleic sequence comprises at least one coding sequence under the transcriptional control of a transcriptional control element.

* * * * *

SEQUENCE LISTING

<160> NUMBER OF SEQ ID NOS: 48

<210> SEQ ID NO 1
<211> LENGTH: 4
<212> TYPE: PRT
<213> ORGANISM: Human immunodeficiency virus type 1
<220> FEATURE:
<221> NAME/KEY: MISC_FEATURE
<222> LOCATION: (2)..(3)
<223> OTHER INFORMATION: Xaa = unknown

<400> SEQUENCE: 1

Tyr Xaa Xaa Leu
1

<210> SEQ ID NO 2
<211> LENGTH: 5044
<212> TYPE: DNA
<213> ORGANISM: Artificial Sequence
<220> FEATURE:
<223> OTHER INFORMATION: Synthetic Construct

<400> SEQUENCE: 2

```
gaattccctg ggacatacgt atatttctat gatctgtctt atatgaagtc tatacagcga      60
atagattcag aatttctaca taattatata ttgtacgcta ataagtttaa tctaacactc     120
cccgaagatt tgtttataat ccctacaaat ttggatattc tatggcgtac aaaggaatat     180
atagactcgt tcgatattag tacagaaaca tggaataaat tattatccaa ttattatatg     240
aagatgatag agtatgctaa actttatgta ctaagtccta ttctcgctga ggagttggat     300
aattttgaga ggacgggaga attaactagt attgtacaag aagccatttt atctctaaat     360
ttacgaatta agattttaaa ttttaaacat aaagatgatg atacgtatat acacttttgt     420
aaaatattat tcggtgtcta aacggaaca aacgctacta tatattatca tagacctcta     480
acgggatata tgaatatgat ttcagatact atatttgttc ctgtagataa taactaaggc     540
gcgcctttca ttttgttttt ttctatgcta taaatggtga gcaagggcga ggagctgttc     600 accgggtgg tgcccatcct ggtcgagctg gacggcgacg taaacggcca aagttcagc     660 gtgtccggcg agggcgaggg cgatgccacc tacggcaagc tgaccctgaa gttcatctgc     720
accaccggca agctgcccgt gccctggccc accctcgtga ccaccctgac ctacggcgtg     780
cagtgcttca gccgctaccc cgaccacatg aagcagcacg acttcttcaa gtccgccatg     840
cccgaaggct acgtccagga gcgcaccatc ttcttcaagg acgacggcaa ctacaagacc     900
cgcgccgagg tgaagttcga gggcgacacc ctggtgaacc gcatcgagct gaagggcatc     960
gacttcaagg aggacggcaa catcctgggg cacaagctgg agtacaacta caacagccac    1020
aacgtctata tcatggccga caagcagaag aacggcatca aggtgaactt caagatccgc    1080
cacaacatcg aggacggcag cgtgcagctc gccgaccact accagcagaa cacccccatc    1140
ggcgacggcc ccgtgctgct gcccgacaac cactacctga gcacccagtc cgccctgagc    1200
aaagacccca acgagaagcg cgatcacatg gtcctgctgg agttcgtgac cgccgccggg    1260
atcactctcg gcatgcacga gctgtacaag taagagctcg aggacgggag aattaactag    1320
tattgtacaa gaagccattt tatctctaaa tttacgaatt aagattttaa attttaaaca    1380
taaagatgat gatacgtata tacacttttg taaaatatta ttcggtgtct ataacggaac    1440
aaacgctact atatattatc atagacctct aacgggatat atgaatatga tttcagatac    1500
tatatttgtt cctgtagata taactaact cgaggccgct ggtacccaac ctaaaaattg    1560
```

```
aaaataaata caaaggttct tgagggttgt gttaaattga aagcgagaaa taatcataaa      1620
taagcccggg gatcctctag agtcgacctg cagtcaaact ctaatgacca catcttttt       1680 tagagatgaa aaattttcca catctccttt tgtagacacg actaaacatt ttgcagaaaa      1740
aagtttatta gtgtttagat aatcgtatac ttcatcagtg tagatagtaa atgtgaacag      1800
ataaaaggta ttcttgctca atagattggt aaattccata gaatatatta atcctttctt     1860
cttgagatcc cacatcattt caaccagaga cgttttatcc aatgatttac ctcgtactat     1920
accacataca aaactagatt ttgcagtgac gtcgtatctg gtattcctac caaacaaaat     1980 tttacttta gttcttttag aaaattctaa ggtagaatct ctatttgcca atatgtcatc      2040
tatggaatta ccactagcaa aaaatgatag aaatatatat tgatacatcg cagctggttt     2100
tgatctacta tactttaaaa acgaatcaga ttccataatt gcctgtatat catcagctga     2160
aaaactatgt tttacacgta ttccttcggc atttcttttt aatgatatat cttgtttaga     2220
caatgataaa gttatcatgt ccatgagaga cgcgtctccg tatcgtataa atatttcatt    2280
agatgttaga cgcttcatta ggggtatact tctataaggt ttcttaatca gtccatcatt    2340
ggttgcgtca agaacaagct tgtctcccta tagtgagtcg tattagagct tggcgtaatc    2400
atggtcatag ctgtttcctg tgtgaaattg ttatccgctc acaattccac acaacatacg    2460
agccggaagc ataaagtgta aagcctgggg tgcctaatga gtgagctaac tcacattaat    2520
tgcgttgcgc tcactgcccg ctttcgagtc gggaaacctg tcgtgccagc tgcattaatg    2580
aatcggccaa cgcgcgggga gaggcggttt gcgtattggg cgctcttccg cttcctcgct    2640
cactgactcg ctgcgctcgg tcgttcggct gcggcgagcg gtatcagctc actcaaaggc    2700
ggtaatacgg ttatccacag aatcagggga taacgcagga agaacatgt gagcaaaagg     2760 ccagcaaaag gccaggaacc gtaaaaaggc cgcgttgctg gcgtttttcg ataggctccg    2820 ccccctgac gagcatcaca aaaatcgacg ctcaagtcag aggtggcgaa acccgacagg     2880
actataaaga taccaggcgt ttccccctgg aagctccctc gtgcgctctc ctgttccgac    2940
cctgccgctt accggatacc tgtccgcctt tctcccttcg ggaagcgtgg cgctttctca    3000
tagctcacgc tgtaggtatc tcagttcggt gtaggtcgtt cgctccaagc tgggctgtgt    3060
gcacgaaccc cccgttcagc ccgaccgctg cgccttatcc ggtaactatc gtcttgagtc    3120
caacccggta agacacgact tatcgccact ggcagcagcc actggtaaca ggattagcag    3180
agcgaggtat gtaggcggtg ctacagagtt cttgaagtgg tggcctaact acggctacac    3240
tagaaggaca gtatttggta tctgcgctct gctgaagcca gttaccttcg gaaaaagagt    3300
tggtagctct tgatccggca aacaaaccac cgctggtagc ggtggttttt ttgtttgcaa    3360
gcagcagatt acgcgcagaa aaaaaggatc tcaagaagat cctttgatct ttctctacggg   3420 gtctgacgct cagtggaacg aaaactcacg ttaagggatt ttggtcatga gattatcaaa    3480
aaggatcttc acctagatcc ttttaaatta aaaatgaagt tttaaatcaa tctaaagtat    3540
atatgagtaa acttggtctg acagttacca atgcttaatc agtgaggcac ctatctcagc    3600
gatctgtcta tttcgttcat ccatagttgc ctgactcccc gtcgtgtaga taactacgat    3660 acggagggc ttaccatctg gccccagtgc tgcaatgata ccgcgagacc cacgctcacc     3720
ggctccagat ttatcagcaa taaaccagcc agccggaagg gccgagcgca gaagtggtcc    3780
tgcaacttta tccgcctcca tccagtctat taattgttgc cgggaagcta gagtaagtag    3840
ttcgccagtt aatagtttgc gcaacgttgt tggcattgct acaggcatcg tggtgtcacg    3900
ctcgtcgttt ggtatggctt cattcagctc cggttcccaa cgatcaaggc gagttacatg    3960
``` atccccatg ttgtgcaaaa aagcggttag ctccttcggt cctccgatcg ttgtcagaag    4020
taagttggcc gcagtgttat cactcatggt tatggcagca ctgcataatt ctcttactgt    4080
catgccatcc gtaagatgct tttctgtgac tggtgagtac tcaaccaagt cattctgaga    4140
atagtgtatg cggcgaccga gttgctcttg cccggcgtca atacgggata ataccgcgcc    4200
acatagcaga actttaaaag tgctcatcat tggaaaacgt tcttcggggc gaaaactctc    4260
aaggatctta ccgctgttga gatccagttc gatgtaaccc actcgtgcac ccaactgatc    4320
ttcagcatct tttactttca ccagcgtttc tgggtgagca aaaacaggaa ggcaaaatgc    4380
cgcaaaaaag gaataagggc gacacggaaa tgttgaata ctcatactct tcctttttca    4440
atattattga agcatttatc agggttattg tctcatgagc ggatacatat ttgaatgtat    4500
ttagaaaaat aaacaaatag gggttccgcg cacatttccc cgaaaagtgc cacctgacgt    4560
ctaagaaacc attattatca tgacattaac ctataaaaat aggcgtatca cgaggccctt    4620
tcgtctcgcg cgtttcggtg atgacggtga aaacctctga cacatgcagc tcccggagac    4680
ggtcacagct tgtctgtaag cggatgccgg gagcagacaa gcccgtcagg gcgcgtcagc    4740
gggtgttggc gggtgtcggg gctggcttaa ctatgcggca tcagagcaga ttgtactgag    4800
agtgcaccat atgcggtgtg aaataccgca cagatgcgta aggagaaaat accgcatcag    4860
gcgccattcg ccattcaggc tgcgcaactg ttgggaaggg cgatcggtgc gggcctcttc    4920
gctattacgc cagctggcga aggggggatg tgctgcaagg cgattaagtt gggtaacgcc    4980
agggttttcc cagtcacgac gttgtaaaac gacggccagt gaattggatt taggtgacac    5040
tata    5044

<210> SEQ ID NO 3
<211> LENGTH: 5044
<212> TYPE: DNA
<213> ORGANISM: Artificial Sequence
<220> FEATURE:
<223> OTHER INFORMATION: Synthetic Construct

<400> SEQUENCE: 3
tatagtgtca cctaaatcca attcactggc cgtcgtttta caacgtcgtg actgggaaaa      60
ccctggcgtt acccaactta atcgccttgc agcacatccc cctttcgcca gctggcgtaa     120
tagcgaagag gcccgcaccg atcgcccttc ccaacagttg cgcagcctga atggcgaatg     180
gcgcctgatg cggtattttc tccttacgca tctgtgcggt atttcacacc gcatatggtg     240
cactctcagt acaatctgct ctgatgccgc atagttaagc cagccccgac acccgccaac     300
acccgctgac gcgccctgac gggcttgtct gctcccggca tccgcttaca gacaagctgt     360
gaccgtctcc gggagctgca tgtgtcagag gttttcaccg tcatcaccga aacgcgcgag     420
acgaaagggc ctcgtgatac gcctattttt ataggttaat gtcatgataa taatggtttc     480
ttagacgtca ggtggcactt ttcggggaaa tgtgcgcgga acccctattt gtttattttt     540
ctaaatacat tcaaatatgt atccgctcat gagacaataa ccctgataaa tgcttcaata     600
atattgaaaa aggaagagta tgagtattca acatttccgt gtcgccctta ttccctttttt     660 tgcggcattt tgccttcctg ttttgctcac ccagaaacg ctggtgaaag taaaagatgc     720
tgaagatcag ttgggtgcac gagtgggtta catcgaactg gatctcaaca gcggtaagat     780
ccttgagagt tttcgccccg aagaacgttt tccaatgatg agcactttta aagttctgct     840
atgtggcgcg gtattatccc gtattgacgc cgggcaagag caactcggtc gccgcataca     900

```
ctattctcag aatgacttgg ttgagtactc accagtcaca gaaaagcatc ttacggatgg    960
catgacagta agagaattat gcagtgctgc cataaccatg agtgataaca ctgcggccaa   1020
cttacttctg acaacgatcg gaggaccgaa ggagctaacc gcttttttgc acaacatggg   1080
ggatcatgta actcgccttg atcgttggga accggagctg aatgaagcca taccaaacga   1140
cgagcgtgac accacgatgc ctgtagcaat gccaacaacg ttgcgcaaac tattaactgg   1200
cgaactactt actctagctt cccggcaaca attaatagac tggatggagg cggataaagt   1260
tgcaggacca cttctgcgct cggcccttcc ggctggctgg tttattgctg ataaatctgg   1320
agccggtgag cgtgggtctc gcggtatcat tgcagcactg gggccagatg gtaagccctc   1380
ccgtatcgta gttatctaca cgacggggag tcaggcaact atggatgaac gaaatagaca   1440
gatcgctgag ataggtgcct cactgattaa gcattggtaa ctgtcagacc aagtttactc   1500
atatatactt tagattgatt taaaacttca ttttttaattt aaaaggatct aggtgaagat   1560
cctttttgat aatctcatga ccaaaatccc ttaacgtgag ttttcgttcc actgagcgtc   1620
agacccgta gaaaagatca aggatcttc ttgagatcct ttttttctgc gcgtaatctg   1680
ctgcttgcaa acaaaaaaac caccgctacc agcggtggtt tgtttgccgg atcaagagct   1740
accaactctt tttccgaagg taactggctt cagcagagcg cagataccaa atactgtcct   1800
tctagtgtag ccgtagttag gccaccactt caagaactct gtagcaccgc ctacatacct   1860
cgctctgcta atcctgttac cagtggctgc tgccagtggc gataagtcgt gtcttaccgg   1920
gttggactca agacgatagt taccggataa ggcgcagcgg tcgggctgaa cggggggttc   1980
gtgcacacag cccagcttgg agcgaacgac ctacaccgaa ctgagatacc tacagcgtga   2040
gctatgagaa agcgccacgc ttcccgaagg gagaaaggcg gacaggtatc cggtaagcgg   2100
cagggtcgga acaggagagc gcacgaggga gcttccaggg ggaaacgcct ggtatcttta   2160
tagtcctgtc gggtttcgcc acctctgact tgagcgtcga ttttttgtgat gctcgtcagg   2220
ggggcggagc ctatcgaaaa acgccagcaa cgcggccttt ttacggttcc tggccttttg   2280
ctggcctttt gctcacatgt tctttcctgc gttatcccct gattctgtgg ataaccgtat   2340
taccgccttt gagtgagctg ataccgctcg ccgcagccga acgaccgagc gcagcgagtc   2400
agtgagcgag gaagcggaag agcgcccaat acgcaaaccg cctctccccg cgcgttggcc   2460
gattcattaa tgcagctggc acgacaggtt tcccgactcg aaagcgggca gtgagcgcaa   2520
cgcaattaat gtgagttagc tcactcatta ggcaccccag gctttacact ttatgcttcc   2580
ggctcgtatg ttgtgtggaa ttgtgagcgg ataacaattt cacacaggaa acagctatga   2640
ccatgattac gccaagctct aatacgactc actataggga gacaagcttg ttcttgacgc   2700
aaccaatgat ggactgatta agaaacctta tagaagtata cccctaatga agcgtctaac   2760
atctaatgaa atatttatac gatacggaga cgcgtctctc atggacatga taactttatc   2820
attgtctaaa caagatatat cattaaaaag aaatgccgaa ggaatacgtg taaaacatag   2880
ttttcagct gatgatatac aggcaattat ggaatctgat tcgtttttaa agtatagtag   2940
atcaaaacca gctgcgatgt atcaatatat atttctatca ttttttgcta gtggtaattc   3000
catagatgac atattggcaa atagagattc taccttagaa ttttctaaaa gaactaaaag   3060
taaaattttg tttggtagga ataccagata cgacgtcact gcaaaatcta gttttgtatg   3120
tggtatagta cgaggtaaat cattggataa aacgtctctg gttgaaatga tgtgggatct   3180
caagaagaaa ggattaatat attctatgga atttaccaat ctattgagca agaataccttt   3240
ttatctgttc acatttacta tctacactga tgaagtatac gattatctaa acactaataa   3300
```

| | |
|---|---|
| acttttttct gcaaaatgtt tagtcgtgtc tacaaaagga gatgtggaaa atttttcatc | 3360 |
| tctaaaaaaa gatgtggtca ttagagtttg actgcaggtc gactctagag gatccccggg | 3420 |
| cttatttatg attatttctc gctttcaatt taacacaacc ctcaagaacc tttgtattta | 3480 |
| ttttcaattt ttaggttggg taccagcggc ctcgagttag ttattatcta caggaacaaa | 3540 |
| tatagtatct gaaatcatat tcatatatcc cgttagaggt ctatgataat atatagtagc | 3600 |
| gtttgttccg ttatagacac cgaataatat tttacaaaag tgtatatacg tatcatcatc | 3660 |
| tttatgttta aaatttaaaa tcttaattcg taaatttaga gataaaatgg cttcttgtac | 3720 |
| aatactagtt aattctcccg tcctcgagct cttacttgta cagctcgtgc atgccgagag | 3780 |
| tgatcccggc ggcggtcacg aactccagca ggaccatgtg atcgcgcttc tcgttgggt | 3840 |
| ctttgctcag gcggactgg gtgctcaggt agtggttgtc gggcagcagc acggggccgt | 3900 |
| cgccgatggg ggtgttctgc tggtagtggt cggcgagctg cacgctgccg tcctcgatgt | 3960 |
| tgtggcggat cttgaagttc accttgatgc cgttcttctg cttgtcggcc atgatataga | 4020 |
| cgttgtggct gttgtagttg tactccagct tgtgccccag gatgttgccg tcctccttga | 4080 |
| agtcgatgcc cttcagctcg atgcggttca ccagggtgtc gccctcgaac ttcacctcgg | 4140 |
| cgcgggtctt gtagttgccg tcgtccttga agaagatggt gcgctcctgg acgtagcctt | 4200 |
| cgggcatggc ggacttgaag aagtcgtgct gcttcatgtg gtcggggtag cggctgaagc | 4260 |
| actgcacgcc gtaggtcagg gtggtcacga gggtgggcca gggcacgggc agcttgccgg | 4320 |
| tggtgcagat gaacttcagg gtcagcttgc cgtaggtggc atcgccctcg ccctcgccgg | 4380 |
| acacgctgaa cttgtggccg tttacgtcgc cgtccagctc gaccaggatg ggcaccaccc | 4440 |
| cggtgaacag ctcctcgccc ttgctcacca tttatagcat agaaaaaaac aaaatgaaag | 4500 |
| gcgcgcctta gttattatct acaggaacaa atatagtatc tgaaatcata ttcatatatc | 4560 |
| ccgttagagg tctatgataa tatatagtag cgtttgttcc gttatagaca ccgaataata | 4620 |
| ttttacaaaa gtgtatatac gtatcatcat ctttatgttt aaaatttaaa atcttaattc | 4680 |
| gtaaatttag agataaaatg gcttcttgta caatactagt taattctccc gtcctctcaa | 4740 |
| aattatccaa ctcctcagcg agaataggac ttagtacata aagtttagca tactctatca | 4800 |
| tcttcatata ataattggat aataatttat tccatgtttc tgtactaata tcgaacgagt | 4860 |
| ctatatattc ctttgtacgc catagaatat ccaaatttgt agggattata aacaaatctt | 4920 |
| cggggagtgt tagattaaac ttattagcgt acaatatata attatgtaga aattctgaat | 4980 |
| ctattcgctg tatagacttc atataagaca gatcatagaa atatacgtat gtcccaggga | 5040 |
| attc | 5044 |

<210> SEQ ID NO 4
<211> LENGTH: 2214
<212> TYPE: DNA
<213> ORGANISM: Human immunodeficiency virus type 1

<400> SEQUENCE: 4

| | |
|---|---|
| atgagagtga gggagacagt gaggaattat cagcacttgt ggagatgggg catcatgctc | 60 |
| cttgggatgt taatgatatg tagtgctgca gaccagctgg ggtcacagt gtattatggg | 120 |
| gtacctgtgt ggaaagaagc aaccactact ctattttgtg catcagatgc taaagcacat | 180 |
| aaagcagagg cacataatat ctgggctaca catgcctgtg taccaacaga ccccaatcca | 240 |
| cgagaaataa tactaggaaa tgtcacagaa aactttaaca tgtggaagaa taacatggta | 300 |

-continued

```
gagcagatgc atgaggatat aatcagttta tgggatcaaa gtctaaaacc atgtgtaaaa    360
ttaaccccac tctgtgttac tttaaactgc actacatatt ggaatggaac tttacagggg    420
aatgaaacta agggaagaa tagaagtgac ataatgacat gctctttcaa tataaccaca     480
gaaataagag gtagaaagaa gcaagaaact gcacttttct ataaacttga tgtggtacca    540
ctagaggata aggatagtaa taagactacc aactatagca gctatagatt aataaattgc    600
aatacctcag tcgtgacaca ggcgtgtcca aaagtaacct ttgagccaat tcccatacat    660
tattgtgccc cagctggatt tgcgattctg aaatgtaata ataagacgtt caatggaacg    720
ggtccatgca aaaatgtcag cacagtacag tgtacacatg gaattaggcc agtagtgtca    780
actcaactgt tgttgaatgg cagtctagca gaagaagaga taataattag atctgaaaat    840
atcacaaata atgcaaaaac cataaatagta cagcttaatg agtctgtaac aattgattgc    900
ataaggccca acaacaatac aagaaaaagt atacgcatag gaccagggca agcactctat    960
acaacagaca aataggggaa tataagacaa gcacattgta atgttagtaa agtaaaatgg   1020
ggaagaatgt taaaaagggt agctgaaaaa ttaaaagacc ttcttaacca gacaaagaac   1080
ataacttttg aaccatcctc aggaggggac ccagaaatta caacacacag ctttaattgt   1140
ggaggggaat tcttctactg caatacatca ggactattta tgggagtct gcttaatgag    1200 cagtttaatg agacatcaaa tgatactctc acactccaat gcagaataaa acaaattata   1260
aacatgtggc aaggagtagg aaaagcaatg tatgcccctc ccattgcagg accaatcagc   1320
tgttcatcaa atattacagg actattgttg acaagagatg gtggtaatac tggtaatgat   1380
tcagagatct tcagacctgg agggggagat atgagagaca attggagaag tgaattatac   1440
aaatataaag tagtaagaat tgaaccaatg ggtctagcac ccaccagggc aaaaagaaga   1500
gtggtggaaa gagaaaaaag agcaatagga ctgggagcta tgttccttgg gttcttggga   1560
gcggcaggaa gcacgatggg cgcagcgtca ctgacgctga cggtacaggc cagacagtta   1620
ttgtctggta tagtgcaaca gcaaaacaat ttgctgagag ctatagaggc gcaacagcat   1680
ctgttgcaac tcacagtctg ggcattaaa cagctccagg caagagtcct ggctatggaa    1740
agctacctaa aggatcaaca gctcctagga atttggggtt gctctggaaa acacatttgc   1800
accactactg tgccctggaa ctctacctgg agtaatagat ctgtagagga gatttggaat   1860
aatatgacct ggatgcagtg ggaaagagaa attgagaatt acacaggttt aatatacacc   1920
ttaattgaag aatcgcaaac ccagcaagaa aagaatgaac aagaactatt gcaattggat   1980
aaatgggcaa gtttgtggaa ttggtttagt ataacaaaat ggctgtggta tataaaaata   2040
ttcataatga tagtaggagg cttaataggt ttaagaatag ttttgctgt gctttcttta    2100 gtaaatagag ttaggcaggg atattcacct ctgtcttttc agaccctcct cccagccccg   2160
aggggacccg acaggcccga aggaatagaa gaagaaggtg gagagcaagg ctaa          2214
```

<210> SEQ ID NO 5
<211> LENGTH: 3068
<212> TYPE: DNA
<213> ORGANISM: Human immunodeficiency virus type 1

<400> SEQUENCE: 5

```
atgggtgcga gagcgtcagt attaagcgga ggaaaattag atgaatggga aaaaattcgg    60
ttacggccag gaggaaacaa aaaatataga ttaaaacatt tagtatgggc aagcagggag   120
ctagaacgat tcgcacttaa tcctggtctt ttagaaacat cagaaggctg tagacaaata   180
atagaacagc tacaaccatc tattcagaca ggatcagagg aacttaaatc attacataat   240
```

```
acagtagtaa ccctctattg tgtacatgaa aggataaagg tagcagatac caaggaagct    300
ttagataaga taaggaaga acaaaccaaa agtaagaaaa aagcacagca agcaacagct    360
gacagcagcc aggtcagcca aaattatcct atagtacaaa acctacaggg acaaatggta    420
caccagtcct tatcacctag gactttgaat gcatgggtaa agtaatagaa agagaaggct    480
ttcagcccag aagtaatacc catgttttca gcattatcag aaggagccac accaacagat    540
ttaaacacca tgctaaacac agtaggagga catcaagcag ccatgcaaat gttaaaagag    600
actatcaatg aggaagctgc agaatgggat aggctacatc cagtgcctgc agggcctgtt    660
gcaccaggcc aaatgagaga accaagagga agtgatatag caggaactac cagtacccct    720
caggaacaaa taggatggat gacaagcaat ccacctatcc cagtaggaga aatctataaa    780
agatggataa tcctaggatt aaataaaata gtaagaatgt atagccctgt cagcattttg    840
gacataagac aaggaccaaa ggaacccttt agagactatg tagatcggtt ctataaaact    900
ctacgagccg agcaagcttc acaggatgta aaaaattgga tgactgaaac cttgttagtc    960
caaaatgcga atccagattg taaaactatc ttaaaagcat tgggaccagc ggctacatta   1020
gaagaaatga tgacagcatg tcagggagtg ggggaccca gtcataaagc aagagttttg   1080
gctgaggcaa tgagccaagc atcaaacaca aatgctgtta atgatgcaga gagggcaat   1140 ttcaagggca agaaaatcat taagtgtttc aactgtggca agaaggaca cctagcaaaa   1200 aattgtaggg ctcctaggaa aagaggctgt tggaaatgtg gaaggaagg gcaccaaatg   1260 aaagattgta atgaaagaca ggctaatttt ttagggagaa tttggccttc ccacaagggg   1320
aggccaggga atttccttca gagcagacca gagccaacag ccccaccagc agagagcttc   1380
gggtttgggg aagagataac accctcccag aaacaggagg ggaaagagga gctgtatcct   1440
tcagcctccc tcaaatcact ctttggcaac gacccctagt cacaataaaa ataggggac   1500 agctaaagga agctctatta gatacaggag cagatgatac agtagtagaa gaaatgaatt   1560
tgccaggaaa atggaaacca aaaatgatag ggggaattgg gggctttatc aaagtaagac   1620
agtatgatca aatactcgta gaaatctatg gatataaggc tacaggtaca gtattagtag   1680
gacctacacc tgtcaacata attggaagaa atttgttgac tcagattggt tgcactttaa   1740
attttccaat tagtcctatt gaaactgtac cagtaaaatt aaagtcaggg atggatggtc   1800
caagagttaa acaatggcca ttgacagaag agaaaataaa agcactaata gaaatttgta   1860
cagaaatgga aaaggaagga aaactttcaa gaattggacc tgaaaatcca tacaatactc   1920
caatatttgc cataaagaaa aaagacagta ctaagtggag aaaattagta gatttcagag   1980
aacttaataa gagaactcaa gatttctggg aagttcaact aggaatacca catcctgcag   2040
ggctaaaaaa gaaaaaatca gtaacagtac tggaggtggg tgatgcatat ttttcagttc   2100
ccttatatga agactttaga aaatacactg cattcaccat acctagtata aacaatgaga   2160
caccaggaat tagatatcag tacaatgtgc ttccacaagg atggaaagga tcaccggcaa   2220
tattccaaag tagcatgaca aaaattttag aaccttttag aaaacaaaat ccagaagtgg   2280
ttatctacca atacatgcac gatttgtatg taggatctga cttagaaata gggcagcata   2340
gaataaaaat agaggaatta agggacacc tattgaagtg gggatttacc acaccagaca   2400
aaaatcatca gaaggaacct ccatttcttt ggatgggtta tgaactccat cctgataaat   2460
ggacagtaca gcctataaaa ctgccagaaa agaaagctg gactgtcaat gatctgcaga   2520
agttagtggg gaaattaaat tgggcaagtc aaatttattc aggaattaaa gtaagacaat   2580
```

```
tatgcaaatg ccttagggga accaaagcac tgacagaagt agtaccactg acagaagaag    2640
cagaattaga actggcagaa acagggaac ttctaaaaga aacagtacat ggagtgtatt     2700
atgacccatc aaaagactta atagcagaaa tacagaaaca agggcaagac caatggacat    2760
atcaaattta tcaagaacaa tataaaaatt tgaaaacagg aaagtatgca aagaggagga    2820
gtacccacac taatgatgta aaacaattaa cagaggcagt gcaaaaaata gcccaagaat    2880
gtatagtgat atggggaaag actcctaaat tcagactacc catacaaaag gaaacatggg    2940
aaacatggtg gacagagtat tggcaggcca cctggattcc tgagtgggag tttgtcaata    3000
cccctccctt ggttaaatta tggtaccagt tagagaagga acccatagta ggagcagaaa    3060
ccttctaa                                                             3068
```

<210> SEQ ID NO 6
<211> LENGTH: 9
<212> TYPE: PRT
<213> ORGANISM: Human immunodeficiency virus type 1

<400> SEQUENCE: 6

Ala Met Gln Met Leu Lys Glu Thr Ile
1               5

<210> SEQ ID NO 7
<211> LENGTH: 15
<212> TYPE: PRT
<213> ORGANISM: Human immunodeficiency virus type 1

<400> SEQUENCE: 7

Asp Thr Glu Val His Asn Val Trp Ala Thr His Ala Cys Val Pro
1               5                   10                  15

<210> SEQ ID NO 8
<211> LENGTH: 15
<212> TYPE: PRT
<213> ORGANISM: Human immunodeficiency virus type 1

<400> SEQUENCE: 8

Gln Gln Gln Ser Asn Leu Leu Arg Ala Ile Glu Ala Gln Gln His
1               5                   10                  15

<210> SEQ ID NO 9
<211> LENGTH: 13
<212> TYPE: PRT
<213> ORGANISM: Human immunodeficiency virus type 1

<400> SEQUENCE: 9

Glu Leu Arg Gln His Leu Leu Arg Trp Gly Leu Thr Thr
1               5                   10

<210> SEQ ID NO 10
<211> LENGTH: 14
<212> TYPE: PRT
<213> ORGANISM: Human immunodeficiency virus type 1

<400> SEQUENCE: 10

His Gly Val Tyr Tyr Asp Pro Ser Lys Asp Leu Ile Ala Glu
1               5                   10

<210> SEQ ID NO 11
<211> LENGTH: 1656
<212> TYPE: DNA
<213> ORGANISM: Vaccinia virus

<400> SEQUENCE: 11

```
atgacgtcgc ttcgcgaatt tagaaaatta tgctgtgata tatatcacgc atcaggatat    60
aaagaaaaat ctaaattaat tagagacttt ataacagata gggatgataa atatttgatc   120
attaagctat tgcttcccgg attagacgat agaatttata acatgaacga taaacaaatt   180
ataaaattat atagtataat atttaaacaa tctcaggaag atatgctaca agatttagga   240
tacggatata taggagacac tattaggact ttcttcaaag agaacacaga atccgtcca    300
cgagataaaa gcattttaac tttagaagaa gtggatagtt ttttaactac gttatcatcc   360
gtaactaaag aatcgcatca aataaaatta ttgactgata tcgcatccgt ttgtacatgt   420
aatgatttaa atgtgtagt catgcttatt gataaagatc taaaaattaa agcgggccct    480
cggtacgtac ttaacgctat tagtcctcat gcctatgatg tgtttagaaa atctaataac   540
ttgaaagaga taatagaaaa tgcatctaaa caaaatctag actctatatc tatttctgtt   600
atgactccaa ttaatcccat gttagcggaa tcgtgtgatt ctgtcaataa ggcgtttaaa   660
aaatttccat caggaatgtt tgcggaagtc aaatacgatg gtgaaagagt acaagttcat   720
aaaaataata acgagtttgc cttctttagt agaaacatga accagtact ctctcataaa     780
gtggattatc tcaaagaata cataccgaaa gcatttaaaa aagctacgtc tatcgtattg   840
gattctgaaa ttgttcttgt agacgaacat aatgtaccgc tcccgtttgg aagtttaggt   900
atacacaaaa agaaagaata taaaaactct aacatgtgtt tgttcgtgtt tgactgtttg   960
tactttgatg gattcgatat gacggacatt ccattgtacg aacgaagatc ttttctcaaa  1020
gatgttatgg ttgaaatacc aatagaata gtattctcag agttgacgaa tattagtaac   1080
gagtctcagt taactgacgt attggatgat gcactaacga gaaaattaga aggattggtc   1140
ttaaaagata ttaatggagt atacgaaccg ggaaagagaa gatggttaaa aataaagcga   1200
gactatttga acgagggttc catggcagat tctgccgatt tagtagtact aggtgcttac   1260
tatggtaaag gagcaaaggg tggtatcatg gcagtctttc taatgggttg ttacgacgat  1320
gaatccggta atggaagac ggttaccaag tgttcaggac acgatgataa tacgttaagg    1380
gagttgcaag accaattaaa gatgattaaa attaacaagg atcccaaaaa aattccagag  1440
tggttagtag ttaataaaat ctatattccc gattttgtag tagaggatcc aaaacaatct  1500
cagatatggg aaatttcagg agcagagttt acatcttcca gtcccatac cgcaaatgga   1560
atatccatta gatttcctag atttactagg ataagagagg ataaaacgtg gaaagaatct  1620
actcatctaa acgatttagt aaacttgact aaatct                             1656
```

<210> SEQ ID NO 12
<211> LENGTH: 552
<212> TYPE: PRT
<213> ORGANISM: Vaccinia virus

<400> SEQUENCE: 12

```
Met Thr Ser Leu Arg Glu Phe Arg Lys Leu Cys Cys Asp Ile Tyr His
1               5                   10                  15

Ala Ser Gly Tyr Lys Glu Lys Ser Lys Leu Ile Arg Asp Phe Ile Thr
            20                  25                  30

Asp Arg Asp Asp Lys Tyr Leu Ile Ile Lys Leu Leu Leu Pro Gly Leu
        35                  40                  45

Asp Asp Arg Ile Tyr Asn Met Asn Asp Lys Gln Ile Ile Lys Leu Tyr
    50                  55                  60

Ser Ile Ile Phe Lys Gln Ser Gln Glu Asp Met Leu Gln Asp Leu Gly
```

```
                65                  70                  75                  80
Tyr Gly Tyr Ile Gly Asp Thr Ile Arg Thr Phe Phe Lys Glu Asn Thr
                            85                  90                  95

Glu Ile Arg Pro Arg Asp Lys Ser Ile Leu Thr Leu Glu Glu Val Asp
                100                 105                 110

Ser Phe Leu Thr Thr Leu Ser Ser Val Thr Lys Glu Ser His Gln Ile
                115                 120                 125

Lys Leu Leu Thr Asp Ile Ala Ser Val Cys Thr Cys Asn Asp Leu Lys
                130                 135                 140

Cys Val Val Met Leu Ile Asp Lys Asp Leu Lys Ile Lys Ala Gly Pro
145                 150                 155                 160

Arg Tyr Val Leu Asn Ala Ile Ser Pro His Ala Tyr Asp Val Phe Arg
                165                 170                 175

Lys Ser Asn Asn Leu Lys Glu Ile Ile Glu Asn Ala Ser Lys Gln Asn
                180                 185                 190

Leu Asp Ser Ile Ser Ile Ser Val Met Thr Pro Ile Asn Pro Met Leu
                195                 200                 205

Ala Glu Ser Cys Asp Ser Val Asn Lys Ala Phe Lys Lys Phe Pro Ser
                210                 215                 220

Gly Met Phe Ala Glu Val Lys Tyr Asp Gly Glu Arg Val Gln Val His
225                 230                 235                 240

Lys Asn Asn Asn Glu Phe Ala Phe Phe Ser Arg Asn Met Lys Pro Val
                245                 250                 255

Leu Ser His Lys Val Asp Tyr Leu Lys Glu Tyr Ile Pro Lys Ala Phe
                260                 265                 270

Lys Lys Ala Thr Ser Ile Val Leu Asp Ser Glu Ile Val Leu Val Asp
                275                 280                 285

Glu His Asn Val Pro Leu Pro Phe Gly Ser Leu Gly Ile His Lys Lys
                290                 295                 300

Lys Glu Tyr Lys Asn Ser Asn Met Cys Leu Phe Val Phe Asp Cys Leu
305                 310                 315                 320

Tyr Phe Asp Gly Phe Asp Met Thr Asp Ile Pro Leu Tyr Glu Arg Arg
                325                 330                 335

Ser Phe Leu Lys Asp Val Met Val Glu Ile Pro Asn Arg Ile Val Phe
                340                 345                 350

Ser Glu Leu Thr Asn Ile Ser Asn Glu Ser Gln Leu Thr Asp Val Leu
                355                 360                 365

Asp Asp Ala Leu Thr Arg Lys Leu Glu Gly Leu Val Leu Lys Asp Ile
                370                 375                 380

Asn Gly Val Tyr Glu Pro Gly Lys Arg Arg Trp Leu Lys Ile Lys Arg
385                 390                 395                 400

Asp Tyr Leu Asn Glu Gly Ser Met Ala Asp Ser Ala Asp Leu Val Val
                405                 410                 415

Leu Gly Ala Tyr Tyr Gly Lys Gly Ala Lys Gly Gly Ile Met Ala Val
                420                 425                 430

Phe Leu Met Gly Cys Tyr Asp Asp Glu Ser Gly Lys Trp Lys Thr Val
                435                 440                 445

Thr Lys Cys Ser Gly His Asp Asp Asn Thr Leu Arg Glu Leu Gln Asp
                450                 455                 460

Gln Leu Lys Met Ile Lys Ile Asn Lys Asp Pro Lys Lys Ile Pro Glu
465                 470                 475                 480

Trp Leu Val Val Asn Lys Ile Tyr Ile Pro Asp Phe Val Val Glu Asp
                485                 490                 495
```

```
Pro Lys Gln Ser Gln Ile Trp Glu Ile Ser Gly Ala Glu Phe Thr Ser
            500                 505                 510

Ser Lys Ser His Thr Ala Asn Gly Ile Ser Ile Arg Phe Pro Arg Phe
        515                 520                 525

Thr Arg Ile Arg Glu Asp Lys Thr Trp Lys Ser Thr His Leu Asn
    530                 535                 540

Asp Leu Val Asn Leu Thr Lys Ser
545                 550

<210> SEQ ID NO 13
<211> LENGTH: 1656
<212> TYPE: DNA
<213> ORGANISM: Vaccinia virus

<400> SEQUENCE: 13
agatttagtc aagtttacta atcgtttag atgagtagat tctttccacg ttttatcctc      60
tcttatccta gtaaatctag gaaatctaat ggatattcca tttgcggtat gggacttgga     120
agatgtaaac tctgctcctg aaatttccca tatctgagat tgttttggat cctctactac    180
aaaatcggga atatagattt tattaactac taaccactct ggattttttt tgggatcctt    240
gttaatttta atcatcttta attggtcttg caactcccctt aacgtattat catcgtgtcc    300
tgaacacttg gtaaccgtct tccatttacc ggattcatcg tcgtaacaac ccattagaaa    360
gactgccatg ataccaccct tgctcctttt accatagtaa gcacctagta ctactaaatc    420
ggcagaatct gccatggaac cctcgttcaa atagtctcgc tttattttta accatcttct    480
ctttcccggt tcgtatactc cattaatatc ttttaagacc aatccttcta attttctcgt    540
tagtgcatca tccaatacgt cagttaactg agactcgtta ctaatattcg tcaactctga    600
gaatactatt ctattgggta tttcaaccat aacatctttg agaaagatc ttcgttcgta     660 caatggaatg tccgtcatat cgaatccatc aaagtacaaa cagtcaaaca cgaacaaaca    720
catgttagag ttttttatatt cttctttttt gtgtatacct aaacttccaa acgggagcgg    780
tacattatgt tcgtctacaa gaacaatttc agaatccaat acgatagacg tagcttttt     840 aaaatgctttc ggtatgtatt ctttgagata tccactttta tgagagagta ctggttttcat    900 gtttctacta aagaaggcaa actcgttatt atttttatga acttgtactc tttcaccatc    960
gtatttgact tccgcaaaca ttcctgatgg aaatttttta aacgcttat tgacagaatc   1020 acacgattcc gctaacatgg gattaattgg agtcataaca gaaatagata tagagtctag   1080
attttgttta gatgcatttt ctattatctc tttcaagtta ttagattttc taaacacatc   1140
ataggcatga ggactaatag cgttaagtac gtaccgaggg cccgctttaa ttttagatc    1200 tttatcaata agcatgacta cacatttaa atcattcat gtacaaacgg atgcgatatc   1260
agtcaataat tttatttgat gcgattcttt agttacggat gataacgtag ttaaaaaact   1320
atccacttct tctaaagtta aaatgctttt atctcgtgga cggatttctg tgttctcttt   1380
gaagaaagtc ctaatagtgt ctcctatata tccgtatcct aaatcttgta gcatatcttc   1440
ctgagattgt ttaaatatta tactatataa tttataatt tgtttatcgt tcatgttata   1500
aattctatcg tctaatccgg gaagcaatag cttaatgatc aaatatttat catccctatc   1560
tgttataaag tctctaatta atttagattt ttctttatat cctgatgcgt gatatatatc   1620
acagcataat tttctaaatt cgcgaagcga cgtcat                                1656

<210> SEQ ID NO 14
```

<211> LENGTH: 501
<212> TYPE: DNA
<213> ORGANISM: Vaccinia virus

<400> SEQUENCE: 14

```
ggagtatacg aaccgggaaa gagaagatgg ttaaaaataa agcgagacta tttgaacgag 60
ggttccatgg cagattctgc cgatttagta gtactaggtg cttactatgg taaaggagca 120
aagggtggta tcatggcagt ctttctaatg ggttgttacg acgatgaatc cggtaaatgg 180
aagacggtta ccaagtgttc aggacacgat gataatacgt taagggagtt gcaagaccaa 240
ttaaagatga ttaaaattaa caaggatccc aaaaaaattc cagagtggtt agtagttaat 300
aaaatctata ttcccgattt tgtagtagag gatccaaaac aatctcagat atgggaaatt 360
tcaggagcag agtttacatc ttccaagtcc cataccgcaa atggaatatc cattagattt 420
cctagattta ctaggataag agaggataaa acgtggaaag aatctactca tctaaacgat 480
ttagtaaact tgactaaatc t 501

<210> SEQ ID NO 15
<211> LENGTH: 501
<212> TYPE: DNA
<213> ORGANISM: Vaccinia virus
<400> SEQUENCE: 15
agatttagtc aagtttacta aatcgtttag atgagtagat tctttccacg ttttatcctc 60
tcttatccta gtaaatctag gaaatctaat ggatattcca tttgcggtat gggacttgga 120
agatgtaaac tctgctcctg aaatttccca tatctgagat tgttttggat cctctactac 180
aaaatcggga atatagattt tattaactac taaccactct ggaatttttt tgggatcctt 240
gttaatttta atcatcttta attggtcttg caactccctt aacgtattat catcgtgtcc 300
tgaacacttg gtaaccgtct tccatttacc ggattcatcg tcgtaacaac ccattagaaa 360
gactgccatg ataccaccct ttgctccttt accatagtaa gcacctagta ctactaaatc 420
ggcagaatct gccatggaac cctcgttcaa atagtctcgc tttattttta accatcttct 480
ctttcccggt tcgtatactc c 501

<210> SEQ ID NO 16
<211> LENGTH: 900
<212> TYPE: DNA
<213> ORGANISM: Vaccinia virus
<400> SEQUENCE: 16
atgaactttc aaggacttgt gttaactgac aattgcaaaa atcaatgggt cgttggacca 60
ttaataggaa aaggtggatt tggtagtatt tatactacta atgacaataa ttatgtagta 120
aaaatagagc ccaaagctaa cggatcatta tttaccgaac aggcatttta tactagagta 180
cttaaaccat ccgttatcga agaatggaaa aaatctcaca atataaagca cgtaggtctt 240
atcacgtgca aggcatttgg tctatacaaa tccattaatg tggaatatcg attcttggta 300
attaatagat taggtgcaga tctagatgcg gtgatcagag ccaataataa tagattacca 360
aaaaggtcgg tgatgttgat cggaatcgaa atcttaaata ccatacaatt tatgcacgag 420
caaggatatt ctcacggaga tattaaagcg agtaatatag tcttggatca aatagataag 480
aataaattat atctagtgga ttacggattg gtttctaaat tcatgtctaa tggcgaacat 540
gttccattta taagaaatcc aaataaaatg gataacggta ctctagaatt tacacctata 600
gattcgcata aaggatacgt tgtatctaga cgtggagatc tagaaacact tggatattgt 660
```

```
atgattagat ggttgggagg tatcttgcca tggactaaga tatctgaaac aaagaattgt    720
gcattagtaa gtgccacaaa acagaaatat gttaacaata ctgcgacttt gttaatgacc    780
agtttgcaat atgcacctag agaattgctg caatatatta ccatggtaaa ctctttgaca    840
tattttgagg aacccaatta cgacaagttt cggcacatat taatgcaggg tgtatattat    900
```

<210> SEQ ID NO 17
<211> LENGTH: 300
<212> TYPE: PRT
<213> ORGANISM: Vaccinia virus

<400> SEQUENCE: 17

```
Met Asn Phe Gln Gly Leu Val Leu Thr Asp Asn Cys Lys Asn Gln Trp
1               5                   10                  15

Val Val Gly Pro Leu Ile Gly Lys Gly Phe Gly Ser Ile Tyr Thr
            20                  25                  30

Thr Asn Asp Asn Asn Tyr Val Val Lys Ile Glu Pro Lys Ala Asn Gly
        35                  40                  45

Ser Leu Phe Thr Glu Gln Ala Phe Tyr Thr Arg Val Leu Lys Pro Ser
    50                  55                  60

Val Ile Glu Glu Trp Lys Lys Ser His Asn Ile Lys His Val Gly Leu
65                  70                  75                  80

Ile Thr Cys Lys Ala Phe Gly Leu Tyr Lys Ser Ile Asn Val Glu Tyr
                85                  90                  95

Arg Phe Leu Val Ile Asn Arg Leu Gly Ala Asp Leu Asp Ala Val Ile
            100                 105                 110

Arg Ala Asn Asn Asn Arg Leu Pro Lys Arg Ser Val Met Leu Ile Gly
        115                 120                 125

Ile Glu Ile Leu Asn Thr Ile Gln Phe Met His Glu Gln Gly Tyr Ser
    130                 135                 140

His Gly Asp Ile Lys Ala Ser Asn Ile Val Leu Asp Gln Ile Asp Lys
145                 150                 155                 160

Asn Lys Leu Tyr Leu Val Asp Tyr Gly Leu Val Ser Lys Phe Met Ser
                165                 170                 175

Asn Gly Glu His Val Pro Phe Ile Arg Asn Pro Asn Lys Met Asp Asn
            180                 185                 190

Gly Thr Leu Glu Phe Thr Pro Ile Asp Ser His Lys Gly Tyr Val Val
        195                 200                 205

Ser Arg Arg Gly Asp Leu Glu Thr Leu Gly Tyr Cys Met Ile Arg Trp
    210                 215                 220

Leu Gly Gly Ile Leu Pro Trp Thr Lys Ile Ser Glu Thr Lys Asn Cys
225                 230                 235                 240

Ala Leu Val Ser Ala Thr Lys Gln Lys Tyr Val Asn Asn Thr Ala Thr
                245                 250                 255

Leu Leu Met Thr Ser Leu Gln Tyr Ala Pro Arg Glu Leu Leu Gln Tyr
            260                 265                 270

Ile Thr Met Val Asn Ser Leu Thr Tyr Phe Glu Glu Pro Asn Tyr Asp
        275                 280                 285

Lys Phe Arg His Ile Leu Met Gln Gly Val Tyr Tyr
    290                 295                 300
```

<210> SEQ ID NO 18
<211> LENGTH: 900
<212> TYPE: DNA
<213> ORGANISM: Vaccinia virus -continued

<400> SEQUENCE: 18

```
ataatataca ccctgcatta atatgtgccg aaacttgtcg taattgggtt cctcaaaata 60
tgtcaaagag tttaccatgg taatatattg cagcaattct ctaggtgcat attgcaaact 120
ggtcattaac aaagtcgcag tattgttaac atatttctgt tttgtggcac ttactaatgc 180
acaattcttt gtttcagata tcttagtcca tggcaagata cctcccaacc atctaatcat 240
acaatatcca agtgtttcta gatctccacg tctagataca acgtatcctt tatgcgaatc 300
tataggtgta aattctagag taccgttatc cattttattt ggatttctta taaatggaac 360
atgttcgcca ttagacatga atttagaaac caatccgtaa tccactagat ataatttatt 420
cttatctatt tgatccaaga ctatattact cgctttaata tctccgtgag aatatccttg 480
ctcgtgcata aattgtatgg tatttaagat ttcgattccg atcaacatca ccgacctttt 540
tggtaatcta ttattattgg ctctgatcac cgcatctaga tctgcaccta atctattaat 600
taccaagaat cgatattcca cattaatgga tttgtataga ccaaatgcct tgcacgtgat 660
aagacctacg tgctttatat tgtgagattt tttccattct tcgataacgg atggtttaag 720
tactctagta taaaatgcct gttcggtaaa taatgatccg ttagctttgg gctctatttt 780
tactacataa ttattgtcat tagtagtata aatactacca aatccacctt ttcctattaa 840
tggtccaacg acccattgat tttgcaatt gtcagttaac acaagtcctt gaaagttcat 900

<210> SEQ ID NO 19
<211> LENGTH: 527
<212> TYPE: DNA
<213> ORGANISM: Vaccinia virus
<400> SEQUENCE: 19
atgaactttc aaggacttgt gttaactgac aattgcaaaa atcaatgggt cgttggacca 60
ttaataggaa aaggtggatt tggtagtatt tatactacta atgacaataa ttatgtagta 120
aaaatagagc ccaaagctaa cggatcatta tttaccgaac aggcatttta tactagagta 180
cttaaaccat ccgttatcga agaatggaaa aaatctcaca atataaagca cgtaggtctt 240
atcacgtgca aggcatttgg tctatacaaa tccattaatg tggaatatcg attcttggta 300
attaatagat taggtgcaga tctagatgcg gtgatcagag ccaataataa tagattacca 360
aaaaggtcgg tgatgttgat cggaatcgaa atcttaaata ccatacaatt tatgcacgag 420
caaggatatt ctcacggaga tattaaagcg agtaatatag tcttggatca aatagataag 480
aataaattat atctagtgga ttacggattg gtttctaaat tcatgtc 527

<210> SEQ ID NO 20
<211> LENGTH: 527
<212> TYPE: DNA
<213> ORGANISM: Vaccinia virus
<400> SEQUENCE: 20
gacatgaatt tagaaaccaa tccgtaatcc actagatata atttattctt atctatttga 60
tccaagacta tattactcgc tttaatatct ccgtgagaat atccttgctc gtgcataaat 120
tgtatggtat ttaagatttc gattccgatc aacatcaccg accttttttgg taatctatta 180
ttattggctc tgatcaccgc atctagatct gcacctaatc tattaattac caagaatcga 240
tattccacat taatggattt gtatagacca aatgccttgc acgtgataag acctacgtgc 300
tttatattgt gagatttttt ccattcttcg ataacggatg gtttaagtac tctagtataa 360
```

-continued aatgcctgtt cggtaaataa tgatccgtta gctttgggct ctatttttac tacataatta 420
ttgtcattag tagtataaat actaccaaat ccaccttttc ctattaatgg tccaacgacc 480
cattgatttt tgcaattgtc agttaacaca agtccttgaa agttcat 527

<210> SEQ ID NO 21
<211> LENGTH: 4903
<212> TYPE: DNA
<213> ORGANISM: Vaccinia virus

<400> SEQUENCE: 21
gaattcggag tatacgaacc gggaaagaga agatggttaa aaataaagcg agactatttg 60
aacgagggtt ccatggcaga ttctgccgat ttagtagtac taggtgctta ctatggtaaa 120
ggagcaaagg gtggtatcat ggcagtcttt ctaatgggtt gttacgacga tgaatccggt 180
aaatggaaga cggttaccaa gtgttcagga cacgatgata atacgttaag ggagttgcaa 240
gaccaattaa agatgattaa aattaacaag gatcccaaaa aaattccaga gtggttagta 300
gttaataaaa tctatattcc cgattttgta gtagaggatc caaaacaatc tcagatatgg 360
gaaatttcag gagcagagtt tacatcttcc aagtcccata ccgcaaatgg aatatccatt 420
agatttccta gatttactag gataagagag gataaaacgt ggaaagaatc tactcatcta 480
aacgatttag taaacttgac taaatcttaa tttttatggc gcgcctttca ttttgttttt 540
ttctatgcta taaatggtga gcaagggcga ggagctgttc accggggtgg tgcccatcct 600
ggtcgagctg gacggcgacg taaacggcca caagttcagc gtgtccggcg agggcgaggg 660
cgatgccacc tacggcaagc tgaccctgaa gttcatctgc accaccggca agctgcccgt 720
gccctggccc accctcgtga ccaccctgac ctacggcgtg cagtgcttca gccgctaccc 780
cgaccacatg aagcagcacg acttcttcaa gtccgccatg cccgaaggct acgtccagga 840
gcgcaccatc ttcttcaagg acgacggcaa ctacaagacc cgcgccgagg tgaagttcga 900
gggcgacacc ctggtgaacc gcatcgagct gaagggcatc gacttcaagg aggacggcaa 960
catcctgggg cacaagctgg agtacaacta caacagccac aacgtctata tcatggccga 1020
caagcagaag aacggcatca aggtgaactt caagatccgc cacaacatcg aggacggcag 1080
cgtgcagctc gccgaccact accagcagaa cacccccatc ggcgacggcc ccgtgctgct 1140
gcccgacaac cactacctga gcacccagtc cgccctgagc aaagacccca acgagaagcg 1200
cgatcacatg gtcctgctgg agttcgtgac cgccgccggg atcactctcg gcatgcacga 1260
gctgtacaag taagagctcc ccgattttgt agtagaggat ccaaaacaat ctcagatatg 1320
ggaaatttca ggagcagagt ttacatcttc caagtcccat accgcaaatg gaatatccat 1380
tagatttcct agatttacta ggataagaga ggataaaacg tggaaagaat ctactcatct 1440
aaacgattta gtaaacttga ctaaatctta atttttatct cgaggccgct ggtacccaac 1500
ctaaaaattg aaaataaata caaaggttct tgagggttgt gttaaattga aagcgagaaa 1560
taatcataaa taagcccggg gatcctctag agtcgacctg cagctaatgt attagttaaa 1620
tattaaaact taccacgtaa aacttaaaat ttaaaatgat atttcattga cagatagatc 1680
acacattatg aactttcaag gacttgtgtt aactgacaat tgcaaaaatc aatgggtcgt 1740
tggaccatta ataggaaaag gtggatttgg tagtatttat actactaatg acaataatta 1800
tgtagtaaaa atagagccca aagctaacgg atcattattt accgaacagg cattttatac 1860
tagagtactt aaaccatccg ttatcgaaga atggaaaaaa tctcacaata taaagcacgt 1920
aggtcttatc acgtgcaagg catttggtct atacaaatcc attaatgtgg aatatcgatt 1980

```
cttggtaatt aatagattag gtgcagatct agatgcggtg atcagagcca ataataatag   2040
attaccaaaa aggtcggtga tgttgatcgg aatcgaaatc ttaaatacca tacaatttat   2100
gcacgagcaa ggatattctc acggagatat aaagcgagt aatatagtct tggatcaaat    2160
agataagaat aaattatatc tagtggatta cggattggtt tctaaattca tgtcaagctt   2220
gtctccctat agtgagtcgt attagagctt ggcgtaatca tggtcatagc tgtttcctgt   2280
gtgaaattgt tatccgctca caattccaca acacatacga gccggaagca taaagtgtaa   2340
agcctggggt gcctaatgag tgagctaact cacattaatt gcgttgcgct cactgcccgc   2400
tttcgagtcg ggaaacctgt cgtgccagct gcattaatga atcggccaac gcgcggggag   2460
aggcggtttg cgtattgggc gctcttccgc ttcctcgctc actgactcgc tgcgctcggt   2520
cgttcggctg cggcgagcgg tatcagctca ctcaaaggcg gtaatacggt tatccacaga   2580
atcaggggat aacgcaggaa agaacatgtg agcaaaaggc cagcaaaagg ccaggaaccg   2640
taaaaaggcc gcgttgctgg cgttttttcga taggctccgc cccctgacg agcatcacaa     2700 aaatcgacgc tcaagtcaga ggtggcgaaa cccgacagga ctataaagat accaggcgtt   2760
tccccctgga agctccctcg tgcgctctcc tgttccgacc ctgccgctta ccggatacct    2820
gtccgccttt ctcccttcgg gaagcgtggc gctttctcat agctcacgct gtaggtatct   2880
cagttcggtg taggtcgttc gctccaagct gggctgtgtg cacgaacccc ccgttcagcc   2940
cgaccgctgc gccttatccg gtaactatcg tcttgagtcc aacccggtaa gacacgactt   3000
atcgccactg gcagcagcca ctggtaacag gattagcaga gcgaggtatg taggcggtgc   3060
tacagagttc ttgaagtggt ggcctaacta cggctacact agaaggacag tatttggtat   3120
ctgcgctctg ctgaagccag ttaccttcgg aaaaagagtt ggtagctctt gatccggcaa   3180
acaaaccacc gctggtagcg gtggttttt tgtttgcaag cagcagatta cgcgcagaaa   3240
aaaaggatct caagaagatc ctttgatctt ttctacgggg tctgacgctc agtggaacga   3300
aaactcacgt taagggattt tggtcatgag attatcaaaa aggatcttca cctagatcct   3360
tttaaattaa aaatgaagtt ttaaatcaat ctaaagtata tatgagtaaa cttggtctga   3420
cagttaccaa tgcttaatca gtgaggcacc tatctcagcg atctgtctat ttcgttcatc   3480
catagttgcc tgactccccg tcgtgtagat aactacgata cgggagggct taccatctgg   3540
ccccagtgct gcaatgatac cgcgagaccc acgctcaccg gctccagatt tatcagcaat   3600
aaaccagcca gccggaaggg ccgagcgcag aagtggtcct gcaactttat ccgcctccat   3660
ccagtctatt aattgttgcc gggaagctag agtaagtagt tcgccagtta atagtttgcg   3720
caacgttgtt ggcattgcta caggcatcgt ggtgtcacgc tcgtcgtttg gtatggcttc   3780
attcagctcc ggttcccaac gatcaaggcg agttacatga tcccccatgt tgtgcaaaaa   3840
agcggttagc tccttcggtc ctccgatcgt tgtcagaagt aagttggccg cagtgttatc   3900
actcatggtt atggcagcac tgcataattc tcttactgtc atgccatccg taagatgctt   3960
ttctgtgact ggtgagtact caaccaagtc attctgagaa tagtgtatgc ggcgaccgag   4020
ttgctcttgc ccggcgtcaa tacgggataa taccgcgcca catagcagaa ctttaaaagt   4080
gctcatcatt ggaaaacgtt cttcggggcg aaaactctca aggatcttac cgctgttgag   4140
atccagttcg atgtaaccca ctcgtgcacc caactgatct tcagcatctt ttactttcac   4200
cagcgtttct gggtgagcaa aaacaggaag gcaaaatgcc gcaaaaaagg gaataagggc   4260
gacacggaaa tgttgaatac tcatactctt cctttttcaa tattattgaa gcatttatca   4320
```

-continued

| | |
|---|---|
| gggttattgt ctcatgagcg gatacatatt tgaatgtatt tagaaaaata aacaaatagg | 4380 |
| ggttccgcgc acatttcccc gaaaagtgcc acctgacgtc taagaaacca ttattatcat | 4440 |
| gacattaacc tataaaaata ggcgtatcac gaggcccttt cgtctcgcgc gtttcggtga | 4500 |
| tgacggtgaa aacctctgac acatgcagct cccggagacg gtcacagctt gtctgtaagc | 4560 |
| ggatgccggg agcagacaag cccgtcaggg cgcgtcagcg ggtgttggcg ggtgtcgggg | 4620 |
| ctggcttaac tatgcggcat cagagcagat tgtactgaga gtgcaccata tgcggtgtga | 4680 |
| aataccgcac agatgcgtaa ggagaaaata ccgcatcagg cgccattcgc cattcaggct | 4740 |
| gcgcaactgt tgggaagggc gatcggtgcg ggcctcttcg ctattacgcc agctggcgaa | 4800 |
| agggggatgt gctgcaaggc gattaagttg ggtaacgcca gggttttccc agtcacgacg | 4860 |
| ttgtaaaacg acggccagtg aattggattt aggtgacact ata | 4903 |

<210> SEQ ID NO 22
<211> LENGTH: 4903
<212> TYPE: DNA
<213> ORGANISM: Vaccinia virus

<400> SEQUENCE: 22

```
tatagtgtca cctaaatcca attcactggc cgtcgtttta caacgtcgtg actgggaaaa     60
ccctggcgtt acccaactta atcgccttgc agcacatccc cctttcgcca gctggcgtaa    120
tagcgaagag gcccgcaccg atcgcccttc ccaacagttg cgcagcctga atggcgaatg    180
gcgcctgatg cggtattttc tccttacgca tctgtgcggt atttcacacc gcatatggtg    240
cactctcagt acaatctgct ctgatgccgc atagttaagc cagccccgac acccgccaac    300
acccgctgac gcgccctgac gggcttgtct gctcccggca tccgcttaca gacaagctgt    360
gaccgtctcc gggagctgca tgtgtcagag gttttcaccg tcatcaccga aacgcgcgag    420
acgaaagggc ctcgtgatac gcctattttt ataggttaat gtcatgataa taatggtttc    480
ttagacgtca ggtggcactt ttcggggaaa tgtgcgcgga acccctattt gtttattttt    540
ctaaatacat tcaaatatgt atccgctcat gagacaataa ccctgataaa tgcttcaata    600
atattgaaaa aggaagagta tgagtattca acatttccgt gtcgccctta ttcccttttt    660
tgcggcattt tgccttcctg tttttgctca cccagaaacg ctggtgaaag taaaagatgc    720
tgaagatcag ttgggtgcac gagtgggtta catcgaactg gatctcaaca gcggtaagat    780
ccttgagagt tttcgccccg aagaacgttt tccaatgatg agcactttta aagttctgct    840
atgtggcgcg gtattatccc gtattgacgc cgggcaagag caactcggtc gccgcataca    900
ctattctcag aatgacttgg ttgagtactc accagtcaca gaaaagcatc ttacggatgg    960
catgacagta agagaattat gcagtgctgc cataaccatg agtgataaca ctgcggccaa   1020
cttacttctg acaacgatcg gaggaccgaa ggagctaacc gcttttttgc acaacatggg   1080
ggatcatgta actcgccttg atcgttggga accggagctg aatgaagcca taccaaacga   1140
cgagcgtgac accacgatgc ctgtagcaat ggcaacaacg ttgcgcaaac tattaactgg   1200
cgaactactt actctagctt cccggcaaca attaatagac tggatggagg cggataaagt   1260
tgcaggacca cttctgcgct cggcccttcc ggctggctgg tttattgctg ataaatctgg   1320
agccggtgag cgtgggtctc gcggtatcat tgcagcactg gggccagatg gtaagccctc   1380
ccgtatcgta gttatctaca cgacggggag tcaggcaact atggatgaac gaaatagaca   1440
gatcgctgag ataggtgcct cactgattaa gcattggtaa ctgtcagacc aagtttactc   1500
atatatactt tagattgatt taaaacttca tttttaattt aaaaggatct aggtgaagat   1560
```

```
ccttttttgat aatctcatga ccaaaatccc ttaacgtgag ttttcgttcc actgagcgtc    1620
agaccccgta gaaaagatca aaggatcttc ttgagatcct ttttttctgc gcgtaatctg    1680
ctgcttgcaa acaaaaaaac caccgctacc agcggtggtt tgtttgccgg atcaagagct    1740
accaactctt tttccgaagg taactggctt cagcagagcg cagataccaa atactgtcct    1800
tctagtgtag ccgtagttag gccaccactt caagaactct gtagcaccgc ctacatacct    1860
cgctctgcta atcctgttac cagtggctgc tgccagtggc gataagtcgt gtcttaccgg    1920
gttggactca agacgatagt taccggataa ggcgcagcgg tcgggctgaa cggggggttc    1980
gtgcacacag cccagcttgg agcgaacgac ctacaccgaa ctgagatacc tacagcgtga    2040
gctatgagaa agcgccacgc ttcccgaagg gagaaaggcg gacaggtatc cggtaagcgg    2100
cagggtcgga acaggagagc gcacgaggga gcttccaggg ggaaacgcct ggtatcttta    2160
tagtcctgtc gggtttcgcc acctctgact tgagcgtcga ttttttgtgat gctcgtcagg    2220 ggggcggagc ctatcgaaaa acgccagcaa cgcggccttt ttacggttcc tggccttttg    2280
ctggcctttt gctcacatgt tctttcctgc gttatcccct gattctgtgg ataaccgtat    2340
taccgccttt gagtgagctg ataccgctcg ccgcagccga acgaccgagc gcagcgagtc    2400
agtgagcgag gaagcggaag agcgcccaat acgcaaaccg cctctccccg cgcgttggcc    2460
gattcattaa tgcagctggc acgacaggtt cccgactcg aaagcgggca gtgagcgcaa    2520
cgcaattaat gtgagttagc tcactcatta ggcaccccag gctttacact ttatgcttcc    2580
ggctcgtatg ttgtgtggaa ttgtgagcgg ataacaattt cacacaggaa acagctatga    2640
ccatgattac gccaagctct aatacgactc actatagggg acaagcttg acatgaattt    2700 agaaaccaat ccgtaatcca ctagatataa tttattctta tctatttgat ccaagactat    2760
attactcgct ttaatatctc cgtgagaata tccttgctcg tgcataaatt gtatggtatt    2820
taagatttcg attccgatca acatcaccga ccttttggt aatctattat tattggctct    2880
gatcaccgca tctagatctg cacctaatct attaattacc aagaatcgat attccacatt    2940
aatggatttg tatagaccaa atgccttgca cgtgataaga cctacgtgct ttatattgtg    3000 agatttttc cattcttcga taacggatgg tttaagtact ctagtataaa atgcctgttc    3060
ggtaaataat gatccgttag ctttgggctc tatttttact acataattat tgtcattagt    3120
agtataaata ctaccaaatc caccttttcc tattaatggt ccaacgaccc attgattttt    3180
gcaattgtca gttaacacaa gtccttgaaa gttcataatg tgtgatctat ctgtcaatga    3240
aatatcattt taaattttaa gttttacgtg gtaagtttta atatttaact aatacattag    3300
ctgcaggtcg actctagagg atccccgggc ttatttatga ttatttctcg ctttcaattt    3360
aacacaaccc tcaagaacct ttgtatttat tttcaatttt taggttgggt accagcggcc    3420
tcgagataaa aattaagatt tagtcaagtt tactaaatcg tttagatgag tagattctt    3480 ccacgtttta tcctctctta tcctagtaaa tctaggaaat ctaatggata ttccatttgc    3540
ggtatgggac ttggaagatg taaactctgc tcctgaaatt tcccatatct gagattgttt    3600
tggatcctct actacaaaat cggggagctc ttacttgtac agctcgtgca tgccgagagt    3660
gatcccggcg gcggtcacga actccagcag gaccatgtga tcgcgcttct cgttgggtc    3720 tttgctcagg gcggactggg tgctcaggta gtggttgtcg ggcagcagca cggggccgtc    3780
gccgatgggg gtgttctgct ggtagtggtc ggcgagctgc acgctgccgt cctcgatgtt    3840
gtggcggatc ttgaagttca ccttgatgcc gttcttctgc ttgtcggcca tgatatagac    3900
```

| | |
|---|---|
| gttgtggctg ttgtagttgt actccagctt gtgccccagg atgttgccgt cctccttgaa | 3960 |
| gtcgatgccc ttcagctcga tgcggttcac cagggtgtcg ccctcgaact tcacctcggc | 4020 |
| gcgggtcttg tagttgccgt cgtccttgaa gaagatggtg cgctcctgga cgtagccttc | 4080 |
| gggcatggcg gacttgaaga agtcgtgctg cttcatgtgg tcggggtagc ggctgaagca | 4140 |
| ctgcacgccg taggtcaggg tggtcacgag ggtgggccag ggcacgggca gcttgccggt | 4200 |
| ggtgcagatg aacttcaggg tcagcttgcc gtaggtggca tcgccctcgc cctgccgga | 4260 |
| cacgctgaac ttgtggccgt ttacgtcgcc gtccagctcg accaggatgg gcaccacccc | 4320 |
| ggtgaacagc tcctcgccct tgctcaccat ttatagcata gaaaaaaaca aaatgaaagg | 4380 |
| cgcgccataa aaattaagat ttagtcaagt ttactaaatc gtttagatga gtagattctt | 4440 |
| tccacgtttt atcctctctt atcctagtaa atctaggaaa tctaatggat attccatttg | 4500 |
| cggtatggga cttggaagat gtaaactctg ctcctgaaat ttcccatatc tgagattgtt | 4560 |
| ttggatcctc tactacaaaa tcgggaatat agattttatt aactactaac cactctggaa | 4620 |
| ttttttttggg atccttgtta attttaatca tctttaattg gtcttgcaac tcccttaacg | 4680 |
| tattatcatc gtgtcctgaa cacttggtaa ccgtcttcca tttaccggat tcatcgtcgt | 4740 |
| aacaacccat tagaaagact gccatgatac caccctttgc tcctttacca tagtaagcac | 4800 |
| ctagtactac taaatcggca gaatctgcca tggaaccctc gttcaaatag tctcgcttta | 4860 |
| tttttaacca tcttctcttt cccggttcgt atactccgaa ttc | 4903 |

<210> SEQ ID NO 23
<211> LENGTH: 189
<212> TYPE: DNA
<213> ORGANISM: Vaccinia virus

<400> SEQUENCE: 23

| | |
|---|---|
| cccgattttg tagtagagga tccaaaacaa tctcagatat gggaaatttc aggagcagag | 60 |
| tttacatctt ccaagtccca taccgcaaat ggaatatcca ttagatttcc tagatttact | 120 |
| aggataagag aggataaaac gtggaaagaa tctactcatc taaacgattt agtaaacttg | 180 |
| actaaatct | 189 |

<210> SEQ ID NO 24
<211> LENGTH: 84
<212> TYPE: DNA
<213> ORGANISM: Vaccinia virus

<400> SEQUENCE: 24

| | |
|---|---|
| ctaatgtatt agttaaatat taaaacttac cacgtaaaac ttaaaattta aaatgatatt | 60 |
| tcattgacag atagatcaca catt | 84 |

<210> SEQ ID NO 25
<211> LENGTH: 42
<212> TYPE: DNA
<213> ORGANISM: Artificial Sequence
<220> FEATURE:
<223> OTHER INFORMATION: Synthetic Primer

<400> SEQUENCE: 25

| | |
|---|---|
| cagatcgaat tcggagtata cgaaccggga aagagaagat gg | 42 |

<210> SEQ ID NO 26
<211> LENGTH: 62
<212> TYPE: DNA
<213> ORGANISM: Artificial Sequence -continued
<220> FEATURE:
<223> OTHER INFORMATION: Synthetic Primer

<400> SEQUENCE: 26
cagatcggcg cgccataaaa attaagattt agtcaagttt actaaatcgt ttagatgagt    60
ag                                                                  62

<210> SEQ ID NO 27
<211> LENGTH: 44
<212> TYPE: DNA
<213> ORGANISM: Artificial Sequence
<220> FEATURE:
<223> OTHER INFORMATION: Synthetic Primer

<400> SEQUENCE: 27
catcaggagc tccccgattt tgtagtagag gatccaaaac aatc                    44

<210> SEQ ID NO 28
<211> LENGTH: 60
<212> TYPE: DNA
<213> ORGANISM: Artificial Sequence
<220> FEATURE:
<223> OTHER INFORMATION: Synthetic Primer

<400> SEQUENCE: 28
cagatcctcg agataaaaat taagatttag tcaagtttac taaatcgttt agatgagtag    60

<210> SEQ ID NO 29
<211> LENGTH: 46
<212> TYPE: DNA
<213> ORGANISM: Artificial Sequence
<220> FEATURE:
<223> OTHER INFORMATION: Synthetic Primer

<400> SEQUENCE: 29
cagatcctgc agctaatgta ttagttaaat attaaaactt accacg                  46

<210> SEQ ID NO 30
<211> LENGTH: 42
<212> TYPE: DNA
<213> ORGANISM: Artificial Sequence
<220> FEATURE:
<223> OTHER INFORMATION: Synthetic Primer

<400> SEQUENCE: 30
catgcaaagc ttgacatgaa tttagaaacc aatccgtaat cc                      42

<210> SEQ ID NO 31
<211> LENGTH: 439
<212> TYPE: PRT
<213> ORGANISM: Vaccinia virus

<400> SEQUENCE: 31

Met Gly Val Ala Asn Asp Ser Ser Pro Glu Tyr Gln Trp Met Ser Pro
1               5                   10                  15

His Arg Leu Ser Asp Thr Val Ile Leu Gly Asp Cys Leu Tyr Phe Asn
            20                  25                  30

Asn Ile Met Ser Gln Leu Asp Leu His Gln Asn Trp Ala Pro Ser Val
        35                  40                  45

Arg Leu Leu Asn Tyr Phe Lys Asn Phe Asn Lys Glu Thr Leu Leu Lys
    50                  55                  60

Ile Glu Glu Asn Asp Tyr Ile Asn Ser Ser Phe Phe Gln Gln Lys Asp
65                  70                  75                  80

```
Lys Arg Phe Tyr Pro Ile Asn Asp Asp Phe Tyr His Ile Ser Thr Gly
                 85                  90                  95
Gly Tyr Gly Ile Val Phe Lys Ile Asp Asn Tyr Val Val Lys Phe Val
            100                 105                 110
Phe Glu Ala Thr Lys Leu Tyr Ser Pro Met Glu Thr Thr Ala Glu Phe
        115                 120                 125
Thr Val Pro Lys Phe Leu Tyr Asn Asn Leu Lys Gly Asp Glu Lys Lys
130                 135                 140
Leu Ile Val Cys Ala Trp Ala Met Gly Leu Asn Tyr Lys Leu Thr Phe
145                 150                 155                 160
Leu His Thr Leu Tyr Lys Arg Val Leu His Met Leu Leu Leu Leu Ile
                165                 170                 175
Gln Thr Met Asp Gly Gln Glu Leu Ser Leu Arg Tyr Ser Ser Lys Val
            180                 185                 190
Phe Leu Lys Ala Phe Asn Glu Arg Lys Asp Ser Ile Lys Phe Val Lys
        195                 200                 205
Leu Leu Ser His Phe Tyr Pro Ala Val Ile Asn Ser Asn Ile Asn Val
210                 215                 220
Ile Asn Tyr Phe Asn Arg Met Phe His Phe Glu His Glu Lys Arg
225                 230                 235                 240
Thr Asn Tyr Glu Tyr Glu Arg Gly Asn Ile Ile Ile Phe Pro Leu Ala
                245                 250                 255
Leu Tyr Ser Ala Asp Lys Val Asp Thr Glu Leu Ala Ile Lys Leu Gly
            260                 265                 270
Phe Lys Ser Leu Val Gln Tyr Ile Lys Phe Ile Phe Leu Gln Met Ala
        275                 280                 285
Leu Leu Tyr Ile Lys Ile Tyr Glu Leu Pro Cys Cys Asp Asn Phe Leu
290                 295                 300
His Ala Asp Leu Lys Pro Asp Asn Ile Leu Leu Phe Asp Ser Asn Glu
305                 310                 315                 320
Pro Ile Ile Ile His Leu Lys Asp Lys Lys Phe Val Phe Asn Glu Arg
                325                 330                 335
Ile Lys Ser Ala Leu Asn Asp Phe Asp Phe Ser Gln Val Ala Gly Ile
            340                 345                 350
Ile Asn Lys Lys Ile Lys Asn Asn Phe Lys Val Lys His Asn Trp Tyr
        355                 360                 365
Tyr Asp Phe His Phe Val His Thr Leu Lys Thr Tyr Pro Glu
370                 375                 380
Ile Glu Lys Asp Ile Glu Phe Ser Thr Ala Leu Glu Glu Phe Ile Met
385                 390                 395                 400
Cys Thr Lys Thr Asp Cys Asp Lys Tyr Arg Leu Lys Val Ser Ile Leu
                405                 410                 415
His Pro Ile Ser Phe Leu Glu Lys Phe Ile Met Arg Asp Ile Phe Ser
            420                 425                 430
Asp Trp Ile Asn Gly Gly Asn
        435
```

<210> SEQ ID NO 32
<211> LENGTH: 635
<212> TYPE: PRT
<213> ORGANISM: Vaccinia virus

<400> SEQUENCE: 32

Met Leu Asn Arg Ile Gln Thr Leu Met Lys Thr Ala Asn Asn Tyr Glu

-continued

```
1               5                   10                  15
Thr Ile Glu Ile Leu Arg Asn Tyr Leu Arg Leu Tyr Ile Ile Leu Ala
                20                  25                  30
Arg Asn Glu Glu Gly His Gly Ile Leu Ile Tyr Asp Asp Asn Ile Asp
                35                  40                  45
Ser Val Met Ser Met Met Asn Ile Thr Ile Leu Glu Val Ile Gly Leu
                50                  55                  60
Thr Thr His Cys Thr Lys Leu Arg Ser Ser Pro Pro Ile Pro Met Ser
65              70                  75                  80
Arg Leu Phe Met Asp Glu Ile Asp His Glu Ser Tyr Tyr Ser Pro Lys
                85                  90                  95
Thr Ser Asp Tyr Pro Leu Ile Asp Ile Ile Arg Lys Arg Ser His Glu
                100                 105                 110
Gln Gly Asp Ile Ala Leu Ala Leu Glu Arg Tyr Gly Ile Glu Asn Thr
                115                 120                 125
Asp Ser Ile Ser Glu Ile Asn Glu Trp Leu Ser Ser Lys Gly Leu Ala
                130                 135                 140
Cys Tyr Arg Phe Val Lys Phe Asn Asp Tyr Arg Lys Gln Met Tyr Arg
145             150                 155                 160
Lys Phe Ser Arg Cys Thr Ile Val Asp Ser Met Ile Gly His Ile
                165                 170                 175
Gly His His Tyr Ile Trp Ile Lys Asn Leu Glu Thr Tyr Thr Arg Pro
                180                 185                 190
Glu Ile Asp Val Leu Pro Phe Asp Ile Lys Tyr Ile Ser Arg Asp Glu
                195                 200                 205
Leu Trp Ala Arg Ile Ser Ser Leu Asp Gln Thr His Ile Lys Thr
                210                 215                 220
Ile Ala Val Ser Val Tyr Gly Ala Ile Thr Asp Asn Gly Pro Ile Pro
225             230                 235                 240
Tyr Met Ile Ser Thr Tyr Pro Gly Asn Thr Phe Val Asn Phe Asn Ser
                245                 250                 255
Val Lys Asn Leu Ile Leu Asn Phe Leu Asp Trp Ile Lys Asp Ile Met
                260                 265                 270
Thr Ser Thr Arg Thr Ile Ile Leu Val Gly Tyr Met Ser Asn Leu Phe
                275                 280                 285
Asp Ile Pro Leu Leu Thr Val Tyr Trp Pro Asn Asn Cys Gly Trp Lys
                290                 295                 300
Ile Tyr Asn Asn Thr Leu Ile Ser Ser Asp Gly Ala Arg Val Ile Trp
305             310                 315                 320
Met Asp Ala Tyr Lys Phe Ser Cys Gly Leu Ser Leu Gln Asp Tyr Cys
                325                 330                 335
Tyr His Trp Gly Ser Lys Pro Glu Ser Arg Pro Phe Asp Leu Ile Lys
                340                 345                 350
Lys Ser Asp Ala Lys Arg Asn Ser Lys Ser Leu Val Lys Glu Ser Met
                355                 360                 365
Ala Ser Leu Lys Ser Leu Tyr Glu Ala Phe Glu Thr Gln Ser Gly Ala
                370                 375                 380
Leu Glu Val Leu Met Ser Pro Cys Arg Met Phe Ser Phe Ser Arg Ile
385             390                 395                 400
Glu Asp Met Phe Leu Thr Ser Val Ile Asn Arg Val Ser Glu Asn Thr
                405                 410                 415
Gly Met Gly Met Tyr Tyr Pro Thr Asn Asp Ile Pro Ser Leu Phe Ile
                420                 425                 430
```

```
Glu Ser Ser Ile Cys Leu Asp Tyr Ile Ile Val Asn Gln Glu Ser
        435                 440                 445

Asn Lys Tyr Arg Ile Lys Ser Val Leu Asp Ile Ile Ser Ser Lys Gln
450                 455                 460

Tyr Pro Ala Gly Arg Pro Asn Tyr Val Lys Asn Gly Thr Lys Gly Lys
465                 470                 475                 480

Leu Tyr Ile Ala Leu Cys Lys Val Thr Val Pro Thr Asn Asp His Ile
                485                 490                 495

Pro Val Val Tyr His Asp Asp Asn Thr Thr Thr Phe Ile Thr Val
                500                 505                 510

Leu Thr Ser Val Asp Ile Glu Thr Ala Ile Arg Ala Gly Tyr Ser Ile
                515                 520                 525

Val Glu Leu Gly Ala Leu Gln Trp Asp Asn Asn Ile Pro Glu Leu Lys
530                 535                 540

Asn Gly Leu Leu Asp Ser Ile Lys Met Ile Tyr Asp Leu Asn Ala Val
545                 550                 555                 560

Thr Thr Asn Asn Leu Leu Glu Gln Leu Ile Glu Asn Ile Asn Phe Asn
                565                 570                 575

Asn Ser Ser Ile Ile Ser Leu Phe Tyr Thr Phe Ala Ile Ser Tyr Cys
                580                 585                 590

Arg Ala Phe Ile Tyr Ser Ile Met Glu Thr Ile Asp Pro Val Tyr Ile
                595                 600                 605

Ser Gln Phe Ser Tyr Lys Glu Leu Tyr Val Ser Ser Tyr Lys Asp
                610                 615                 620

Ile Asn Glu Ser Met Ser Gln Met Val Lys Leu
625                 630                 635

<210> SEQ ID NO 33
<211> LENGTH: 372
<212> TYPE: PRT
<213> ORGANISM: Vaccinia virus

<400> SEQUENCE: 33

Met Trp Pro Phe Ala Pro Val Pro Ala Gly Ala Lys Cys Arg Leu Val
1               5                   10                  15

Glu Thr Leu Pro Glu Asn Met Asp Phe Arg Ser Asp His Leu Thr Thr
                20                  25                  30

Phe Glu Cys Phe Asn Glu Ile Ile Thr Leu Ala Lys Lys Tyr Ile Tyr
            35                  40                  45

Ile Ala Ser Phe Cys Cys Asn Pro Leu Ser Thr Thr Arg Gly Ala Leu
50                  55                  60

Ile Phe Asp Lys Leu Lys Glu Ala Ser Glu Lys Gly Ile Lys Ile Ile
65                  70                  75                  80

Val Leu Leu Asp Glu Arg Gly Lys Arg Asn Leu Gly Glu Leu Gln Ser
                85                  90                  95

His Cys Pro Asp Ile Asn Phe Ile Thr Val Asn Ile Asp Lys Lys Asn
                100                 105                 110

Asn Val Gly Leu Leu Leu Gly Cys Phe Trp Val Ser Asp Asn Glu Arg
            115                 120                 125

Cys Tyr Val Gly Asn Ala Ser Phe Thr Gly Gly Ser Ile His Thr Ile
            130                 135                 140

Lys Thr Leu Gly Val Tyr Ser Asp Tyr Pro Pro Leu Ala Thr Asp Leu
145                 150                 155                 160

Arg Arg Arg Phe Asp Thr Phe Lys Ala Phe Asn Ser Ala Lys Asn Ser
```

```
                165                 170                 175
Trp Leu Asn Leu Cys Ser Ala Ala Cys Cys Leu Pro Val Ser Thr Ala
            180                 185                 190

Tyr His Ile Lys Asn Pro Ile Gly Gly Val Phe Phe Thr Asp Ser Pro
        195                 200                 205

Glu His Leu Leu Gly Tyr Ser Arg Asp Leu Asp Thr Asp Val Val Ile
    210                 215                 220

Asp Lys Leu Lys Ser Ala Lys Thr Ser Ile Asp Ile Glu His Leu Ala
225                 230                 235                 240

Ile Val Pro Thr Thr Arg Val Asp Gly Asn Ser Tyr Tyr Trp Pro Asp
                245                 250                 255

Ile Tyr Asn Ser Ile Ile Glu Ala Ala Ile Asn Arg Gly Val Lys Ile
            260                 265                 270

Arg Leu Leu Val Gly Asn Trp Asp Lys Asn Asp Val Tyr Ser Met Ala
        275                 280                 285

Thr Ala Arg Ser Leu Asp Ala Leu Cys Val Gln Asn Asp Leu Ser Val
    290                 295                 300

Lys Val Phe Thr Ile Gln Asn Asn Thr Lys Leu Leu Ile Val Asp Asp
305                 310                 315                 320

Glu Tyr Val His Ile Thr Ser Ala Asn Phe Asp Gly Thr His Tyr Gln
                325                 330                 335

Asn His Gly Phe Val Ser Phe Asn Ser Ile Asp Lys Gln Leu Val Ser
            340                 345                 350

Glu Ala Lys Lys Ile Phe Glu Arg Asp Trp Val Ser Ser His Ser Lys
        355                 360                 365

Ser Leu Lys Ile
    370

<210> SEQ ID NO 34
<211> LENGTH: 158
<212> TYPE: PRT
<213> ORGANISM: Vaccinia virus

<400> SEQUENCE: 34

Met Arg Ser Ile Ala Gly Leu His Lys Leu Lys Met Glu Ile Phe Asn
1               5                   10                  15

Val Glu Glu Leu Ile Asn Met Lys Pro Phe Lys Asn Met Asn Lys Ile
            20                  25                  30

Thr Ile Asn Gln Asn Asp Asn Cys Ile Leu Ala Asn Arg Cys Phe Val
        35                  40                  45

Lys Ile Asp Thr Pro Arg Tyr Ile Pro Ser Thr Ile Ser Ser Ser
    50                  55                  60

Asn Ile Ile Arg Ile Arg Asn His Asp Phe Thr Leu Ser Glu Leu Leu
65                  70                  75                  80

Tyr Ser Pro Phe His Phe Gln Gln Pro Gln Phe Gln Tyr Leu Leu Pro
                85                  90                  95

Gly Phe Val Leu Thr Cys Ile Asp Lys Val Ser Lys Gln Gln Lys Lys
            100                 105                 110

Cys Lys Tyr Cys Ile Ser Asn Arg Gly Asp Asp Asp Ser Leu Ser Ile
        115                 120                 125

Asn Leu Phe Ile Pro Thr Ile Asn Lys Ser Ile Tyr Ile Ile Ile Gly
    130                 135                 140

Leu Arg Met Lys Asn Phe Trp Lys Pro Lys Phe Glu Ile Glu
145                 150                 155
```

```
<210> SEQ ID NO 35
<211> LENGTH: 101
<212> TYPE: PRT
<213> ORGANISM: Vaccinia virus

<400> SEQUENCE: 35

Met Asn Ser His Phe Ala Ser Ala His Thr Pro Phe Tyr Ile Asn Thr
1               5                   10                  15

Lys Glu Gly Arg Tyr Leu Val Leu Lys Ala Val Lys Val Cys Asp Val
            20                  25                  30

Arg Thr Val Glu Cys Glu Gly Ser Lys Ala Ser Cys Val Leu Lys Val
        35                  40                  45

Asp Lys Pro Ser Ser Pro Ala Cys Glu Arg Arg Pro Ser Ser Pro Ser
    50                  55                  60

Arg Cys Glu Arg Met Asn Asn Pro Gly Lys Gln Val Pro Phe Met Arg
65                  70                  75                  80

Thr Asp Met Leu Gln Asn Met Phe Ala Ala Asn Arg Asp Asn Val Ala
                85                  90                  95

Ser Arg Leu Leu Ser
            100

<210> SEQ ID NO 36
<211> LENGTH: 259
<212> TYPE: PRT
<213> ORGANISM: Vaccinia virus

<400> SEQUENCE: 36

Met Glu Asn Val Tyr Ile Ser Ser Tyr Ser Ser Asn Glu Gln Thr Ser
1               5                   10                  15

Met Ala Val Ala Ala Thr Asp Ile Arg Glu Leu Leu Ser Gln Tyr Val
            20                  25                  30

Asp Asp Ala Asn Leu Glu Asp Leu Ile Glu Trp Ala Met Glu Lys Ser
        35                  40                  45

Ser Lys Tyr Tyr Ile Lys Asn Ile Gly Asn Thr Lys Ser Asn Ile Glu
    50                  55                  60

Glu Thr Lys Phe Glu Ser Lys Asn Asn Ile Gly Ile Glu Tyr Ser Lys
65                  70                  75                  80

Asp Ser Arg Asn Lys Leu Ser Tyr Arg Asn Lys Pro Ser Ile Ala Thr
                85                  90                  95

Asn Leu Glu Tyr Lys Thr Leu Cys Asp Met Ile Lys Gly Thr Ser Gly
            100                 105                 110

Thr Glu Lys Glu Phe Leu Arg Tyr Leu Leu Phe Gly Ile Lys Cys Ile
        115                 120                 125

Lys Lys Gly Val Glu Tyr Asn Ile Asp Lys Ile Lys Asp Val Ser Tyr
    130                 135                 140

Asn Asp Tyr Phe Asn Val Leu Asp Glu Lys Tyr Asn Thr Pro Cys Pro
145                 150                 155                 160

Asn Cys Lys Ser Arg Asn Thr Thr Pro Met Met Ile Gln Thr Arg Ala
                165                 170                 175

Ala Asp Glu Pro Pro Leu Val Arg His Ala Cys Arg Asp Cys Lys Gln
            180                 185                 190

His Phe Lys Pro Pro Lys Phe Arg Ala Phe Arg Asn Leu Asn Val Thr
        195                 200                 205

Thr Gln Ser Ile His Glu Asn Lys Glu Ile Thr Glu Ile Leu Pro Asp
    210                 215                 220
```

Asn Asn Pro Ser Pro Pro Glu Ser Pro Glu Pro Ala Ser Pro Ile Asp
225                 230                 235                 240

Asp Gly Leu Ile Arg Ser Thr Phe Asp Arg Asn Asp Glu Pro Pro Glu
            245                 250                 255

Asp Asp Glu

<210> SEQ ID NO 37
<211> LENGTH: 567
<212> TYPE: PRT
<213> ORGANISM: Vaccinia virus

<400> SEQUENCE: 37

Met Asp Phe Ile Arg Arg Lys Tyr Leu Ile Tyr Thr Val Glu Asn Asn
1               5                   10                  15

Ile Asp Phe Leu Lys Asp Asp Thr Leu Ser Lys Val Asn Asn Phe Thr
            20                  25                  30

Leu Asn His Val Leu Ala Leu Lys Tyr Leu Val Ser Asn Phe Pro Gln
        35                  40                  45

His Val Ile Thr Lys Asp Val Leu Ala Asn Thr Asn Phe Phe Val Phe
    50                  55                  60

Ile His Met Val Arg Cys Cys Lys Val Tyr Glu Ala Val Leu Arg His
65                  70                  75                  80

Ala Phe Asp Ala Pro Thr Leu Tyr Val Lys Ala Leu Thr Lys Asn Tyr
                85                  90                  95

Leu Ser Phe Ser Asn Ala Ile Gln Ser Tyr Lys Glu Thr Val His Lys
            100                 105                 110

Leu Thr Gln Asp Glu Lys Phe Leu Glu Val Ala Glu Tyr Met Asp Glu
        115                 120                 125

Leu Gly Glu Leu Ile Gly Val Asn Tyr Asp Leu Val Leu Asn Pro Leu
    130                 135                 140

Phe His Gly Gly Glu Pro Ile Lys Asp Met Glu Ile Ile Phe Leu Lys
145                 150                 155                 160

Leu Phe Lys Lys Thr Asp Phe Lys Val Val Lys Leu Ser Val Ile
                165                 170                 175

Arg Leu Leu Ile Trp Ala Tyr Leu Ser Lys Lys Asp Thr Gly Ile Glu
            180                 185                 190

Phe Ala Asp Asn Asp Arg Gln Asp Ile Tyr Thr Leu Phe Gln Gln Thr
        195                 200                 205

Gly Arg Ile Val His Ser Asn Leu Thr Glu Thr Phe Arg Asp Tyr Ile
    210                 215                 220

Phe Pro Gly Asp Lys Thr Ser Tyr Trp Val Trp Leu Asn Glu Ser Ile
225                 230                 235                 240

Ala Asn Asp Ala Asp Ile Val Leu Asn Arg His Ala Ile Thr Met Tyr
                245                 250                 255

Asp Lys Ile Leu Ser Tyr Ile Tyr Ser Glu Ile Lys Gln Gly Arg Val
            260                 265                 270

Asn Lys Asn Met Leu Lys Leu Val Tyr Ile Phe Glu Pro Glu Lys Asp
        275                 280                 285

Ile Arg Glu Leu Leu Leu Glu Ile Ile Tyr Asp Ile Pro Gly Asp Ile
    290                 295                 300

Leu Ser Ile Ile Asp Ala Lys Asn Asp Asp Trp Lys Lys Tyr Phe Ile
305                 310                 315                 320

Ser Phe Tyr Lys Ala Asn Phe Ile Asn Gly Asn Thr Phe Ile Ser Asp
                325                 330                 335

```
Arg Thr Phe Asn Glu Asp Leu Phe Arg Val Val Gln Ile Asp Pro
                340                 345                 350

Glu Tyr Phe Asp Asn Glu Arg Ile Met Ser Leu Phe Thr Ser Ala
            355                 360                 365

Ala Asp Ile Lys Arg Phe Asp Glu Leu Asp Ile Asn Asn Ser Tyr Ile
370                 375                 380

Ser Asn Ile Ile Tyr Glu Val Asn Asp Ile Thr Leu Asp Thr Met Asp
385                 390                 395                 400

Asp Met Lys Lys Cys Gln Ile Phe Asn Glu Asp Thr Ser Tyr Tyr Val
                405                 410                 415

Lys Glu Tyr Asn Thr Tyr Leu Phe Leu His Glu Ser Asp Pro Met Val
            420                 425                 430

Ile Glu Asn Gly Ile Leu Lys Lys Leu Ser Ser Ile Lys Ser Lys Ser
                435                 440                 445

Arg Arg Leu Asn Leu Phe Ser Lys Asn Ile Leu Lys Tyr Tyr Leu Asp
450                 455                 460

Gly Gln Leu Ala Arg Leu Gly Leu Val Leu Asp Asp Tyr Lys Gly Asp
465                 470                 475                 480

Leu Leu Val Lys Met Ile Asn His Leu Lys Ser Val Glu Asp Val Ser
                485                 490                 495

Ala Phe Val Arg Phe Ser Thr Asp Lys Asn Pro Ser Ile Leu Pro Ser
                500                 505                 510

Leu Ile Lys Thr Ile Leu Ala Ser Tyr Asn Ile Ser Ile Ile Val Leu
                515                 520                 525

Phe Gln Arg Phe Leu Arg Asp Asn Leu Tyr His Val Glu Glu Phe Leu
            530                 535                 540

Asp Lys Ser Ile His Leu Thr Lys Thr Asp Lys Lys Tyr Ile Leu Gln
545                 550                 555                 560

Leu Ile Arg His Gly Arg Ser
                565

<210> SEQ ID NO 38
<211> LENGTH: 273
<212> TYPE: PRT
<213> ORGANISM: Vaccinia virus

<400> SEQUENCE: 38

Met Ala Ala Thr Val Pro Arg Phe Asp Asp Val Tyr Lys Asn Ala Gln
1               5                   10                  15

Arg Arg Ile Leu Asp Gln Glu Thr Phe Phe Ser Arg Gly Leu Ser Arg
                20                  25                  30

Pro Leu Met Lys Asn Thr Tyr Leu Phe Asp Asn Tyr Ala Tyr Gly Trp
            35                  40                  45

Ile Pro Glu Thr Ala Ile Trp Ser Ser Arg Tyr Ala Asn Leu Asp Ala
        50                  55                  60

Ser Asp Tyr Tyr Pro Ile Ser Leu Gly Leu Leu Lys Lys Phe Glu Phe
65                  70                  75                  80

Leu Met Ser Leu Tyr Lys Gly Pro Ile Pro Val Tyr Glu Glu Lys Val
                85                  90                  95

Asn Thr Glu Phe Ile Ala Asn Gly Ser Phe Ser Gly Tyr Val Ser
            100                 105                 110

Tyr Leu Arg Lys Phe Ser Ala Leu Pro Thr Asn Glu Phe Ile Ser Phe
            115                 120                 125

Leu Leu Leu Thr Ser Ile Pro Ile Tyr Asn Ile Leu Phe Trp Phe Lys
        130                 135                 140
```

-continued

```
Asn Thr Gln Phe Asp Ile Thr Lys His Thr Leu Phe Arg Tyr Val Tyr
145                 150                 155                 160

Thr Asp Asn Ala Lys His Leu Ala Leu Ala Arg Tyr Met His Gln Thr
                165                 170                 175

Gly Asp Tyr Lys Pro Leu Phe Ser Arg Leu Lys Glu Asn Tyr Ile Phe
            180                 185                 190

Thr Gly Pro Val Pro Ile Ser Ile Lys Asp Ile Asp His Pro Asn Leu
        195                 200                 205

Ser Arg Ala Arg Ser Pro Ser Asp Tyr Glu Thr Leu Ala Asn Ile Ser
    210                 215                 220

Thr Ile Leu Tyr Phe Thr Lys Tyr Asp Pro Val Leu Met Phe Leu Leu
225                 230                 235                 240

Phe Tyr Val Pro Gly Tyr Ser Ile Thr Thr Lys Ile Thr Pro Ala Val
                245                 250                 255

Glu Tyr Leu Met Asp Lys Leu Asn Leu Thr Lys Ser Asp Val Gln Leu
            260                 265                 270

Leu

<210> SEQ ID NO 39
<211> LENGTH: 95
<212> TYPE: PRT
<213> ORGANISM: Vaccinia virus

<400> SEQUENCE: 39

Met Asn Pro Lys His Trp Gly Arg Ala Val Trp Thr Ile Ile Phe Ile
1               5                   10                  15

Val Leu Ser Gln Ala Gly Leu Asp Gly Asn Ile Glu Ala Cys Lys Arg
            20                  25                  30

Lys Leu Tyr Thr Ile Val Ser Thr Leu Pro Cys Pro Ala Cys Arg Arg
        35                  40                  45

His Ala Thr Ile Ala Ile Glu Asp Asn Asn Val Met Ser Ser Asp Asp
    50                  55                  60

Leu Asn Tyr Ile Tyr Tyr Phe Phe Ile Arg Leu Phe Asn Asn Leu Ala
65                  70                  75                  80

Ser Asp Pro Lys Tyr Ala Ile Asp Val Thr Lys Val Asn Pro Leu
                85                  90                  95

<210> SEQ ID NO 40
<211> LENGTH: 312
<212> TYPE: PRT
<213> ORGANISM: Vaccinia virus

<400> SEQUENCE: 40

Met Ala Glu Phe Glu Asp Gln Leu Val Phe Asn Ser Ile Ser Ala Arg
1               5                   10                  15

Ala Leu Lys Ala Tyr Phe Thr Ala Lys Ile Asn Glu Met Val Asp Glu
            20                  25                  30

Leu Val Thr Arg Lys Cys Pro Gln Lys Lys Lys Ser Gln Ala Lys Lys
        35                  40                  45

Pro Glu Leu Arg Ile Pro Val Asp Leu Val Lys Ser Ser Phe Val Lys
    50                  55                  60

Lys Phe Gly Leu Cys Asn Tyr Gly Gly Ile Leu Ile Ser Leu Ile Asn
65                  70                  75                  80

Ser Leu Val Glu Asn Asn Phe Phe Thr Lys Asp Gly Lys Leu Asp Asp
                85                  90                  95
```

```
Thr Gly Lys Lys Glu Leu Val Leu Thr Asp Val Glu Lys Arg Ile Leu
            100                 105                 110

Asn Thr Ile Asp Lys Ser Ser Pro Leu Tyr Ile Asp Ile Ser Asp Val
        115                 120                 125

Lys Val Leu Ala Ala Arg Leu Lys Arg Ser Ala Thr Gln Phe Asn Phe
    130                 135                 140

Asn Gly His Thr Tyr His Leu Glu Asn Asp Lys Ile Glu Asp Leu Ile
145                 150                 155                 160

Asn Gln Leu Val Lys Asp Glu Ser Ile Gln Leu Asp Glu Lys Ser Ser
                165                 170                 175

Ile Lys Asp Ser Met Tyr Val Ile Pro Asp Glu Leu Ile Asp Val Leu
            180                 185                 190

Lys Thr Arg Leu Phe Arg Ser Pro Gln Val Lys Asp Asn Ile Ile Ser
        195                 200                 205

Arg Thr Arg Leu Tyr Asp Tyr Phe Thr Arg Val Thr Lys Arg Asp Glu
    210                 215                 220

Ser Ser Ile Tyr Val Ile Leu Lys Asp Pro Arg Ile Ala Ser Ile Leu
225                 230                 235                 240

Ser Leu Glu Thr Val Lys Met Gly Ala Phe Met Tyr Thr Lys His Ser
                245                 250                 255

Met Leu Thr Asn Ala Ile Ser Ser Arg Val Asp Arg Tyr Ser Lys Lys
            260                 265                 270

Phe Gln Glu Ser Phe Tyr Glu Asp Ile Val Glu Phe Val Lys Glu Asn
        275                 280                 285

Glu Arg Val Asn Val Ser Arg Val Val Glu Cys Leu Thr Val Pro Asn
    290                 295                 300

Ile Thr Ile Ser Ser Asn Ala Glu
305                 310

<210> SEQ ID NO 41
<211> LENGTH: 269
<212> TYPE: PRT
<213> ORGANISM: Vaccinia virus

<400> SEQUENCE: 41

Met Ser Lys Val Ile Lys Lys Arg Val Glu Thr Ser Pro Arg Pro Thr
1               5                   10                  15

Ala Ser Ser Asp Ser Leu Gln Thr Cys Ala Gly Val Ile Glu Tyr Ala
            20                  25                  30

Lys Ser Ile Ser Lys Ser Asn Ala Lys Cys Ile Glu Tyr Val Thr Leu
        35                  40                  45

Asn Ala Ser Gln Tyr Ala Asn Cys Ser Ser Ile Ser Ile Lys Leu Thr
    50                  55                  60

Asp Ser Leu Ser Ser Gln Met Thr Ser Thr Phe Ile Met Leu Glu Gly
65                  70                  75                  80

Glu Thr Lys Leu Tyr Lys Asn Lys Ser Lys Gln Asp Arg Ser Asp Gly
                85                  90                  95

Tyr Phe Leu Lys Ile Lys Val Thr Ala Ala Ser Pro Met Leu Tyr Gln
            100                 105                 110

Leu Leu Glu Ala Val Tyr Gly Asn Ile Lys His Lys Glu Arg Ile Pro
        115                 120                 125

Asn Ser Leu His Ser Leu Ser Val Glu Thr Ile Thr Glu Lys Thr Phe
    130                 135                 140

Lys Asp Glu Ser Ile Phe Ile Asn Lys Leu Asn Gly Ser Met Val Glu
145                 150                 155                 160
```

```
Tyr Val Ser Thr Gly Glu Ser Ser Ile Leu Arg Ser Ile Glu Gly Glu
                165                 170                 175

Leu Glu Ser Leu Ser Lys Arg Glu Arg Gln Leu Ala Lys Ala Ile Ile
            180                 185                 190

Thr Pro Ile Val Phe Tyr Arg Ser Gly Thr Glu Thr Lys Ile Thr Phe
        195                 200                 205

Ala Leu Lys Lys Leu Ile Ile Asp Arg Glu Val Val Ala Asn Val Ile
    210                 215                 220

Gly Leu Ser Gly Asp Ser Glu Arg Val Ser Met Thr Glu Asn Val Glu
225                 230                 235                 240

Glu Asp Leu Ala Arg Asn Leu Gly Leu Val Asp Ile Asp Asp Glu Tyr
                245                 250                 255

Asp Glu Asp Ser Asp Lys Glu Lys Pro Ile Phe Asn Val
                260                 265

<210> SEQ ID NO 42
<211> LENGTH: 79
<212> TYPE: PRT
<213> ORGANISM: Vaccinia virus

<400> SEQUENCE: 42

Met Val Asp Ala Ile Thr Val Leu Thr Ala Ile Gly Ile Thr Val Leu
1               5                   10                  15

Met Leu Leu Met Val Ile Ser Gly Ala Ala Met Ile Val Lys Glu Leu
            20                  25                  30

Asn Pro Asn Asp Ile Phe Thr Met Gln Ser Leu Lys Phe Asn Arg Ala
        35                  40                  45

Val Thr Ile Phe Lys Tyr Ile Gly Leu Phe Ile Tyr Ile Pro Gly Thr
    50                  55                  60

Ile Ile Leu Tyr Ala Thr Tyr Val Lys Ser Leu Leu Met Lys Ser
65                  70                  75

<210> SEQ ID NO 43
<211> LENGTH: 144
<212> TYPE: PRT
<213> ORGANISM: Vaccinia virus

<400> SEQUENCE: 43

Met Phe Phe Ala Asp Asp Asp Ser Phe Phe Lys Tyr Leu Ala Ser Gln
1               5                   10                  15

Asp Asp Glu Ser Ser Leu Ser Asp Ile Leu Gln Ile Thr Gln Tyr Leu
            20                  25                  30

Asp Phe Leu Leu Leu Leu Ile Gln Ser Lys Asn Lys Leu Glu Ala
        35                  40                  45

Val Gly His Cys Tyr Glu Ser Leu Ser Glu Glu Tyr Arg Gln Leu Thr
    50                  55                  60

Lys Phe Thr Asp Phe Gln Asp Phe Lys Lys Leu Phe Asn Lys Val Pro
65                  70                  75                  80

Ile Val Thr Asp Gly Arg Val Lys Leu Asn Lys Gly Tyr Leu Phe Asp
                85                  90                  95

Phe Val Ile Ser Leu Met Arg Phe Lys Lys Glu Ser Ser Leu Ala Thr
            100                 105                 110

Thr Ala Ile Asp Pro Ile Arg Tyr Ile Asp Pro Arg Arg Asp Ile Ala
        115                 120                 125

Phe Ser Asn Val Met Asp Ile Leu Lys Ser Asn Lys Val Asn Asn Asn
    130                 135                 140
```

<210> SEQ ID NO 44
<211> LENGTH: 333
<212> TYPE: PRT
<213> ORGANISM: Vaccinia virus

<400> SEQUENCE: 44

```
Met Asp Val Val Ser Leu Asp Lys Pro Phe Met Tyr Phe Glu Glu Ile
1               5                  10                  15

Asp Asn Glu Leu Asp Tyr Glu Pro Glu Ser Ala Asn Glu Val Ala Lys
            20                  25                  30

Lys Leu Pro Tyr Gln Gly Gln Leu Lys Leu Leu Leu Gly Glu Leu Phe
        35                  40                  45

Phe Leu Ser Lys Leu Gln Arg His Gly Ile Leu Asp Gly Ala Thr Val
    50                  55                  60

Val Tyr Ile Gly Ser Ala Pro Gly Thr His Ile Arg Tyr Leu Arg Asp
65                  70                  75                  80

His Phe Tyr Asn Leu Gly Val Ile Ile Lys Trp Met Leu Ile Asp Gly
                85                  90                  95

Arg His His Asp Pro Ile Leu Asn Gly Leu Arg Asp Val Thr Leu Val
            100                 105                 110

Thr Arg Phe Val Asp Glu Glu Tyr Leu Arg Ser Ile Lys Lys Gln Leu
        115                 120                 125

His Pro Ser Lys Ile Ile Leu Ile Ser Asp Val Arg Ser Lys Arg Gly
    130                 135                 140

Gly Asn Glu Pro Ser Thr Ala Asp Leu Leu Ser Asn Tyr Ala Leu Gln
145                 150                 155                 160

Asn Val Met Ile Ser Ile Leu Asn Pro Val Ala Ser Ser Leu Lys Trp
                165                 170                 175

Arg Cys Pro Phe Pro Asp Gln Trp Ile Lys Asp Phe Tyr Ile Pro His
            180                 185                 190

Gly Asn Lys Met Leu Gln Pro Phe Ala Pro Ser Tyr Ser Ala Glu Met
        195                 200                 205

Arg Leu Leu Ser Ile Tyr Thr Gly Glu Asn Met Arg Leu Thr Arg Val
    210                 215                 220

Thr Lys Ser Asp Ala Val Asn Tyr Glu Lys Lys Met Tyr Tyr Leu Asn
225                 230                 235                 240

Lys Ile Val Arg Asn Lys Val Val Asn Phe Asp Tyr Pro Asn Gln
                245                 250                 255

Glu Tyr Asp Tyr Phe His Met Tyr Phe Met Leu Arg Thr Val Tyr Cys
            260                 265                 270

Asn Lys Thr Phe Pro Thr Thr Lys Ala Lys Val Leu Phe Leu Gln Gln
        275                 280                 285

Ser Ile Phe Arg Phe Leu Asn Ile Pro Thr Thr Ser Thr Glu Lys Val
    290                 295                 300

Ser His Glu Pro Ile Gln Arg Lys Ile Ser Ser Lys Asn Ser Met Ser
305                 310                 315                 320

Lys Asn Arg Asn Ser Lys Arg Ser Val Arg Ser Asn Lys
                325                 330
```

<210> SEQ ID NO 45
<211> LENGTH: 161
<212> TYPE: PRT
<213> ORGANISM: Vaccinia virus

<400> SEQUENCE: 45

```
Met Ser Ser Phe Val Thr Asn Gly Tyr Leu Pro Val Thr Leu Glu Pro
1               5                   10                  15

His Glu Leu Thr Leu Asp Ile Lys Thr Asn Ile Arg Asn Ala Val Tyr
            20                  25                  30

Lys Thr Tyr Leu His Arg Glu Ile Ser Gly Lys Met Ala Lys Lys Ile
        35                  40                  45

Glu Ile Arg Glu Asp Val Glu Leu Pro Leu Gly Glu Ile Val Asn Asn
50                  55                  60

Ser Val Val Ile Asn Val Pro Cys Val Ile Thr Tyr Ala Tyr Tyr His
65                  70                  75                  80

Val Gly Asp Ile Val Arg Gly Thr Leu Asn Ile Glu Asp Glu Ser Asn
            85                  90                  95

Val Thr Ile Gln Cys Gly Asp Leu Ile Cys Lys Leu Ser Arg Asp Ser
        100                 105                 110

Gly Thr Val Ser Phe Ser Asp Ser Lys Tyr Cys Phe Phe Arg Asn Gly
    115                 120                 125

Asn Ala Tyr Asp Asn Gly Ser Glu Val Thr Ala Val Leu Met Glu Ala
130                 135                 140

Gln Gln Gly Ile Glu Ser Ser Phe Val Phe Leu Ala Asn Ile Val Asp
145                 150                 155                 160

Ser

<210> SEQ ID NO 46
<211> LENGTH: 213
<212> TYPE: PRT
<213> ORGANISM: Vaccinia virus

<400> SEQUENCE: 46

Met Gly Ile Thr Met Asp Glu Glu Val Ile Phe Glu Thr Pro Arg Glu
1               5                   10                  15

Leu Ile Ser Ile Lys Arg Ile Lys Asp Ile Pro Arg Ser Lys Asp Thr
            20                  25                  30

His Val Phe Ala Ala Cys Ile Thr Ser Asp Gly Tyr Pro Leu Ile Gly
        35                  40                  45

Ala Arg Arg Thr Ser Phe Ala Phe Gln Ala Ile Leu Ser Gln Gln Asn
50                  55                  60

Ser Asp Ser Ile Phe Arg Val Ser Thr Lys Leu Leu Arg Phe Met Tyr
65                  70                  75                  80

Tyr Asn Glu Leu Arg Glu Ile Phe Arg Arg Leu Arg Lys Gly Ser Ile
            85                  90                  95

Asn Asp Ile Asp Pro His Phe Glu Glu Leu Ile Leu Leu Gly Gly Lys
        100                 105                 110

Leu Asp Lys Lys Glu Ser Ile Lys Asp Cys Leu Arg Arg Glu Leu Lys
    115                 120                 125

Glu Glu Ser Asp Glu Arg Ile Thr Val Lys Glu Phe Gly Asn Val Ile
130                 135                 140

Leu Lys Leu Thr Thr Arg Asp Lys Leu Phe Asn Lys Val Tyr Ile Ser
145                 150                 155                 160

Tyr Cys Met Ala Cys Phe Ile Asn Gln Ser Leu Glu Asp Leu Ser His
            165                 170                 175

Thr Ser Ile Tyr Asn Val Glu Ile Arg Lys Ile Lys Ser Leu Asn Asp
        180                 185                 190

Cys Ile Asn Asp Asp Lys Tyr Glu Tyr Leu Ser Tyr Ile Tyr Asn Met
    195                 200                 205
```

Leu Val Asn Ser Lys
    210

<210> SEQ ID NO 47
<211> LENGTH: 1156
<212> TYPE: PRT
<213> ORGANISM: Vaccinia virus

<400> SEQUENCE: 47

Met Asp Gln Arg Leu Gly Tyr Lys Phe Leu Val Pro Asp Pro Lys Ala
1               5                   10                  15

Gly Val Phe Tyr Arg Pro Leu His Phe Gln Tyr Val Ser Tyr Ser Asn
            20                  25                  30

Phe Ile Leu His Arg Leu His Glu Ile Leu Thr Val Lys Arg Pro Leu
        35                  40                  45

Leu Ser Phe Lys Asn Asn Thr Glu Arg Ile Met Ile Glu Ile Ser Asn
    50                  55                  60

Val Lys Val Thr Pro Pro Asp Tyr Ser Pro Ile Ile Ala Ser Ile Lys
65                  70                  75                  80

Gly Lys Ser Tyr Asp Ala Leu Ala Thr Phe Thr Val Asn Ile Phe Lys
                85                  90                  95

Glu Val Met Thr Lys Glu Gly Ile Ser Ile Thr Lys Ile Ser Ser Tyr
            100                 105                 110

Glu Gly Lys Asp Ser His Leu Ile Lys Ile Pro Leu Leu Ile Gly Tyr
        115                 120                 125

Gly Asn Lys Asn Pro Leu Asp Thr Ala Lys Tyr Leu Val Pro Asn Val
    130                 135                 140

Ile Gly Gly Val Phe Ile Asn Lys Gln Ser Val Glu Lys Val Gly Ile
145                 150                 155                 160

Asn Leu Val Glu Lys Ile Thr Thr Trp Pro Lys Phe Arg Val Val Lys
                165                 170                 175

Pro Asn Ser Phe Thr Phe Ser Phe Ser Ser Val Ser Pro Pro Asn Val
            180                 185                 190

Leu Pro Thr Arg Tyr Arg His Tyr Lys Ile Ser Leu Asp Ile Ser Gln
        195                 200                 205

Leu Glu Ala Leu Asn Ile Ser Ser Thr Lys Thr Phe Ile Thr Val Asn
    210                 215                 220

Ile Val Leu Leu Ser Gln Tyr Leu Ser Arg Val Ser Leu Glu Phe Ile
225                 230                 235                 240

Arg Arg Ser Leu Ser Tyr Asp Met Pro Pro Glu Val Val Tyr Leu Val
                245                 250                 255

Asn Ala Ile Ile Asp Ser Ala Lys Arg Ile Thr Glu Ser Ile Thr Asp
            260                 265                 270

Phe Asn Ile Asp Thr Tyr Ile Asn Asp Leu Val Glu Ala Glu His Ile
        275                 280                 285

Lys Gln Lys Ser Gln Leu Thr Ile Asn Glu Phe Lys Tyr Glu Met Leu
    290                 295                 300

His Asn Phe Leu Pro His Met Asn Tyr Thr Pro Asp Gln Leu Lys Gly
305                 310                 315                 320

Phe Tyr Met Ile Ser Leu Leu Arg Lys Phe Leu Tyr Cys Ile Tyr His
                325                 330                 335

Thr Ser Arg Tyr Pro Asp Arg Asp Ser Met Val Cys His Arg Ile Leu
            340                 345                 350

Thr Tyr Gly Lys Tyr Phe Glu Thr Leu Ala His Asp Glu Leu Glu Asn

-continued

```
            355                 360                 365
Tyr Ile Gly Asn Ile Arg Asn Asp Ile Met Asn Asn His Lys Asn Arg
    370                 375                 380
Gly Thr Tyr Ala Val Asn Ile His Val Leu Thr Thr Pro Gly Leu Asn
385                 390                 395                 400
His Ala Phe Ser Ser Leu Leu Ser Gly Lys Phe Lys Lys Ser Asp Gly
                405                 410                 415
Ser Tyr Arg Thr His Pro His Tyr Ser Trp Met Gln Asn Ile Ser Ile
            420                 425                 430
Pro Arg Ser Val Gly Phe Tyr Pro Asp Gln Val Lys Ile Ser Lys Met
            435                 440                 445
Phe Ser Val Arg Lys Tyr His Pro Ser Gln Tyr Leu Tyr Phe Cys Ser
450                 455                 460
Ser Asp Val Pro Glu Arg Gly Pro Gln Val Gly Leu Val Ser Gln Leu
465                 470                 475                 480
Ser Val Leu Ser Ser Ile Thr Asn Ile Leu Thr Ser Glu Tyr Leu Asp
                485                 490                 495
Leu Glu Lys Lys Ile Cys Glu Tyr Ile Arg Ser Tyr Tyr Lys Asp Asp
                500                 505                 510
Ile Ser Tyr Phe Glu Thr Gly Phe Pro Ile Thr Ile Glu Asn Ala Leu
            515                 520                 525
Val Ala Ser Leu Asn Pro Asn Met Ile Cys Asp Phe Val Thr Asp Phe
530                 535                 540
Arg Arg Arg Lys Arg Met Gly Phe Phe Gly Asn Leu Glu Val Gly Ile
545                 550                 555                 560
Thr Leu Val Arg Asp His Met Asn Glu Ile Arg Ile Asn Ile Gly Ala
                565                 570                 575
Gly Arg Leu Val Arg Pro Phe Leu Val Val Asp Asn Gly Glu Leu Met
            580                 585                 590
Met Asp Val Cys Pro Glu Leu Glu Ser Arg Leu Asp Asp Met Thr Phe
            595                 600                 605
Ser Asp Ile Gln Lys Glu Phe Pro His Val Ile Glu Met Val Asp Ile
            610                 615                 620
Glu Gln Phe Thr Phe Ser Asn Val Cys Glu Ser Val Gln Lys Phe Arg
625                 630                 635                 640
Met Met Ser Lys Asp Glu Arg Lys Gln Tyr Asp Leu Cys Asp Phe Pro
                645                 650                 655
Ala Glu Phe Arg Asp Gly Tyr Val Ala Ser Ser Leu Val Gly Ile Asn
                660                 665                 670
His Asn Ser Gly Pro Arg Ala Ile Leu Gly Cys Ala Gln Ala Lys Gln
            675                 680                 685
Ala Ile Ser Cys Leu Ser Ser Asp Ile Arg Asn Lys Ile Asp Asn Gly
            690                 695                 700
Ile His Leu Met Tyr Pro Glu Arg Pro Ile Val Ile Ser Lys Ala Leu
705                 710                 715                 720
Glu Thr Ser Lys Ile Ala Ala Asn Cys Phe Gly Gln His Val Thr Ile
                725                 730                 735
Ala Leu Met Ser Tyr Lys Gly Ile Asn Gln Glu Asp Gly Ile Ile Ile
                740                 745                 750
Lys Lys Gln Phe Ile Gln Arg Gly Gly Leu Asp Ile Val Thr Ala Lys
            755                 760                 765
Lys His Gln Val Glu Ile Pro Leu Glu Asn Phe Asn Asn Lys Glu Arg
            770                 775                 780
```

-continued

Asp Arg Ser Asn Ala Tyr Ser Lys Leu Glu Ser Asn Gly Leu Val Arg
785                 790                 795                 800

Leu Asn Ala Phe Leu Glu Ser Gly Asp Ala Ile Ala Arg Asn Ile Ser
            805                 810                 815

Ser Arg Thr Leu Glu Asp Asp Phe Ala Arg Asp Asn Gln Ile Ser Phe
        820                 825                 830

Asp Val Ser Glu Lys Tyr Thr Asp Met Tyr Lys Ser Arg Val Glu Arg
            835                 840                 845

Val Gln Val Glu Leu Thr Asp Lys Val Lys Val Arg Val Leu Thr Met
850                 855                 860

Lys Glu Arg Arg Pro Ile Leu Gly Asp Lys Phe Thr Arg Thr Arg Ser
865                 870                 875                 880

Gln Lys Gly Thr Val Ala Tyr Ile Ala Asp Glu Thr Glu Leu Pro Tyr
                885                 890                 895

Asp Glu Asn Gly Ile Thr Pro Asp Val Ile Asn Ser Thr Ser Ile
            900                 905                 910

Phe Ser Arg Lys Thr Ile Ser Met Leu Ile Glu Val Ile Leu Thr Ala
        915                 920                 925

Ala Tyr Ser Ala Lys Pro Tyr Asn Asn Lys Gly Glu Asn Arg Pro Val
930                 935                 940

Cys Phe Pro Ser Ser Asn Glu Thr Ser Ile Asp Thr Tyr Met Gln Phe
945                 950                 955                 960

Ala Lys Gln Cys Tyr Glu His Ser Asn Pro Lys Leu Ser Asp Glu Glu
            965                 970                 975

Leu Ser Asp Lys Ile Phe Cys Glu Lys Ile Leu Tyr Asp Pro Glu Thr
        980                 985                 990

Asp Lys Pro Tyr Ala Ser Lys Val Phe Phe Gly Pro Ile Tyr Tyr Leu
            995                 1000                1005

Arg Leu Arg His Leu Thr Gln Asp Lys Ala Thr Val Arg Cys Arg
    1010                1015                1020

Gly Lys Lys Thr Lys Leu Ile Arg Gln Ala Asn Glu Gly Arg Lys
    1025                1030                1035

Arg Gly Gly Gly Ile Lys Phe Gly Glu Met Glu Arg Asp Cys Leu
    1040                1045                1050

Ile Ala His Gly Ala Ala Asn Thr Ile Thr Glu Val Leu Lys Asp
    1055                1060                1065

Ser Glu Glu Asp Tyr Gln Asp Val Tyr Val Cys Glu Asn Cys Gly
    1070                1075                1080

Asp Ile Ala Ala Gln Ile Lys Gly Ile Asn Thr Cys Leu Arg Cys
    1085                1090                1095

Ser Lys Leu Asn Leu Ser Pro Leu Leu Thr Lys Ile Asp Thr Thr
    1100                1105                1110

His Val Ser Lys Val Phe Leu Thr Gln Met Asn Ala Arg Gly Val
    1115                1120                1125

Lys Val Lys Leu Asp Phe Glu Arg Arg Pro Pro Ser Phe Tyr Lys
    1130                1135                1140

Pro Leu Asp Lys Val Asp Leu Lys Pro Ser Phe Leu Val
    1145                1150                1155

<210> SEQ ID NO 48
<211> LENGTH: 146
<212> TYPE: PRT
<213> ORGANISM: Vaccinia virus

```
<400> SEQUENCE: 48

Met Asn Ser Leu Ser Ile Phe Phe Ile Val Val Ala Thr Ala Ala Val
1               5                   10                  15

Cys Leu Leu Phe Ile Gln Gly Tyr Ser Ile Tyr Glu Asn Tyr Gly Asn
                20                  25                  30

Ile Lys Glu Phe Asn Ala Thr His Ala Ala Phe Glu Tyr Ser Lys Ser
            35                  40                  45

Ile Gly Gly Thr Pro Ala Leu Asp Arg Arg Val Gln Asp Val Asn Asp
        50                  55                  60

Thr Ile Ser Asp Val Lys Gln Lys Trp Arg Cys Val Val Tyr Pro Gly
65                  70                  75                  80

Asn Gly Phe Val Ser Ala Ser Ile Phe Gly Phe Gln Ala Glu Val Gly
                85                  90                  95

Pro Asn Asn Thr Arg Ser Ile Arg Lys Phe Asn Thr Met Gln Gln Cys
                100                 105                 110

Ile Asp Phe Thr Phe Ser Asp Val Ile Asn Ile Asn Ile Tyr Asn Pro
            115                 120                 125

Cys Val Val Pro Asn Ile Asn Asn Ala Glu Cys Gln Phe Leu Lys Ser
        130                 135                 140

Val Leu
145
```